(12) United States Patent
Gregor et al.

(10) Patent No.: US 7,365,080 B2
(45) Date of Patent: Apr. 29, 2008

(54) PHARMACEUTICAL COMPOSITIONS COMPRISING THIENO[2,3-C]PYRIDINE DERIVATIVES AND USE THEREOF

(75) Inventors: Paul Gregor, Rehovot (IL); Nicholas Harris, Rehovot (IL); Juraj Koppel, Kosice (IL); Regina Zhuk, Ness Ziona (IL)

(73) Assignee: Rimonyx Pharmaceuticals Ltd., Ness-Ziona (IL)

( * ) Notice: Subject to any disclaimer, the term of this patent is extended or adjusted under 35 U.S.C. 154(b) by 217 days.

(21) Appl. No.: 10/543,065

(22) PCT Filed: Feb. 5, 2004

(86) PCT No.: PCT/IL2004/000121

§ 371 (c)(1),
(2), (4) Date: Oct. 19, 2005

(87) PCT Pub. No.: WO2004/069149

PCT Pub. Date: Aug. 19, 2004

(65) Prior Publication Data

US 2006/0135529 A1    Jun. 22, 2006

(30) Foreign Application Priority Data

Feb. 5, 2003   (IL) ..................... 154306

(51) Int. Cl.
| | |
|---|---|
| *A01N 43/42* | (2006.01) |
| *A61K 31/44* | (2006.01) |
| *C07D 471/02* | (2006.01) |
| *C07D 491/02* | (2006.01) |
| *C07D 498/02* | (2006.01) |

(52) U.S. Cl. ..................... 514/301; 546/114

(58) Field of Classification Search ............... 546/114; 514/301

See application file for complete search history.

(56) References Cited

U.S. PATENT DOCUMENTS 6,232,320 B1   5/2001   Stewart et al.

OTHER PUBLICATIONS

Balakin et al., Journal of chemical information and computer sciences, 2002, vol. 42, pp. 1332-1342.*
Engbring et al., Cancer Research, 2002, vol. 62, pp. 3549-3554.*
Balakin, et al., *Property-based design of GPCR-targeted library*. J. Chem. Inf. Comput. Sci. 2002, vol. 42, pp. 132-1342, especially p. 1339, Fig. 5.
Fujita, et al., *Synthesis and bioactivities of novel bicyclic thiophenes and 4, 5, 6, 6-tetrahydrothieno[2,3-c]pyridines as inhibitors of tumor necrosis factor-alpha (TNF-alpha) production*. Bioorganic & Medical Chemistry Letters. 2002, vol. 12, pp. 1897-1900, especially p. 1899, Table 3.
Fujita, et al. *Synthesis and bioactivities of novel 4, 5, 6, 7-tetrahydrothieno[2,3-c]pyridines as inhibitors of tumor necrosis factor-alpha (TNF-alpha) production*. Bioorganic & Medical Chemistry Letters. 2002, vol. 12, pp. 1607-1611, especially p. 1608.

* cited by examiner

*Primary Examiner*—Margaret D. Seaman
*Assistant Examiner*—Niloofar Rahmani
(74) *Attorney, Agent, or Firm*—Browdy and Neimark

(57) ABSTRACT

The present invention provides thieno[2,3-C]pyridine derivatives, pharmaceutical compositions comprising the thieno[2,3-C]pyridine derivatives, and methods of use thereof. The compounds capable of inhibiting glycosaminoglycan (GAG) interactions with effector cell adhesion molecules (ECAM) are useful for treating diseases and disorders mediated by GAG-ECAMs interactions, particularly inflammatory and autoimmune diseases, viral diseases, cancer, and amyloid disorders.

28 Claims, 11 Drawing Sheets

PHARMACEUTICAL COMPOSITIONS COMPRISING THIENO[2,3-C]PYRIDINE DERIVATIVES AND USE THEREOF

FIELD OF INVENTION

The present invention relates to pharmaceutical compositions comprising thieno[2,3-c]pyridine compounds capable of inhibiting the interactions between effector cell adhesion molecules (ECAMs), particularly selectins, and glycosaminoglycans (GAGs), particularly heparan sulfate glycosaminoglycans (HS-GAGs), and to methods for the treatment or prevention of diseases or disorders related to cell adhesion and cell migration, particularly for the treatment or prevention of inflammatory and autoimmune diseases and disorders, as well as of viral diseases, cancer, and amyloid disorders.

BACKGROUND OF THE INVENTION

The inflammatory response is mediated primarily by leukocytes, neutrophils and lymphocytes, which circulate in the blood and reversibly interact with the vascular endothelium. In response to inflammatory stimuli, the leukocytes adhere tightly to the vascular endothelium, migrate (extravasate) through the vessel wall, and subsequently move along a chemotactic gradient toward the inflammatory stimulus. The interaction of leukocytes with vascular endothelial cells is thus an essential initial step in the inflammatory response. Selectins play a key role in inflammation, as they are responsible for the initial attachment of blood borne leukocytes to the vasculature. Preventing selectin-mediated cell adhesion can ameliorate or circumvent the deleterious consequences of inflammation. Therefore, selectins are the prime target for the therapy of cell-adhesion disorders, specifically for treatment of inflammation.

Selectins regulate neutrophil and lymphocyte adhesion to and entry into lymphoid tissues and sites of inflammation (Rosen, Am. J. Respir. Cell. Mol. Biol., 3:397-402, 1990). The three known selectins are E-selectin (formerly known as ELAM.1), P-selectin (formerly known as PADGEM, GMP-140, or CD61) and L-selectin (formerly known as mLHR, Leu8, TQ-1, gp90, MEL, Lam-1, or Lecam-1) (Lasky, Annu. Rev. Biochem. 64:113, 1995; Kansas, Blood 88:3259, 1996). Each selectin is regulated differently, and participates in a different manner in the process of inflammation or immunity. The lectin domains of each selectin are critical to the adhesive functions of the proteins. The selectins are responsible for leukocyte capture from the blood stream and mediate their intermittent attachment with consequent leukocyte "rolling" along the endothelial cell surface. This capture allows the cascade of secondary, tighter cell-adhesive events to take place. L-selectin is constitutively expressed by leukocytes and mediates lymphocyte adhesion to peripheral lymph node high endothelial venules, and neutrophil adhesion to cytokine-activated endothelial cells (Spertini et al. J. Immunol. 147:2565-2573, 1991). In inflammatory disorders it may be L-selectin that plays the most significant role (Shimizu et al., Immunol. Today 13:106, 1992; Picker et al., Annu. Rev. Immunol. 10:561, 1992).

Buerke et al. demonstrated the important role of selectins in inflammatory states such as ischemia-reperfusion injury in cats (Buerke, M. et al., J. Clin. Invest. 93:1140,1994). The presence of L-selectin and E- or P-selectin ligands on mononuclear cells has implicated these receptor-ligand interactions in chronic inflammation. (L. Lasky Annu. Rev. Biochem. 64:113-39, 1995). Monoclonal antibodies to L-selectin prevent neutrophil emigration into inflamed skin (Lewinsohn et al., J. Immunol. 138:4313, 1987), neutrophil and monocyte emigration into inflamed ascites (Jutila et al., J. Immunol. 143:3318, 1989), and neutrophil emigration into inflamed peritoneum. Jasin et al. provide support for the use of antibodies in inhibiting neutrophil accumulation in inflamed synovium (Jasin et al., Arthritis Rheum. 33:S34, 1990). Monoclonal antibody EL-246, directed against both L-selectin and E-selectin, attenuated sepsis-induced lung injury (Ridings, P C et al., Arch Surg. 1199-1208, 1995). Monoclonal antibody SMART is an L-selectin blocking antibody that is being used in clinical trials for trauma associated with multiple organ failure (this condition is believed to be due in part to infiltration of inflammatory cells). The anti-L-selectin antibody is presumed to provide its therapeutic effect by preventing neutrophil adhesion to endothelium and it is active in vivo in a primate model of severe trauma (Schlag G et al, Critical Care Medicine 1999, 27, 1900-1907). It is believed that this monoclonal antibody will be also useful in the treatment of adult respiratory distress syndrome and myocardial infarction.

Glycosaminoglycans (also referred to herein as "GAG" or "GAGs") are naturally-occurring carbohydrate-based molecules implicated in the regulation of a number of cellular processes, including blood coagulation, angiogenesis, tumor growth, and smooth muscle cell proliferation, most likely by interaction with effector molecules. GAGs are often, but not always, found covalently bound to protein cores in structures called proteoglycans. Proteoglycan structures are abundant on cell surfaces and are associated with the extracellular matrix around cells. GAGs consist of repeating disaccharide units. For example, heparan sulfate glycosaminoglycans (also referred to herein as "HS-GAGs") consist of repeating disaccharide units of D-glucuronic acid and N-acetyl- or N-sulfo-D-glucosamine. The high molecular diversity of HS-GAGs is due to their unique sulfation pattern (Sasisekharan, R. and Venkataraman, G., Current Opinion in Chem. Biol., 4, 626-631, 2000; Lindahl, U. et al., J. Biol. Chem., 273, 24979-24982, 1998; Esko, J. and Selleck, S. B., Annu. Rev. Biochem., 71, 435-471, 2002). One of the most thoroughly studied HS-GAGs is the widely used anticoagulant heparin. Heparin is a highly sulfated form of heparan sulfate found in mast cells. Many important regulatory proteins including cytokines, growth factors, enzymes, and cell adhesion molecules bind tightly to heparin. Although interactions of proteins with GAGs such as heparin and heparan sulfate are of great biological importance, the structural requirements for protein-GAG binding have not been well characterized. Ionic interactions are important in promoting protein-GAG binding and the spacing of the charged residues may determine protein-GAG affinity and specificity.

The HS-GAG paradigm provides new approaches and strategies for therapeutic intervention at the cell-tissue-organ interface. For example, identification of specific HS-GAG sequences that affect particular biological processes will enable the development of novel molecular therapeutics based on polysaccharide sequence. Synthetic HS-GAGs, or molecular mimics of HS-GAG sequences, may provide new approaches for combating health problems such as bacterial and viral infections, atherosclerosis, cancer, and Alzheimer's disease.

Selectins mediate their adhesive functions via lectin domains that bind to carbohydrate ligands. Emerging evidence indicates that GAGs, and in particular HS-GAGs, are carbohydrate receptors with which the selectins interact (Nelson R M, et al., Blood 82, 3253-3258, 1993; Ma, Y Q and Geng, J G, J. Immunol. 165, 558-565, 2000; Giuffre, L. et al., J. Cell. Biol. 136, 945-956, 1997; Watanabe N., et al., J. Biochem. 125, 826-831, 1999; Li Y F et al., FEBS Lett 444, 201-205, 1999). Consistent with this observation, heparin, HS-GAG and heparin-derived oligosaccharides block L-selectin-dependent adhesion directly (U.S. Pat. No. 5,527,785 to Bevilacqua et al.). Furthermore, short sulfated heparin-derived tetrasaccharides reduced binding of neutrophils to COS cells expressing P-selectin (Nelson R M, et al., Blood 82, 3253-3258, 1993). The multivalent nature of HS may be an important factor in binding L-selectin under flow conditions (Sanders et al, ibid).

As the interactions between GAGs and selectins play an important role in cell-matrix and cell-cell adhesion, the latter are processes involved in certain diseases and inflammatory disorders, modulating these interactions have therapeutic implications.

Bevilacqua et al (U.S. Pat. No. 5,527,785) provide a method of modulating selectin binding in a subject by administering heparin-like oligosaccharides. The oligosaccharides act by binding to L- or P-selectin.

Xie X et al (JBC 275, 34818-25, 2000) described inhibition of L- and P-selectin mediated cell adhesion by sulfated saccharides, including carboxyl-reduced and sulfated heparin. While these molecules have been useful to show the utility of selectin blockers for treating inflammation, each has significant drawbacks as a therapeutic, including short in vivo half-life, high cost, potential immunogenicity, and other possible side effects. A further limitation of these approaches is lack of efficient means to improve the pharmacological properties of these molecules.

In addition, several groups developed small peptides with high affinities for heparin or for heparin-like molecules (i.e., PGs, or other GAGs) (see, for example, U.S. Pat. No. 5,919,761 to Wakefield et al.) to use in a variety of applications for modulating the activities of native GAGs and PGs.

There is still an unmet need to have a non-peptide, small synthetic compounds, which are capable of modulating the functions of GAGs and the interactions between GAGs and GAG effector protein molecules.

U.S. Pat. No. 6,232,320 discloses the use of thieno[2,3-c]pyridines as inhibitors of cell adhesion useful as inhibitors of inflammation. The disclosed compounds are different from the compounds of the present invention as they posses a different heterocyclic system and do not posses sulfonylbenzoylamino group.

Japanese Patent Application JP 2001151779 discloses 4,5,6,7-tetrahydrothieno[2,3-c]pyridines, pharmaceutical compositions, and TNF-α formation inhibitors containing them, also disclosed in Fujita M, et al. (Bioorg. Med. Chem. Lett., 12: 1607-1611, 2002). A related Japanese Patent Application JP 2001151780 discloses novel 4,5,6,7-tetrahydrothieno[2,3-c]pyridines as inhibitors of TNF-alpha synthesis, also disclosed in Fujita et al. (Bioorg. Med. Chem. Lett. 12: 1897-1900, 2002). The two Japanese Patent Application provide different substituents in position 3 of the 4,5,6,7-tetrahdrothieno[2,3-c]pyridine ring (arylcarbonyl in the 2001151779 Application and carboxy or alkoxycarbonyl in the 2001151780 Application). All of these compounds, however, are different from those of the present invention as they do not contain a sulfonylbenzoylamino group as part of the scaffold, an essential feature of the compounds of the present invention.

Balakin et al. (J. Chem. Inf. Comput. Sci. 42: 1332-1342, 2002) describe in silico property-based design of a G-protein coupled receptor (GPCR)-targeted library of compounds. Among the tens of thousands of structures screened in silico, certain compounds from the GPCR-targeted library including a single thieno[2,3-c]pyridine compound were designated the highest scoring structures by the selection criteria applied in that analysis.

SciFinder Scholar database, release 2003, lists 2846 derivatives (as of Dec. 30, 2003) of thieno[2,3-c]pyridine, but no utility is attributed to any of these compounds and no chemical synthesis data are described.

Chemical Diversity Labs Inc. (San Diego, Calif.), a supplier of chemical compounds, released a database named CombiLab Probe Libraries (June 2002 revision; 220,674 compound structures), which lists 438 derivatives of thieno [2,3-c]pyridine, but no utility or chemical synthesis data is described.

I.F. Lab (Kiev, Ukraine), a supplier of chemical compounds, released a database named IF LAB Libraries (July 2003; 77,098 compound structures), which lists 3145 derivatives of thieno[2,3-c]pyridine, but no utility or chemical synthesis data is described. Some of the compounds in Chemical Diversity Labs Inc. database are the same as in I.F. LAB database.

Nowhere in the background art is it taught or suggested that sulfonylbenzoylamino derivatives of thieno[2,3-c]pyridines have beneficial pharmaceutical activities.

SUMMARY OF THE INVENTION

It is an object of some aspects of the present invention to provide pharmaceutical compositions comprising small organic compounds for medical and diagnostic use, wherein the small organic compounds are inhibitors of the interactions between effector cell adhesion molecules (ECAMs), specifically L-selectin and P-selectin, with glycosaminoglycans (GAGs), specifically heparan sulfate glycosaminoglycans (HS-GAGs). Accordingly, these compositions are useful as inhibitors of cell-cell interactions mediated by L-selectin and P-selectin, particularly leukocyte adhesion, migration and infiltration. In addition, the compositions interact directly with HS-GAGs and are therefore useful as inhibitors of any HS-GAG mediated processes and conditions.

According to one aspect, the present invention provides a pharmaceutical composition comprising as an active ingredient a compound of the general formula I:

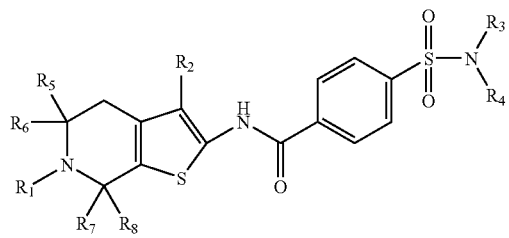

wherein:

$R_1$ is selected from the group consisting of H; straight or branched alkyl of 1-6 carbon atoms; arylalkyl; substituted arylalkyl; cycloalkyl, optionally substituted with alkyl groups; alkanoyl; arylcarbonyl optionally substituted at the aryl group; cycloalkylcarbonyl; alkoxycarbonyl;

$R_2$ is selected from the group consisting of carboxy; cyano; aminocarbonyl; alkylaminocarbonyl; arylaminocarbonyl optionally substituted at the aryl group; dialkylaminocarbonyl wherein each alkyl is straight or branched chain $C_1$-$C_6$ alkyl or both alkyl groups together may form a 3-7 membered saturated, unsaturated or aromatic monocyclic or bicyclic nitrogen containing heterocyclyl, optionally containing one or two additional heteroatoms; allcoxycarbonyl; alkanoyl; cycloalkylcarbonyl; arylcarbonyl optionally substituted on the aryl group, benzothiazol-2-yl;

$R_3$ and $R_4$ are selected from the group consisting of $C_1$-$C_6$ alkyl, optionally substituted by hydroxy, alkoxy, amino or alkylamino, $C_2$-$C_4$ monounsaturated alkenyl, cycloalkyl, aryl, arylmethyl, or $R_3$ and R4 together may form an optionally substituted 5-7 membered saturated, unsaturated or aromatic monocyclic or bicyclic nitrogen containing heterocyclyl, optionally containing one or two additional heteroatoms;

$R_5$, $R_6$, $R_7$ and $R_8$ are selected from the group consisting of H or $C_1$-$C_6$ alkyl, with the proviso that when $R_5$, $R_6$, $R_7$ and $R_8$ are $C_1$-$C_6$ alkyl, $R_1$ is hydrogen;

and pharmaceutically acceptable salts thereof; further comprising a pharmaceutically acceptable diluent or carrier.

According to one embodiment, $R_1$ is selected from the group consisting of methyl, ethyl, 1-methylethyl, phenylmethyl, acetyl, ethoxycarbonyl and $R_5=R_6=R_7=R_8$ are hydrogen.

According to another embodiment, $R_1$ is hydrogen and $R_5=R_6=R_7=R_8$ are hydrogens or methyl groups.

According to yet another embodiment, $R_1=R_5=R_6$ are methyl and $R_7=R_8$ are hydrogens.

According to another embodiment, $R_2$ is selected from the group consisting of cyano, methoxycarbonyl, ethoxycarbonyl, aminocarbonyl, methylaminocarbonyl, dimethylaminocarbonyl, pyrrolidinylcarbonyl, piperidinylcarbonyl, morpholinylcarbonyl, benzothiazol-2-yl.

According to further embodiment, $R_3$ and $R_4$ are selected from the group consisting of methyl, ethyl, propyl, butyl, methoxyethyl, chlorobutyl, cyanoethyl, phenyl, cyclopentyl, cyclohexyl, phenylmethyl, allyl or crotyl, $R_3$ and $R_4$ may be equal or different.

According to another embodiment, $R_3$ and $R_4$ form pyrrolidine, piperidine, 2-methyl, 3-methyl, 4-methyl or 3,5-dimethyl piperidine, perhydroazepine, morpholine, piperazine, 4-methylpiperazine, 3,4-dihydro-2(1H)-isoquinolinyl, 3,4-dihydro-1(2H)quinoline, 1,3,3-trimethyl-6-azabicyclo[3.2.1]oct-6-ane and substituted derivatives thereof. The substituted derivatives include, but are not limited to, piperazinyl-4-carboxylic acid ester, piperidinyl-4-carboxylic acid ester, piperidinyl-3-carboxylic acid ester.

According to certain preferred embodiments, the present invention provides compositions comprising compounds of formula I selected from:

2-[[4-[(ethylbutylamino)sulfonyl]benzoyl]amino]-3-(benzothiazol-2-yl)-6-ethyl-4,5,6,7-tetrahydrothieno[2,3-c]pyridine (Compound no. 5);

2-[[(4-(3,4-dihydro-2(1H)-isoquinolinyl)sulfonyl] benzoyl] amino]-6-(1-methylethyl) -4,5,6,7-tetrahydrothieno[2,3-c]pyridine-3-carboxamide (Compound no.1);

2-[[4-(methylphenylamino)sulfonyl]benzoyl]amino]-6-(1-methylethyl)-4,5,6,7-tetrahydrothieno[2,3-c]pyridine-3-carboxamide;

2-[[4-(3,4-dihydro-1(2H)-quinolinyl)sulfonyl]benzoyl]amino]-4,5,6,7-tetrahydro-5,5,7,7-tetramethylthieno[2,3-c]pyridine-3-carboxamide;

2-[[4-[(diethylamino)sulfonyl]benzoyl]amino]-3-(benzothiazol-2-yl)-6-ethyl-4,5,6,7-tetrahydrothieno[2,3-c]pyridine (Compound no. 11);

2-[[4-(morpholinylsulfonyl)benzoyl]amino]-3-(benzothiazol-2-yl)-6-(1-methylethyl)-4,5,6,7-tetrahydrothieno[2,3-c]pyridine;

2-[[4-(diethylamio)sulfonyl]benzoyl]amino]-4,5,6,7-tetrahydro-5,5,7,7-tetramethylthieno[2,3-c]pyridine-3-carboxylic acid ethyl ester;

2-[[4-(3,4-dihydro-1(2H)-quinolinyl)sulfonyl]benzoyl] amino]-3-(benzothiazol-2-yl)-4,5,6,7-tetrahydro-5,5,7,7-tetramethylthieno[2,3-c]pyridine;

2-[[4-(hexahydro-1H-azepin-1-yl)sulfonyl]benzoyl]amino]-4,5,6,7-tetrahydro-5,5,7,7-tetramethylthieno[2,3-c]pyridine-3-carboxylic acid ethyl ester;

2-[[4-[[4-(methyl)-1-piperazinyl]sulfonyl]benzoyl]amino]-3-(benzothiazol-2-yl)-6-methyl-4,5,6,7-tetrahydrothieno [2,3-c]pyridine;

2-[[4-[(1,3,3-trimethyl-6-azabicyclo[3.2.1]oct-6-yl)sulfonyl]benzoyl]amino]-3-(benzothiazol-2-yl)-6-methyl-4,5,6,7-tetrahydrothieno[2,3-c]pyridine;

2-[[4-[(methylphenylamino)sulfonyl]benzoyl]amino]-3-(benzothiazol-2-yl)-6-methyl-4,5,6,7-tetrahydrothieno[2,3-c]pyridine;

2-[[4-(morpholinylsulfonyl)benzoyl]amino]-3-(benzothiazol-2-yl)-6-methyl-4,5,6,7-tetrahydrothieno[2,3-c]pyridine;

2-[[4-[(diethylamino)sulfonyl]benzoyl]amino]-3-(benzothiazol-2-yl)-4,5,6,7-tetrahydrothieno[2,3-c]pyridine-6-carboxylic acid ethyl ester;

2-[[4-[[4-(3-methyl-1-piperidinyl)]sulfonyl]benzoyl] amino]-3-(benzothiazol-2-yl)-6-methyl-4,5,6,7-tetrahydrothieno[2,3-c]pyridine;

2-[[4-[(diethylamino)sulfonyl]benzoyl]amino]-3-(benzothiazol-2-yl)-6-(phenylmethyl)-4,5,6,7-tetrahydrothieno[2,3-c]pyridine;

2-[[4-[(diethylamino)sulfonyl]benzoyl]amino]-3-(benzothiazol-2-yl)-6-methyl-4,5,6,7-tetrahydrothieno[2,3-c] pyridine;

2-[[4-[[4-(ethoxycarbonyl)-1-piperazinyl]sulfonyl]benzoyl] amino]-4,5,6,7-tetrahydro-5,5,7,7-tetramethylthieno[2,3-c]pyridine-3-carboxamide;

2-[[4-[(cyclohexylmethylamino)sulfonyl]benzoyl]amino]-4,5,6,7-tetrahydro-5,5,7,7-tetramethylthieno[2,3-c]pyridine-3-carboxamide;

2-[[4-[(di-2-propenylamino)sulfonyl]benzoyl]-4,5,6,7-tetrahydro-5,5,7,7-tetramethylthieno[2,3-c]pyridine-3-carboxylic acid methyl ester;

2-[[4-[(di-2-methoxyethylamino))sulfonyl]benzoyl]-4,5,6, 7-tetrahydro-5,5,7,7-tetramethylthieno[2,3-c]pyridine-3-carboxamide;

2-[[4-[(1,3,3-trimethyl-6-azabicyclo[3.2.1.]oct-6-yl)sulfonyl]benzoyl]amino]-6-methyl-4,5,6,7-tetrahydrothieno[2, 3-c]pyridine-3-carboxamide;

2-[[4-[(diethylamino)sulfonyl]benzoyl]amino]-3-(benzothiazol-2-yl)-6-methyl-4,5,6,7-tetrahydrothieno[2,3-c] pyridine;

2-[[4-[(diethylamino)sulfonyl]benzoyl]amino]-3-(benzothiazol-2-yl)-6-(1-methylethyl)-4,5,6,7-tetrahydrothieno[2,3-c]pyridine;

2-[[4-[(di-2-methoxyethylamino)sulfonyl]benzoyl]-amino]-3-(benzothiazol-2-yl)-6-methyl-4,5,6,7-tetrahydrothieno[2,3-c]pyridine;

2-[[4-[(methylphenylamino)sulfonyl]benzoyl]amino]-3-(benzothiazol-2-yl)-6-methyl-4,5,6,7-tetrahydrothieno[2, 3-c]pyridine;

2-[[4-[[4-(ethoxycarbonyl)-1-piperazinyl]sulfonyl]benzoyl] amino]-3-(benzothiazol-2-yl)-6-methyl-4,5,6,7-tetrahydrothieno[2,3-c]pyridine;

2-[[4-[(methylbutylamino)sulfonyl]benzoyl]amino]-6-(1-methylethyl)-4,5,6,7-tetrahydrothieno[2,3-c]pyridine-3-carboxylic acid ethyl ester;

2-[[4-[[4-(ethoxycarbonyl)-1-piperazinyl]sulfonyl]benzoyl]amino]-6-(1-methylethyl)-4,5,6,7-tetrahydrothieno[2,3-c]pyridine-3-carboxylic acid ethyl ester;

2-[[4-(diethylamino)sulfonyl]benzoyl]amino]-4,5,6,7-tetrahydro-5,5,7,7-tetramethylthieno[2,3-c]pyridine-3-carboxamide;

2-[[4-[(methylphenylamino)sulfonyl]benzoyl]amino]-6-ethyl-4,5,6,7-tetrahydrothieno[2,3-c]pyridine-3-carboxylic acid methylamide;

2-[[4-[[ethyl(phenylmethyl)amino]sulfonyl]benzoyl]amino]-6-ethyl-4,5,6,7-tetrahydrothieno[2,3-c]pyridine-3-carboxamide;

2-[[4-[(4-methyl-1-piperazinyl)sulfonyl]benzoyl]amino]-6-ethyl-4,5,6,7-tetrahydrothieno[2,3-c]pyridine-3-carboxamide;

2-[[[(4-(3,4-dihydro-1(2H)-quinolinyl)sulfonyl]benzoyl]amino]-6-ethyl-4,5,6,7-tetrahydrothieno[2,3-c]pyridine-3-carboxylic acid methylamide;

2-[[4-[(4-methyl-1-piperazinyl)sulfonyl]benzoyl]amino]-6-ethyl-4,5,6,7-tetrahydrothieno[2,3-c)pyridine-3-carboxylic acid methylamide;

2-[[4-[(4-methyl-1-piperazinyl)sulfonyl]benzoyl]amino]-3-(benzothiazol-2-yl)-6-ethyl-4,5,6,7-tetrahydrothieno[2,3-c]pyridine;

2-[[4-(diethylamino)sulfonyl]benzoyl]amino]-6-ethyl-4,5,6,7-tetrahydrothieno[2,3-c]pyridine-3-carboxylic acid N-methylamide;

2-[[4-(diethylamino)sulfonyl]benzoyl]amino]-6-ethyl-4,5,6,7-tetrahydrothieno[2,3-c]pyridine-3-carboxylic acid morpholinylamide.

According to currently more preferred embodiments, the pharmaceutical composition of the invention comprise a compound selected from:

2-[[4-[(ethylbutylamino)sulfonyl]benzoyl]amino]-3-(benzothiazol-2-yl)-6-ethyl-4,5,6,7-tetrahydrothieno[2,3-c]pyridine (Compound no. 5);

2-[[4-[(diethylamino)sulfonyl]benzoyl]amino]-3-(benzothiazol-2-yl)-6-ethyl-4,5,6,7-tetrahydrothieno[2,3-c]pyridine (Compound no. 11);

2-[[4-[[ethyl(phenylmethyl)amino]sulfonyl]benzoyl]amino]-6-ethyl-4,5,6,7-tetrahydrothieno[2,3-c]pyridine-3-carboxamide (Compound no. 28);

2-[[4-[(4-methyl-1-piperazinyl)sulfonyl]benzoyl]amino]-6-ethyl-4,5,6,7-tetrahydrothieno[2,3-c]pyridine-3-carboxamide (Compound 29).

According to another embodiment the pharmaceutical compositions of the present invention inhibit the binding of GAGs to GAG-specific-ECAMs.

According to a further embodiment the pharmaceutical compositions of the present invention inhibit the interactions of HS-GAGs with selectins, specifically L-selectin and P-selectin.

According to yet another embodiment, the pharmaceutical compositions of the present invention bind directly to GAGs, specifically HS-GAG.

According to a further embodiment, the pharmaceutical compositions of the present invention inhibit leukocyte and neutrophil infiltration in vivo.

It is to be understood that the present invention does not encompass any compounds or pharmaceutical compositions thereof for which such a pharmaceutical activity has been disclosed. Explicitly excluded is the compound 2-[[4-[(1,3,3-trimethyl-6-azabicyclo[3.2.1.]oct-6-yl)sulfonyl]benzoyl]amino]-6-ethyl-4,5,6,7-tetrahydrothieno[2,3-c]pyridine-3-carboxylic acid ethyl ester.

According to another aspect the present invention discloses certain novel compounds and these are claimed as such. According to one embodiment, the present invention provides a small organic compound having the formula 2-[[4-[[ethyl(phenylmethyl)amino]sulfonyl]benzoyl]amino]-6-ethyl-4,5,6,7-tetrahydrothieno[2,3-c]pyridine-3-carboxamide (Compound No. 28).

According to another embodiment, the present invention provides a small organic compound having the formula 2-[[4-[(4-methyl-1-piperazinyl)sulfonyl]benzoyl]amino]-6-ethyl-4,5,6,7-tetrahydrothieno[2,3-c]pyridine-3-carboxamide (Compound No. 29).

According to yet another aspect, the present invention provides a method for inhibiting cell adhesion and cell migration in vitro comprising the step of exposing the cells to a pharmaceutical composition according to the invention in an amount sufficient to inhibit binding of GAGs to GAG specific ECAMs.

According to yet other aspect, the present invention provides a method for the treatment or prevention of diseases and disorders related to cell adhesion and cell migration mediated by GAG-ECAM interactions, comprising the step of administering to a subject in need thereof a therapeutically effective amount of a pharmaceutical composition comprising a compound of the general formula I:

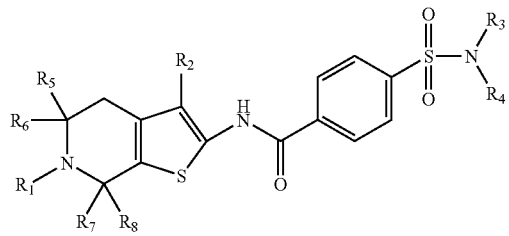

wherein:

$R_1$ is selected from the group consisting of H; straight or branched alkyl of 1-6 carbon atoms; arylalkyl; substituted arylalkyl; cycloalkyl, optionally substituted with alkyl groups; alkanoyl; arylcarbonyl optionally substituted at the aryl group; cycloalkylcarbonyl; alkoxycarbonyl;

$R_2$ is selected from the group consisting of carboxy; cyano; aminocarbonyl; alkylaminocarbonyl; arylaminocarbonyl optionally substituted at the aryl group; dialkylaminocarbonyl wherein each alkyl is straight or branched chain $C_1$-$C_6$ alkyl or both alkyl groups together may form a 3-7 membered saturated, unsaturated or aromatic monocyclic or bicyclic nitrogen containing heterocyclyl, optionally containing one or two additional heteroatoms; alkoxycarbonyl; alkanoyl; cycloalkylcarbonyl; arylcarbonyl optionally substituted on the aryl group, benzothiazol-2-yl;

$R_3$ and $R_4$ are selected from the group consisting of $C_1$-$C_6$ alkyl, optionally substituted by hydroxy, alkoxy, amino or alkylamino, $C_2$-$C_4$ monounsaturated alkenyl, cycloalkyl, aryl, arylmethyl, or $R_3$ and $R_4$ together may form an optionally substituted 5-7 membered saturated, unsaturated or aromatic monocyclic or bicyclic nitrogen containing heterocyclyl, optionally containing one or two additional heteroatoms;

R$_5$, R$_6$, R$_7$ and R$_8$ are selected from the group consisting of H or C$_1$-C$_6$ alkyl, with the proviso that when R$_5$, R$_6$, R$_7$ and R$_8$ are C$_1$-C$_6$ alkyl, R$_1$ is hydrogen;

and pharmaceutically acceptable salts thereof; further comprising a pharmaceutically acceptable diluent or carrier.

According to certain preferred embodiments, the method for the treatment or prevention of diseases and disorders related to cell adhesion and cell migration mediated by GAG-ECAM interactions comprise the step of administering to a subject in need thereof a therapeutically effective amount of a pharmaceutical composition according to the invention comprising as an active ingredient a compound of formula I selected from:

2-[[4-[(ethylbutylamino)sulfonyl]benzoyl]amino]-3-(benzothiazol-2-yl)-6-ethyl-4,5,6,7-tetrahydrothieno[2,3-c]pyridine (Compound no. 5);

2-[[(4-(3,4-dihydro-2(1H)-isoquinolinyl)sulfonyl]benzoyl]amino]-6-(1-methylethyl)-4,5,6,7-tetrahydrothieno[2,3-c]pyridine-3-carboxamide (Compound no.1);

2-[[4-(methylphenylamino)sulfonyl]benzoyl]amino]-6-(1-methylethyl)-4,5,6,7-tetrahydrothieno[2,3-c]pyridine-3-carboxamide;

2-[[4-(3,4-dihydro-1(2H)-quinolinyl)sulfonyl]benzoyl]amino]-4,5,6,7-tetrahydro-5,5,7,7-tetramethylthieno[2,3-c]pyridine-3-carboxamide;

2-[[4-[(diethylamino)sulfonyl]benzoyl]amino]-3-(benzothiazol-2-yl)-6-ethyl-4,5,6,7-tetrahydrothieno[2,3-c]pyridine (Compound no. 11);

2-[[4-(morpholinylsulfonyl)benzoyl]amino]-3-(benzothiazol-2-yl)-6-(1-methylethyl)-4,5,6,7-tetrahydrothieno[2,3-c]pyridine;

2-[[4-(diethylamino)sulfonyl]benzoyl]amino]-4,5,6,7-tetrahydro-5,5,7,7-tetramethyl thieno[2,3-c]pyridine-3-carboxylic acid ethyl ester;

2-[[4-(3,4-dihydro-1(2H)-quinolinyl)sulfonyl]benzoyl]amino]-3-(benzothiazol-2-yl)-4,5,6,7-tetrahydro-5,5,7,7-tetramethylthieno[2,3-c]pyridine;

2-[[4-(hexahydro-1H-azepin-1-yl)sulfonyl]benzoyl]amino]-4,5,6,7-tetrahydro-5,5,7,7-tetramethylthieno[2,3-c]pyridine-3-carboxylic acid ethyl ester;

2-[[4-[[4-(methyl)-1-piperazinyl]sulfonyl]benzoyl]amino]-3-(benzothiazol-2-yl)-6-methyl-4,5,6,7-tetrahydrothieno[2,3-c]pyridine;

2-[[4-[(1,3,3-trimethyl-6-azabicyclo[3.2.1]oct-6-yl)sulfonyl]benzoyl]amino]-3-(benzothiazol-2-yl)-6-methyl-4,5,6,7-tetrahydrothieno[2,3-c]pyridine;

2-[[4-[(methylphenylamino)sulfonyl]benzoyl]amino]-3-(benzothiazol-2-yl)-6-methyl-4,5,6,7-tetrahydrothieno[2,3-c]pyridine;

2-[[4-(morpholinylsulfonyl)benzoyl]amino]-3-(benzothiazol-2-yl)-6-methyl-4,5,6,7-tetrahydrothieno[2,3-c]pyridine;

2-[[4-[(diethylamino)sulfonyl]benzoyl]amino]-3-(benzothiazol-2-yl)-4,5,6,7-tetrahydrothieno[2,3-c]pyridine-6-carboxylic acid ethyl ester;

2-[[4-[[4-(3-methyl-1-piperidinyl)]sulfonyl]benzoyl]amino]-3-(benzothiazol-2-yl)-6-methyl-4,5,6,7-tetrahydrothieno[2,3-c]pyridine;

2-[[4-[(diethylamino)sulfonyl]benzoyl]amino]-3-(benzothiazol-2-yl)-6-(phenylmethyl)-4,5,6,7-tetrahydrothieno[2,3-c]pyridine;

2-[[4-[(diethylamino)sulfonyl]benzoyl]amino]-3-(benzothiazol-2-yl)-6-methyl-4,5,6,7-tetrahydrothieno[2,3-c]pyridine;

2-[[4-[[4-(ethoxycarbonyl)-1-piperazinyl]sulfonyl]benzoyl]amino]-4,5,6,7-tetrahydro-5,5,7,7-tetramethylthieno[2,3-c]pyridine-3-carboxamide;

2-[[4-[(cyclohexylmethylamino)sulfonyl]benzoyl]amino]-4,5,6,7-tetrahydro-5,5,7,7-tetramethylthieno[2,3-c]pyridine-3-carboxamide;

2-[[4-[(di-2-propenylamino)sulfonyl]benzoyl]-4,5,6,7-tetrahydro-5,5,7,7-tetramethylthieno[2,3-c]pyridine-3-carboxylic acid methyl ester;

2-[[4-[(di-2-methoxyethylamino)]sulfonyl]benzoyl]-4,5,6,7-tetrahydro-5,5,7,7-tetramethylthieno[2,3-c]pyridine-3-carboxamide;

2-[[4-[(1,3,3-trimethyl-6-azabicyclo[3.2.1.]oct-6-yl)sulfonyl]benzoyl]amino]-6-methyl-4,5,6,7-tetrahydrothieno[2,3-c]pyridine-3-carboxamide;

2-[[4-[(diethylamino)sulfonyl]benzoyl]amino]-3-(benzothiazol-2-yl)-6-methyl-4,5,6,7-tetrahydrothieno[2,3-c]pyridine;

2-[[4-[(diethylamino)sulfonyl]benzoyl]amino]-3-(benzothiazol-2-yl)-6-(1-methylethyl)-4,5,6,7-tetrahydrothieno[2,3-c]pyridine;

2-[[4-[(di-2-methoxyethylamino)sulfonyl]benzoyl]-amino]-3-(benzothiazol-2-yl)-6-methyl-4,5,6,7-tetrahydrothieno[2,3-c]pyridine;

2-[[4-[(methylphenylamino)sulfonyl]benzoyl]amino]-3-(benzothiazol-2-yl)-6-methyl-4,5,6,7-tetrahydrothieno[2,3-c]pyridine;

2-[[4-[[4-(ethoxycarbonyl)-1-piperazinyl]sulfonyl]benzoyl]amino]-3-(benzothiazol-2-yl)-6-methyl-4,5,6,7-tetrahydrothieno[2,3-c]pyridine;

2-[[4-[(methylbutylamino)sulfonyl]benzoyl]amino]-6-(1-methylethyl)-4,5,6,7-tetrahydrothieno[2,3-c]pyridine-3-carboxylic acid ethyl ester;

2-[[4-[[4-(ethoxycarbonyl)-1-piperazinyl]sulfonyl]benzoyl]amino]-6-(1-methylethyl)-4,5,6,7-tetrahydrothieno[2,3-c]pyridine-3-carboxylic acid ethyl ester;

2-[[4-(diethylamino)sulfonyl]benzoyl]amino]-4,5,6,7-tetrahydro-5,5,7,7-tetramethylthieno[2,3-c]pyridine-3-carboxamide;

2-[[4-[(methylphenylamino)sulfonyl]benzoyl]amino]-6-ethyl-4,5,6,7-tetrahydrothieno[2,3-c]pyridine-3-carboxylic acid methylamide;

2-[[4-[[ethyl(phenylmethyl)amino]sulfonyl]benzoyl]amino]-6-ethyl-4,5,6,7-tetrahydrothieno[2,3-c]pyridine-3-carboxamide;

2-[[4-[(4-methyl-1-piperazinyl)sulfonyl]benzoyl]amino]-6-ethyl-4,5,6,7-tetrahydrothieno[2,3-c]pyridine-3-carboxamide;

2-[[(4-(3,4-dihydro-1(2H)-quinolinyl)sulfonyl]benzoyl]amino]-6-ethyl-4,5,6,7-tetrahydrothieno[2,3-c]pyridine-3-carboxylic acid methylamide;

2-[[4-[(4-methyl-1-piperazinyl)sulfonyl]benzoyl]amino]-6-ethyl-4,5,6,7-tetrahydrothieno[2,3-c]pyridine-3-carboxylic acid methylamide;

2-[[4-[(4-methyl-1-piperazinyl)sulfonyl]benzoyl]amino]-3-(benzothiazol-2-yl)-6-ethyl-4,5,6,7-tetrahydrothieno[2,3-c]pyridine;

2-[[4-(diethylamino)sulfonyl]benzoyl]amino]-6-ethyl-4,5,6,7-tetrahydrothieno[2,3-c]pyridine-3-carboxylic acid N-methylamide;

2-[[4-(diethylamino)sulfonyl]benzoyl]amino]-6-ethyl-4,5,6,7-tetrahydrothieno[2,3-c]pyridine-3-carboxylic acid morpholinylamide.

According to currently more preferred embodiments, the method for the treatment or prevention of diseases and disorders related to cell adhesion and cell migration mediated by GAG-ECAM interactions comprise administering to a subject in need thereof a therapeutically effective amount of a pharmaceutical composition comprising as an active ingredient a compound of formula I selected from:

2-[[4-[(ethylbutylamino)sulfonyl]benzoyl]amino]-3-(benzothiazol-2-yl)-6-ethyl-4,5,6,7-tetrahydrothieno[2,3-c]pyridine (Compound no. 5);

2-[[4-[(diethylamino)sulfonyl]benzoyl]amino]-3-(benzothiazol-2-yl)-6-ethyl-4,5,6,7-tetrahydrothieno[2,3-c]pyridine (Compound no. 11);

2-[[4-[[ethyl(phenylmethyl)amino]sulfonyl]benzoyl]amino]-6-ethyl-4,5,6,7-tetrahydrothieno[2,3-c]pyridine-3-carboxamide (Compound no. 28);

2-[[4-[(4-methyl-1-piperazinyl)sulfonyl]benzoyl]amino]-6-ethyl-4,5,6,7-tetrahydrothieno[2,3-c]pyridine-3-carboxamide (Compound no. 29).

According to one embodiment, the invention provides a method for treatment or prevention of diseases or disorders mediated by GAG-ECAM interactions, wherein the GAGs are selected from the group consisting of heparan sulfate (HS-GAG), heparin, chondroitin sulfate, dermatan sulfate, keratan sulfate, and derivatives and fragments thereof. According to a currently preferred embodiment, the GAG is HS-GAG.

According to yet another embodiment, the invention provides a method for treatment or prevention of diseases or disorders mediated by GAG-ECAM interactions, wherein the GAG specific ECAMs are selected from the group consisting of selecting, integrins, fibronectin, and cytokines. According to a currently preferred embodiment, the GAG specific ECAMs are selected from the group consisting of L-selectin and P-selectin.

According to another embodiment, the disease or disorder mediated by GAG-ECAM interactions is selected from inflammatory processes or disorders, autoimmune processes or diseases, platelet-mediated pathologies, tumor metastasis, viral diseases, coagulation disorders, atherosclerosis, amyloid disorders, and kidney diseases.

According to another embodiment, the inflammatory processes or disorders mediated by GAG-ECAM interactions are exemplified by, but not restricted to, septic shock, post-ischemic leukocyte-mediated tissue damage, frost-bite injury or shock, acute leukocyte-mediated lung injury, acute pancreatitis, nephritis, asthma, traumatic shock, stroke, traumatic brain injury, nephritis, acute and chronic inflammation, including atopic dermatitis, psoriasis, uveitis, retinitis, and inflammatory bowel disease.

According to a currently preferred embodiment, the invention provides a method for the prevention or treatment of inflammatory bowel disease comprising the step of administering to a subject in need thereof a therapeutically effective amount of a pharmaceutical composition comprising a thieno[2,3-c]pyridine compound of the formula 2-[[4-[(diethylamino)sulfonyl]benzoyl]amino]-3-(benzothiazol-2-yl)-6-ethyl-4,5,6,7-tetrahydrothieno[2,3-c]pyridine (Compound no. 11) and a pharmaceutically acceptable salt thereof, further comprising a pharmaceutically acceptable diluent or carrier.

According to yet another embodiment, the autoimmune diseases mediated by GAG-ECAM interactions are exemplified by, but not restricted to, rheumatoid arthritis and multiple sclerosis.

According to a currently preferred embodiment, the invention provides a method for the prevention or treatment of multiple sclerosis comprising the step of administering to a subject in need thereof a therapeutically effective amount of a pharmaceutical composition comprising as an active ingredient thieno[2,3-c]pyridine compound 2-[[4-[(diethylamino)sulfonyl]benzoyl]amino]-3-(benzothiazol-2-yl)-6-ethyl-4,5,6,7-tetrahydrothieno[2,3-c]pyridine (Compound no. 11) and a pharmaceutically acceptable salt thereof; further comprising a pharmaceutically acceptable carrier or diluent.

According to yet further embodiment, the diseases or disorders mediated by GAG-ECAM interactions include those mediated by cell-cell, cell-virus, cell-matrix, and cell-protein interactions, exemplified by, but not restricted to, virus attachment to a cell, cell adhesion, platelet aggregation, lymphocyte adhesion and migration, and amyloid fibril formation.

According to yet further embodiment, the invention provides a method for the treatment or prevention of diseases and disorders mediated by GAGs, specifically HS-GAG. The diseases and disorders mediated by GAGs are selected from the group consisting of amyloid disorders such as Alzheimer's disease and type II diabetes; viral diseases such as hepatitis C and B, influenza, rhinovirus infections, cytomegalovirus infections, AIDS, and respiratory syncytial virus infections; bacterial infections and malaria; kidney diseases; cancer such as leukemia; and coagulation disorders.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Definitions

Figure 1:
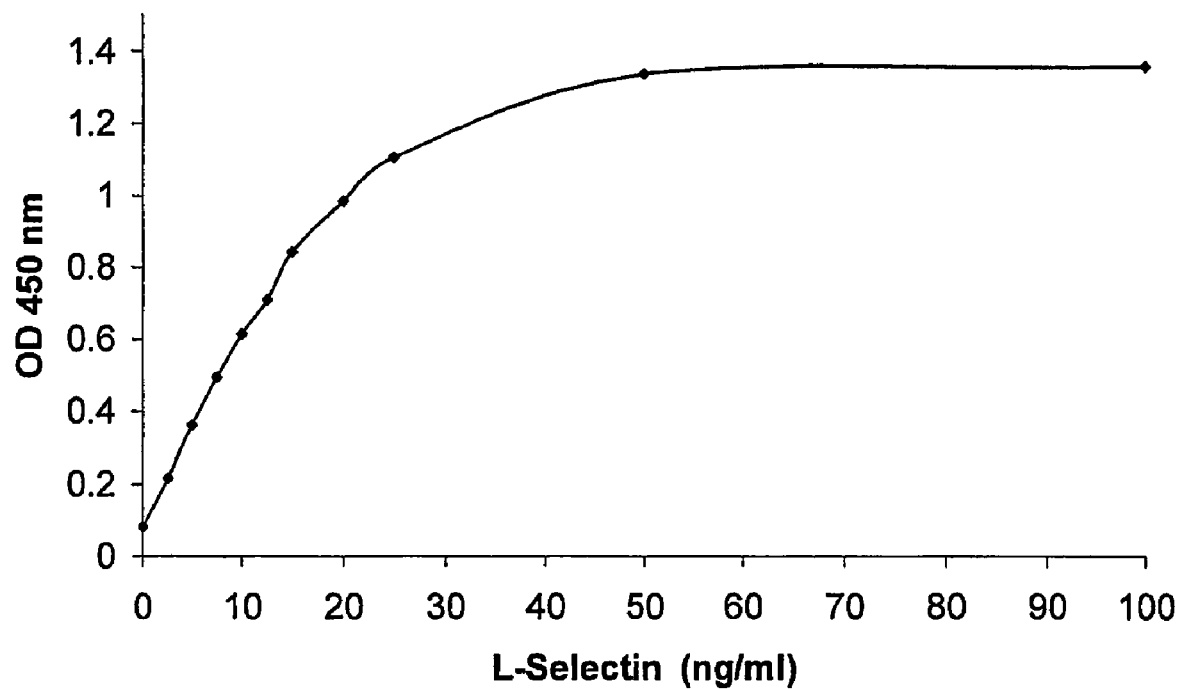
FIG. 1 shows L-selectin binding to immobilized heparin.

In accordance with the present invention and as used herein, the following terms are defined with the following meanings, unless explicitly stated otherwise.

The term "compound" refers to small organic molecule having a molecular weight less than 1500 Daltons and preferably between 300 to 1200 Daltons.

The term "GAG" refers to glycosaminoglycans, including heparan sulfate (HS-GAG), heparin, chondroitin sulfate, dermatan sulfate and keratan sulfate. It includes the GAG chains of proteoglycans such as heparan sulfate proteoglycan or chondroitin sulfate proteoglycan. It includes fragments of GAG produced chemically or enzymatically. It also includes derivatives of GAG, which may be produced by chemical or enzymatic means as known in the art. GAG may be free or attached to a linker, support, cell or a protein. GAGs may be crude or purified from organs, tissues or cells.

The term "HS-GAG" refers to heparan sulfate glycosaminoglycan. It includes fragments of heparan sulfate such as those that may be produced chemically, enzymatically or during purification. It includes the HS-GAG chains of proteoglycans such as heparan sulfate proteoglycans. HS-GAG may be free or attached to a linker, support, cell or protein, or otherwise chemically or enzymatically modified. HS-GAGs may be crude or purified from organs, tissues or cells.

"HS-PG" refers to heparan sulfate proteoglycans.

"Heparin" is polysulfated polysaccharide, with no protein associated with it. As used herein, heparin refers to heparin prepared from different organs or species such as from porcine intestinal mucosa. The invention encompasses heparins with various molecular weights including low molecular weight heparins, such as commercially available Fraxiparin, and other heparin derivatives, prepared or modified by chemical or enzymatic reactions as known in the art.

"GAG Derivatives" or "ECAM Derivatives" consist of products derived from GAGS or ECAMS, respectively, made by one or more chemical or enzymatic modifications. The modifications are designed to modify the activity of relevant groups of the molecules.

"Oligosaccharide fragments" or "GAG Derived Oligosaccharides" are products derived from GAGs by controlled cleavage and preferably purified after cleavage.

The terms "L-selectin/IgG" and "P-selectin/IgG" refer to a selectin chimera molecule, in which an N-terminal portion of the selectin comprising the binding domain is fused to an IgG Fc region (Aruffo et al., Cell 67:35, 1991; and Foxall et al. J. Cell Biol. 117:895, 1992).

The term "GAG specific ECAM" means an effector cell adhesion molecule and refers to a carbohydrate-binding protein molecule involved in mediating cell adhesion, cell-cell and cell-matrix interaction and having a GAG binding domain. Examples of ECAMs are selectins such as L-selectin, P-selectin, integrins, fibronectin, cytokines, and the like. The term "GAG specific ECAM" also includes mutant ECAMs, protein domains, polypeptides or peptides derived from ECAMs, chemical or enzymatic derivatives of ECAMs, and the like, so long as the mutant ECAMs, protein domains, polypeptides, peptides and derivatives of ECAMs retain the capability to bind GAGs.

The term "inhibitor Compound" refers to a small organic compound that inhibits, modulates or reverses the function of a GAG. For instance, inhibitor Compound may inhibit interaction (binding) between two molecules: (1) a GAG, exemplified by, but not restricted to, heparin, or HS-GAG and (2) a GAG specific ECAM, exemplified by, but not restricted to, L-selectin, P-selectin, or integrin.

The terms "inflammation", "inflammatory diseases", "inflammatory condition" or "inflammatory process" are meant as physiological or pathological conditions, which are accompanied by an inflammatory response. Such conditions include, but are not limited to, sepsis, ischemia-reperfusion injury, Crohn's disease, arthritis, multiple sclerosis, cardiomyopathic disease, colitis, infectious meningitis, encephalitis, acute respiratory distress syndrome, organ/tissue transplant rejection (such as skin, kidney, heart, lung, liver, bone marrow, cornea, pancreas, small bowel), an infection, dermatitis, stroke, traumatic brain injury, inflammatory bowel disease, and autoimmune diseases.

The term "treatment" or "treating" is intended to include the administration of the compound of the invention to a subject for purposes which may include prophylaxis, amelioration, prevention or cure of disorders mediated by cell adhesion or cell migration events, specifically selectin adhesion events, more specifically L-selectin and P-selectin-mediated adhesion events. Such treatment need not necessarily completely ameliorate the inflammatory response or other responses related to the specific disorder. Further, such treatment may be used in conjunction with other traditional treatments for reducing the disease or disorder condition known to those of skill in the art.

The methods of the invention may be provided as a "preventive" treatment before detection of, for example, an inflammatory state, so as to prevent the disorder from developing in patients at high risk for the same, such as, for example, transplant patients.

The term "cancer" refers to various cancer-associated conditions including metastasis, tumor growth, and angiogenesis. According to the invention, cancer is exemplified by leukemias.

As used through this specification and the appended claims, the singular forms "a", "an" and "the" include the plural unless the context clearly dictates otherwise. Thus, for example, reference to "a compound" includes mixtures of such compounds, reference to "a P-selectin", or "an L-selectin" includes reference to respective mixtures of such molecules, reference to "the formulation" or "the method" includes one or more formulations, methods and/or steps of the type described herein and/or which will become apparent to those persons skilled in the art upon reading this disclosure.

Pharmaceutical Compositions

The present invention relates to pharmaceutical compositions comprising as an active ingredient at least one compound capable of inhibiting the interactions of glycosaminoglycans (GAGs), particularly heparan sulfate glycosaminoglycans (HS-GAG) with effector cell adhesion molecules (ECAMs), particularly GAG-specific ECAMs, specifically L-selectin and P-selectin.

According to some aspects the present invention provides pharmaceutical compositions comprising as an active ingredient a compound having the general formula I:

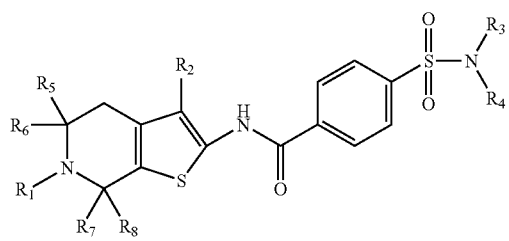

wherein:

$R_1$ is selected from the group consisting of H; straight or branched alkyl of 1-6 carbon atoms; arylalkyl; substituted arylalkyl; cycloalkyl, optionally substituted with alkyl groups; alkanoyl; arylcarbonyl optionally substituted at the aryl group; cycloalkylcarbonyl; alkoxycarbonyl;

$R_2$ is selected from the group consisting of carboxy; cyano; aminocarbonyl; alkylaminocarbonyl; arylaminocarbonyl optionally substituted at the aryl group; dialkylaminocarbonyl wherein each alkyl is straight or branched chain $C_1$-$C_6$ alkyl or both alkyl groups together may form a 3-7 membered saturated, unsaturated or aromatic monocyclic or bicyclic nitrogen containing heterocyclyl, optionally containing one or two additional heteroatoms; alkoxycarbonyl; alkanoyl; cycloalkylcarbonyl; arylcarbonyl optionally substituted on the aryl group, benzothiazol-2-yl;

$R_3$ and $R_4$ are selected from the group consisting of $C_1$-$C_6$ alkyl, optionally substituted by hydroxy, alkoxy, amino or alkylamino, $C_2$-$C_4$ monounsaturated alkenyl, cycloalkyl, aryl, arylmethyl, or $R_3$ and $R_4$ together may form an optionally substituted 5-7 membered saturated, unsaturated or aromatic monocyclic or bicyclic nitrogen containing heterocyclyl, optionally containing one or two additional heteroatoms;

$R_5$, $R_6$, $R_7$ and $R_8$ are selected from the group consisting of H or $C_1$-$C_6$ alkyl, with the proviso that when $R_5$, $R_6$, $R_7$ and $R_8$ are $C_1$-$C_6$ alkyl, $R_1$ is hydrogen;

and pharmaceutically acceptable salts thereof; further comprising a pharmaceutically acceptable diluent or carrier.

According to one embodiment, $R_1$ is selected from the group consisting of methyl, ethyl, 1-methylethyl, phenylmethyl, acetyl, ethoxycarbonyl and $R_5$=$R_6$=$R_7$=$R_8$ are hydrogen.

According to another embodiment, $R_1$ is hydrogen and $R_5$=$R_6$=$R_7$=$R_8$ are hydrogens or methyl groups.

According to yet another embodiment, $R_1$=$R_5$=$R_6$ are methyl and $R_7$=$R_8$ are hydrogens.

According to a further embodiment $R_2$ is selected from the group consisting of cyano, methoxycarbonyl, ethoxycarbonyl, aminocarbonyl, methylaminocarbonyl, dimethylaminocarbonyl, pyrrolidinylcarbonyl, piperidinylcarbonyl, morpholinylcarbonyl, benzothiazol-2-yl.

According to another embodiment, $R_3$ and $R_4$ are selected from the group consisting of methyl, ethyl, propyl, butyl, methoxyethyl, chlorobutyl, cyanoethyl, phenyl, cyclopentyl, cyclohexyl, phenylmethyl, allyl or crotyl, $R_3$ and $R_4$ may be equal or different.

According to another embodiment, $R_3$ and $R_4$ form pyrrolidine, piperidine, 2-methyl, 3-methyl, 4-methyl or 3,5-dimethyl piperidine, perhydroazepine, morpholine, piperazine, 4-methylpiperazine, 3,4-dihydro-2(1H)-isoquinolinyl, 3,4-dihydro-1(2H)quinoline, 1,3,3-trimethyl-6-azabicyclo [3.2. 1]oct-6-ane and substituted derivatives thereof. The substituted derivatives include, but are not limited to, piperazinyl-4-caboxylic acid ester, piperidinyl-4-carboxylic acid ester, piperidinyl-3-carboxylic acid ester.

According to one embodiment, the preferred pharmaceutical compositions of the invention comprise as an active ingredient a compound according to formula I selected from:

2-[[4-[(ethylbutylamino)sulfonyl]benzoyl]amino]-3-(benzothiazol-2-yl)-6-ethyl-4,5,6,7-tetrahydrothieno[2,3-c] pyridine (Compound no. 5);

2-[[(4-(3,4-dihydro-2(1H)-isoquinolinyl)sulfonyl]benzoyl] amino]-6-(1-methylethyl)-4,5,6,7-tetrahydrothieno[2,3-c] pyridine-3-carboxamide (Compound no. 1);

2-[[4-(methylphenylamino)sulfonyl]benzoyl]amino]-6-(1-methylethyl)-4,5,6,7-tetrahydrothieno[2,3-c]pyridine-3-carboxamide;

2-[[4-(3,4-dihydro-2(1H)-isoquinolinyl)sulfonyl]benzoyl] amino]-4,5,6,7-tetrahydro-5,5,7,7-tetramethylthieno[2,3-c]pyridine-3-carboxamide;

2-[[4-[(diethylamino)sulfonyl]benzoyl]amino]-3-(benzothiazol-2-yl)-6-ethyl-4,5,6,7-tetrahydrothieno[2,3-c] pyridine (Compound 11);

2-[[4-(morpholinylsulfonyl)benzoyl]amino]-3-(benzothiazol-2-yl)-6-(1-methylethyl)-4,5,6,7-tetrahydrothieno[2,3-c]pyridine;

2-[[4-(diethylamino)sulfonyl]benzoyl]amino]-4,5,6,7-tetrahydro-5,5,7,7-tetramethylthieno[2,3-c]pyridine-3-carboxylic acid ethyl ester;

2-[[4-(3,4-dihydro-1(2H)-quinolinyl)sulfonyl]benzoyl] amino]-3-(benzothiazol-2-yl)-4,5,6,7-tetrahydro-5,5,7,7-tetramethylthieno[2,3-c]pyridine;

2-[[4-(hexahydro-1H-azepin-1-yl)sulfonyl]benzoyl]amino]-4,5,6,7-tetrahydro-5,5,7,7-tetramethylthieno[2,3-c]pyridine-3-carboxylic acid ethyl ester;

2-[[4-[[4-(methyl)-1-piperazinyl]sulfonyl]benzoyl]amino]-3-(benzothiazol-2-yl)-6-methyl-4,5,6,7-tetrahydrothieno [2,3-c]pyridine;

2-[[4-[(1,3,3-trimethyl-6-azabicyclo[3.2.1]oct-6-yl)sulfonyl]benzoyl]amino]-3-(benzothiazol-2-yl)-6-methyl-4,5, 6,7-tetrahydrothieno[2,3-c]pyridine;

2-[[4-[(methylphenylamino)sulfonyl]benzoyl]amino]-3-(benzothiazol-2-yl)-6-methyl-4,5,6,7-tetrahydrothieno[2, 3-c]pyridine;

2-[[4-(morpholinylsulfonyl)benzoyl]amino]-3-(benzothiazol-2-yl)-6-methyl-4,5,6,7-tetrahydrothieno[2,3-c]pyridine.

2-[[4-[(diethylamino)sulfonyl]benzoyl]amino]-3-(benzothiazol-2-yl)-4,5,6,7-tetrahydrothieno[2,3-c]pyridine-6-carboxylic acid ethyl ester;

2-[[4-[[4-(3-methyl-1-piperidinyl)]sulfonyl]benzoyl] amino]-3-(benzothiazol-2-yl)-6-methyl4,5,6,7-tetrahydrothieno[2,3-c]pyridine;

2-[[4-[(diethylamino)sulfonyl]benzoyl]amino]-3-(benzothiazol-2-yl)-6-(phenylmethyl)-4,5,6,7-tetrahydrothieno[2,3-c]pyridine;

2-[[4-[(diethylamino)sulfonyl]benzoyl]amino]-3-(benzothiazol-2-yl)-6-methyl4,5,6,7-tetrahydrothieno[2,3-c] pyridine;

2-[[4-[[4-(ethoxycarbonyl)-1-piperazinyl]sulfonyl]benzoyl] amino]-4,5,6,7-tetrahydro-5,5,7,7-tetramethylthieno[2,3-c]pyridine-3-carboxamide;

2-[[4-[(cyclohexylmethylamino)sulfonyl]benzoyl]amino]-4,5,6,7-tetrahydro-5,5,7,7-tetramethylthieno[2,3-c]pyridine-3-carboxamide;

2-[[4-[(di-2-propenylamino)sulfonyl]benzoyl]-4,5,6,7-tetrahydro-5,5,7,7-tetramethylthieno[2,3-c]pyridine-3-carboxylic acid methyl ester;

2-[[4-[(di-2-methoxyethylamino)]sulfonyl]benzoyl]-4,5,6, 7-tetrahydro-5,5,7,7-tetramethylthieno[2,3-c]pyridine-3-carboxamide;

2-[[4-[(1,3,3-trimethyl-6-azabicyclo[3.2.1.]oct-6-yl)sulfonyl]benzoyl]amino]-6-methyl-4,5,6,7-tetrahydrothieno[2, 3-c]pyridine-3-carboxamide;

2-[[4-[(diethylamio)sulfonyl]benzoyl]amino]-3-(benzothiazol-2-yl)-6-methyl-4,5,6,7-tetrahydrothieno[2,3-c]pyridine;

2-[[4-[(diethylamino)sulfonyl]benzoyl]amino]-3-(benzothiazol-2-yl)-6-(1-methylethyl)-4,5,6,7-tetrahydrothieno[2,3-c]pyridine;

2-[[4-[(di-2-methoxyethylamino)sulfonyl]benzoyl]-amino]-3-(benzothiazol-2-yl)-6-methyl-4,5,6,7-tetrahydrothieno [2,3-c]pyridine;

2-[[4-[(methylphenylamino)sulfonyl]benzoyl]amino]-3-(benzothiazol-2-yl)-6-methyl-4,5,6,7-tetrahydrothieno[2,3-c]pyridine;

2-[[4-[[4-(ethoxycarbonyl)-1-piperazinyl]sulfonyl]benzoyl]amino]-3-(benzothiazol-2-yl)-6-methyl-4,5,6,7-tetrahydrothieno[2,3-c]pyridine;

2-[[4-[(methylbutylamino)sulfonyl]benzoyl]amino]-6-(1-methylethyl)-4,5,6,7-tetrahydrothieno[2,3-c]pyridine-3-carboxylic acid ethyl ester;

2-[[4-[[4-(ethoxycarbonyl)-1-piperazinyl]sulfonyl]benzoyl]amino]-6-(1-methylethyl)-4,5,6,7-tetrahydrothieno[2,3-c]pyridine-3-carboxylic acid ethyl ester;

2-[[4-(diethylamino)sulfonyl]benzoyl]amino]-4,5,6,7-tetrahydro-5,5,7,7-tetramethylthieno[2,3-c]pyridine-3-carboxamide;

2-[[4-[(methylphenylamino)sulfonyl]benzoyl]amino]-6-ethyl-4,5,6,7-tetrahydrothieno[2,3-c]pyridine-3-carboxylic acid methylamide;

2-[[4-[[ethyl(phenylmethyl)amino]sulfonyl]benzoyl]amino]-6-ethyl-4,5,6,7-tetrahydrothieno[2,3-c]pyridine-3-carboxamide;

2-[[4-[(4-methyl-1-piperazinyl)sulfonyl]benzoyl]amino]-6-ethyl-4,5,6,7-tetrahydrothieno[2,3-c]pyridine-3-carboxamide;

2-[[[(4-(3,4-dihydro-1(2H)-quinolinyl)sulfonyl]benzoyl]amino]-6-ethyl-4,5,6,7-tetrahydrothieno[2,3-c]pyridine-3-carboxylic acid methylamide;

2-[[4-[(4-methyl-1-piperazinyl)sulfonyl]benzoyl]amino]-6-ethyl-4,5,6,7-tetrahydrothieno[2,3-c]pyridine-3-carboxylic acid methylamide;

2-[[4-[(4-methyl-1-piperazinyl)sulfonyl]benzoyl]amino]-3-(benzothiazol-2-yl)-6-ethyl-4,5,6,7-tetrahydrothieno[2,3-c]pyridine;

2-[[4-(diethylamino)sulfonyl]benzoyl]amino]-6-ethyl-4,5,6,7-tetrahydrothieno[2,3-c]pyridine-3-carboxylic acid N-methylamide;

2-[[4-(diethylamino)sulfonyl]benzoyl]amino]-6-ethyl-4,5,6,7-tetrahydrothieno[2,3-c]pyridine-3-carboxylic acid morpholinylamide.

According to another embodiment, the more preferred pharmaceutical compositions of the invention comprise as an active ingredient a compound of formula I selected from:

2-[[4-[(ethylbutylamino)sulfonyl]benzoyl]amino]-3-(benzothiazol-2-yl)-6-ethyl-4,5,6,7-tetrahydrothieno[2,3-c]pyridine (Compound no. 5);

2-[[4-[(diethylamino)sulfonyl]benzoyl]amino]-3-(benzothiazol-2-yl)-6-ethyl-4,5,6,7-tetrahydrothieno[2,3-c]pyridine (Compound no. 11);

2-[[4-[[ethyl(phenylmethyl)amino]sulfonyl]benzoyl]amino]-6-ethyl-4,5,6,7-tetrahydrothieno[2,3-c]pyridine-3-carboxamide (Compound no. 28);

2-[[4-[(4-methyl-1-piperazinyl)sulfonyl]benzoyl]amino]-6-ethyl-4,5,6,7-tetrahydrothieno[2,3-c]pyridine-3-carboxamide (Compound no. 29).

The present invention also provides compounds and pharmaceutical compositions thereof of formula 2-[[4-[[ethyl(phenylmethyl)amino]sulfonyl]benzoyl]amino]-6-ethyl-4,5,6,7-tetrahydrothieno[2,3-c]pyridine-3-carboxamide (Compound No. 28) and 2-[[4-[(4-methyl-1-piperazinyl)sulfonyl]benzoyl]amino]-6-ethyl-4,5,6,7-tetrahydrothieno[2,3-c]pyridine-3-carboxamide (Compound No. 29), the synthesis of the compounds is described herein below in Examples 1 and 2.

Unless otherwise indicated, all chiral, diastereomeric and racemic forms of the compounds described in the present invention are also included in the present invention; the compounds may also have asymmetric centers. Many geometric isomers of olefins, C- and N-double bonds and the like can also be present in the compounds described herein, and all such stable isomers are contemplated in the present invention. It will be appreciated that compounds of the present invention that contain asymmetrically substituted carbon atoms may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

When a bond to a substituent is shown to cross the bond connecting two atoms in a ring, then such substituent may be bonded to any atom on the ring. When a bond joining a substituent to another group is not specifically shown or the atom in such other group to which the bond joins is not specifically shown, then such substituent may form a bond with any atom on such other group.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted", as used herein, means that any one or more hydrogen on the designated atom is replaced with a selection from the indicated group, provided that the designated atom's normal valency is not exceeded, and that the substitution results in a stable compound.

A "lead compound" is a compound in a selected combinatorial library, for which the assay has revealed significant effect relevant to a desired cell activity to be modulated. In the present case the property is the modulation of at least one biological activity associated with a GAG or GAG-ECAM interactions.

The term "alkyl" refers to a straight or branched chain or cyclic hydrocarbon having 1-12 carbon atoms. In one embodiment, the alkyl has 1-10 carbons. In another embodiment, the alkyl has 1-8 carbons. In another embodiment, the alkyl has 1-6 carbons. In another embodiment, the alkyl has 1-4 carbons. The alkyl may be unsubstituted or substituted by one or more substituents, i.e. substituents that do not interfere with the biological activity of the compounds. Non-limiting examples of suitable substituents include but are not limited to halo, hydroxy, $C_1$-$C_{10}$ alkyl, $C_2$-$C_{10}$ alkenyl, $C_2$-$C_{10}$ alkynyl, $C_1$-$C_{10}$ alkoxy, $C_7$-$C_{12}$ aralkyl, $C_7$-$C_{12}$ alkaryl, $C_1$-$C_{10}$ alkylthio, arylthio, aryloxy, arylamino, $C_3$-$C_{10}$ cycloalkyl, $C_3$-$C_{10}$ cycloalkenyl, di($C_1$-$C_{10}$)-alkylamino, $C_2$-$C_{12}$ alkoxyalkyl, $C_1$-$C_6$ alkylsulfinyl, $C_1$-$C_{10}$ alkylsulfonyl, arylsulfonyl, aryl, hydroxy, hydroxy($C_1$-$C_{10}$) alkyl, aryloxy($C_1$-$C_{10}$)alkyl, $C_1$-$C_{10}$ alkoxycarbonyl, aryloxycarbonyl, aryloyloxy, substituted alkoxy, fluoroalkyl, nitro, cyano, cyano($C_1$-$C_{10}$)alkyl, $C_1$-$C_{10}$ alkanamido, aryloylamido, arylaminosulfonyl, sulfonamido, amidino, amido, alkylamido, dialkylamido, amino, alkylamino, dialkylamino, carbonyl, carbamido, carboxy, heterocyclic radical, nitroalkyl, and —$(CH_2)_m$-Z-($C_1$-$C_{10}$alkyl), where m is 1 to 8 and z is oxygen or sulfur. The term "lower alkyl" refers to straight chain or branched alkyl groups of 1-6 carbon atoms, such as methyl, ethyl, 1-methylethyl, propyl, butyl, isobutyl, sec-butyl, t-butyl, pentyl, isopentyl, hexyl and the like. In one preferred embodiment, the lower alkyl is a methyl group. In another preferred embodiment, the lower alkyl is a methylethyl group.

The term "aryl" refers to an aromatic group having at least one carbocyclic aromatic group, which may be unsubstituted or substituted by one or more inert substituents as defined hereinabove.

The term "heterocyclyl" or "heteroaryl" refers to a ring containing one or more heteroatoms, for example oxygen, nitrogen, sulfur and the like, with or without unsaturation or aromatic character, optionally substituted with one or more inert substituents as defined hereinabove. Non-limiting examples of heterocyclic substituents are imidazole, pyrazole, pyrazine, thiazole, thiazine, oxazole, furan, dihydrofuran, tetrahydrofuran, pyridine, dihydropyridine, tetrahydropyridine, isoxazole and the like. Multiple rings may be fused, as in quinoline or benzofuran, or unfused as in 4-phenylpyridine.

The heterocyclic moiety is a one or two ringed moiety containing one or more heteroatoms, preferably nitrogens, which may be isolated or fused, for example and without being limited to—imidazole, pyrazole, pyrazine, pyridine, dihydropyridine, tetrahydropyridine, isoxazole, quinoline, isoquinoline and the like.

A "haloalkyl" group refers to an alkyl group as defined above, which is substituted by one or more halogen atoms, e.g., by F, Cl, Br or I. A "hydroxyl" group refers to an OH group. An "alkenyl" group refers to a group having at least one carbon-to-carbon double bond. An "arylalkyl" group refers to an alkyl bound to an aryl, wherein alkyl and aryl are as defined above. An example of an arylalkyl group is a benzyl group.

As contemplated herein, the present invention further encompasses analogs, derivatives, isomers, pharmaceutically acceptable salts and hydrates of the compounds defined by the present invention.

The term "isomer" includes, but is not limited to, optical isomers and analogs, structural isomers and analogs, conformational isomers and analogs, and the like. Thus, the present invention encompasses various optical isomers of the compounds of the present invention. It will be appreciated by those skilled in the art that the compounds of the present invention contain at least one chiral center. Accordingly, these compounds exist in, and are isolated in, optically active or racemic forms. Some compounds may also exhibit polymorphism. It is to be understood that the present invention encompasses any racemic, optically active, polymorphic, or stereroisomeric form, or mixtures thereof. In one embodiment, the compounds are the pure (R)-isomers. In another embodiment, the compounds are the pure (S)-isomers. In another embodiment, the compounds are a mixture of the (R) and the (S) isomers. In another embodiment, the compounds are a racemic mixture comprising an equal amount of the (R) and the (S) isomers. It is well known in the art how to prepare optically active forms, for example, by resolution of the racemic form by recrystallization techniques, by synthesis from optically active starting materials, by chiral synthesis, or by chromatographic separation using a chiral stationary phase.

This invention further includes derivatives of the compounds. The term "derivatives" includes, but is not limited to, ether derivatives, acid derivatives, amide derivatives, ester derivatives, and the like. In addition, this invention further includes hydrates of the compounds described herein. The term "hydrate" includes but is not limited to hemihydrate, monohydrate, dihydrate, trihydrate, and the like.

The derivatives of the compounds of the present invention can also be in the form of prodrugs. Prodrugs are considered to be any covalently bonded carriers that release the active parent drug according to Formula I in vivo, when such prodrug is administered to a mammalian subject. Prodrugs of the compounds of Formula I are prepared by modifying functional groups present in the compounds in such a way that the modifications are cleaved, either in routine manipulation or in vivo, to the parent compounds. Prodrugs include compounds of Formula I wherein hydroxyl, amino, sulfhydryl, or carboxyl groups are bonded to any group that, when administered to a mammalian subject, are cleaved to form a free hydroxyl, amino, sulfhydryl, or carboxyl group, respectively. Examples of prodrugs include, but are not limited to, acetate, formate, and benzoate derivatives of alcohol and amine functional groups in the compounds of Formula I, and the like.

According to one embodiment, the compounds of the present invention inhibit the interaction of GAGs with GAG specific ECAMs.

According to another embodiment, the compounds of the present invention inhibit the interactions of HS-GAGs with selectins, specifically L-selectin and P-selectin (see Example 5 and Table 1 herein below).

According to yet another embodiment, the compounds of the present invention bind directly to GAGs, specifically HS-GAG (see Example 6 herein below). The compounds of the invention can thus be employed for treatment or prevention of diseases and disorders mediated by GAGs.

According to yet another embodiment the present invention provides a method for inhibiting cell adhesion and cell migration in vitro comprising the step of exposing the cell to at least one compound according to formula I in an amount sufficient to inhibit GAG to GAG specific ECAM interactions (see Example 7 herein below).

Figure 2:
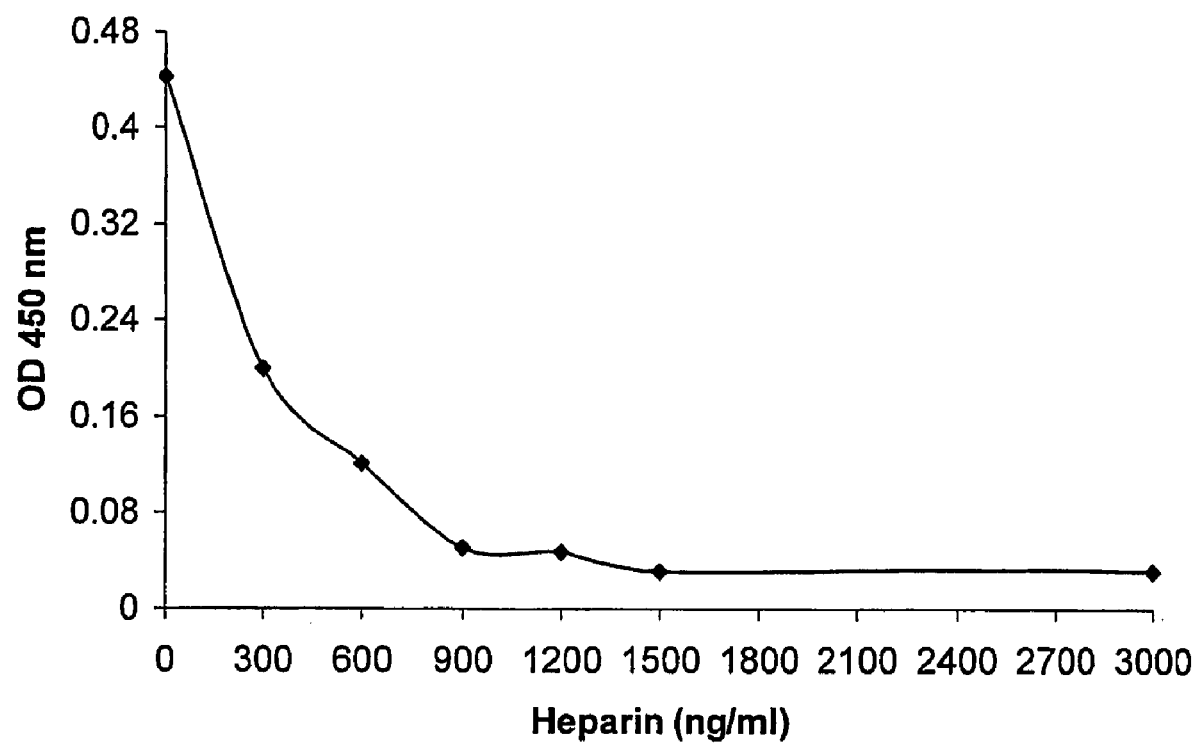
FIG. 2 demonstrates inhibition of L-selectin/IgG binding to immobilized heparin by soluble heparin.
Figure 3:
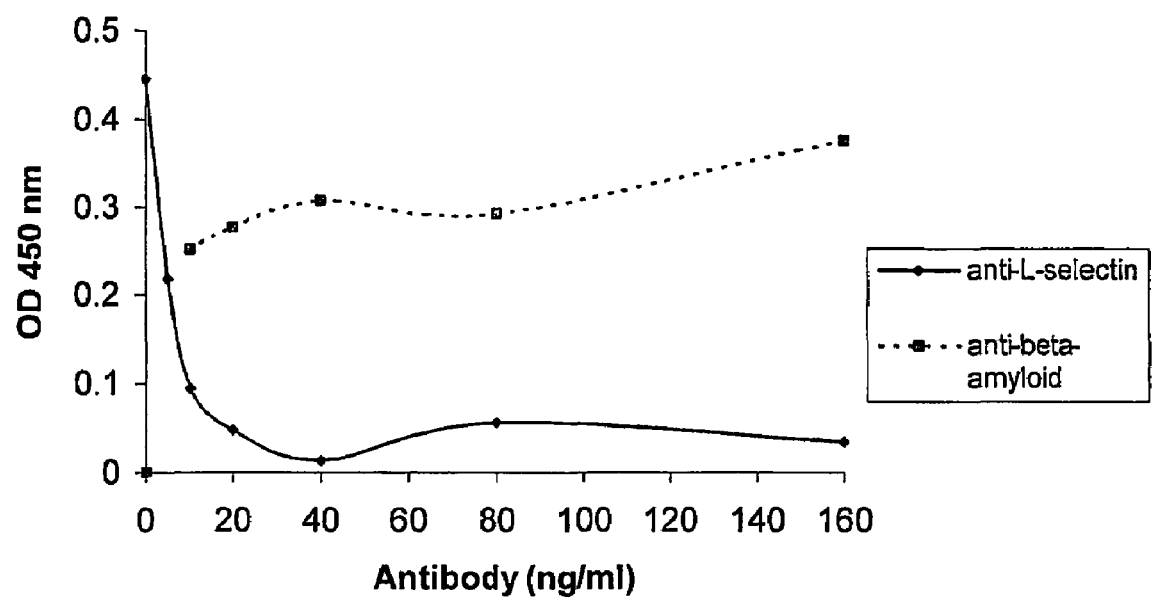
FIG. 3 shows inhibition of L-selectin/IgG binding to immobilized heparin by anti-L-selectin antibody DREGG-55. Anti-beta-amyloid antibodies were used as a control.

The inhibitory effect of the compounds of the present invention can be evaluated by several methods in vitro. One assay for measuring GAG-ECAM binding, exemplified herein below, detects the binding of L selectin/IgG to immobilized heparin. Another assay utilizes immobilized L-selectin, or L-selectin fused to protein domains other than IgG. The amount of bound L-selectin is determined by an ELISA assay using, for example, a monoclonal antibody raised against L-selectin, which is conjugated to horseradish peroxidase. FIG. 1 shows the saturation curve of the L-selectin/IgG binding to heparin. As shown in FIG. 2, soluble heparin inhibited L-selectin/IgG binding to immobilized heparin. A mAb directed against the carbohydrate-binding domain of L-selectin (Dregg-55) inhibited L-selectin/IgG binding to heparin (FIG. 3), while a non-specific antibody such as anti-beta amyloid did not inhibit the binding, thus providing a further confirmation of the specificity of binding. The Dregg-55 antibody was also shown to inhibit L-selectin-dependent adhesion in vitro, neutrophil accumulation in vitro and inflammation in vivo (Co M. S. et al, Immunotechnology 493: 253-266, 1999). Thus, the experiment with Dregg-55 antibody shows that the assay according to the present invention is useful for discovery of compounds inhibiting cell interaction and infiltration and having therapeutic potential.

The biological activity of the compounds according to formula I of the present invention may be assayed in a variety of systems. For example, a compound can be immobilized on a solid surface and adhesion of cells expressing HS-GAGs can be measured. The test compounds can also be tested for the ability to competitively inhibit binding between HS-GAGs and other proteins binding to HS-GAGs such as other cell adhesion molecules, cytokines, or viral proteins. Many assay formats employ radioactive or non-radioactive labeled assay components. The labeling systems can be in a variety of forms. The label may be coupled directly or indirectly to the desired component of the assay according to methods well known in the art.

Figure 4:
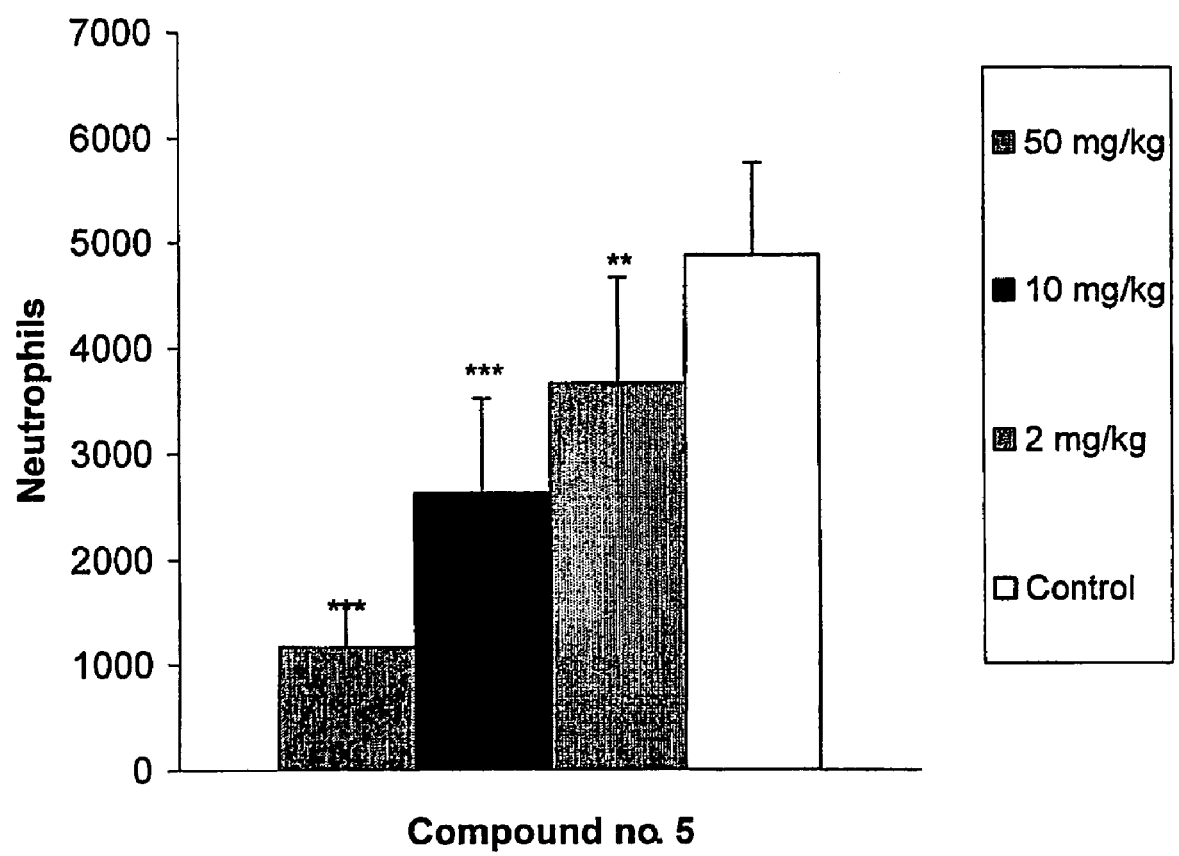
FIG. 4 shows dose-dependent inhibition of Compound no. 5 of neutrophil infiltration in mouse peritonitis.

According to a further embodiment the compounds of the present invention inhibit leukocyte and neutrophil infiltration in vivo (see Example 8 and FIG. 4 herein below).

The ability of compounds of the present invention to reduce leukocyte migration to sites of acute inflammation was evaluated in BALB/c mice using a thioglycolate-induced model of peritonitis. In this animal model, interactions of L- and P-selectin with HS-GAGs have been implicated in neutrophil infiltration (Nelson, R. M., 82:3253-3258, 1993; Xie, X. et al., J. Biol. Chem., 275:34818-34825, 2000).

Compounds according to formula I of the present invention were shown to efficiently inhibit leukocyte and neutrophil migration into the peritoneal cavity. The compounds were also shown to reduce lymphocyte migration, evaluated in mice using a model of Delayed Type Hypersensitivity (see Example 10 and FIG. 6 herein below; for the method see Lange-Asschenfeldt B. et al., Blood, 99:538-545, 2002).

Compounds of the present invention having the desired biological activity may be modified as necessary to provide desired properties such as improved pharmacological properties.

For diagnostic purposes, a wide variety of labels may be linked to the compounds, which may provide, directly or indirectly, a detectable signal. Thus, the compounds of the present invention may be modified in a variety of ways for a variety of end purposes while still retaining biological activity. In addition, various reactive sites may be introduced at the terminus for linking to particles, solid substrates, macromolecules, or the like.

Labeled compounds can be used in a variety of in vivo or in vitro applications. A wide variety of labels may be employed, such as radionuclides (e.g., gamma-emitting radioisotopes such as technetium-99 or indium-111), fluorescent agents (e.g., fluorescein), enzymes, enzyme substrates, enzyme cofactors, enzyme inhibitors, chemiluminescent compounds, bioluminescent compounds, and the like. Those of ordinary skill in the art will know of other suitable labels for binding to the compounds, or will be able to ascertain such using routine experimentation. The binding of these labels is achieved using standard techniques common to those of ordinary skill in the art.

For in vivo diagnostic imaging to identify, for example, sites of inflammation, radioisotopes are typically used in accordance with well-known techniques.

The invention includes pharmaceutically acceptable salts of the compounds of the present invention. Pharmaceutically acceptable salts can be prepared by treatment with inorganic bases, for example, sodium hydroxide or inorganic/organic acids such as hydrochloric acid, citric acids and the like.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It is to be understood that, as used herein, references to the compounds according to formula I of the present invention are meant to also include the pharmaceutically acceptable salts thereof.

Pharmaceutical Formulations

The pharmaceutical compositions of the present invention can be formulated for administration by a variety of routes including oral, rectal, transdermal, subcutaneous, intravenous, intramuscular, and intranasal. Such compositions are prepared in a manner well known in the pharmaceutical art and comprise as an active ingredient at least one compound according to formula I and derivatives thereof as described herein above, further comprising an excipient or a carrier. During the preparation of the pharmaceutical compositions according to the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active ingredient to provide the appropriate particle size prior to combining with the other ingredients. If the active compound is substantially insoluble, it ordinarily is milled to a particle size of less than 200 mesh. If the active ingredient is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methylcellulose. The formulations can additionally include lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.1 to about 500 mg. The term "unit dosage forms" refers to physically discrete units suitable as unitary dosages for human subjects and other mammals, each unit containing a predetermined quantity of the active compound calculated to produce the desired therapeutic effect, in association with a suitable pharmaceutical excipient.

The active ingredient is effective over a wide dosage range and is generally administered in a therapeutically effective amount. It will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permit the inner component to pass intact into the duodenum or to be delayed in release. A variety of materials can be used for such enteric layers or coatings; such materials include a number of polymeric acids and mixtures of polymeric acids with materials such as shellac, cetyl alcohol, and cellulose acetate.

The liquid forms in which the compositions of the present invention may be incorporated, for administration orally or by injection, include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insulation include solutions and suspensions in pharmaceutically acceptable aqueous or organic solvents, or mixtures thereof, and powders. The liquid or solid compositions may contain suitable pharmaceutically acceptable excipients as described above. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices that deliver the formulation in an appropriate manner.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252 incorporated herein by reference as if fully set forth. Such patches may be constructed for continuous, pulsatile, or on demand delivery of pharmaceutical agents.

Direct or indirect placement techniques may be used when it is desirable or necessary to introduce the pharmaceutical composition to the brain. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 incorporated herein by reference as if fully set forth. Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions, which can transiently open the blood-brain barrier.

Therapeutic Use

The present invention provides small organic compounds that inhibit cell-matrix and cell-cell interaction, thus inhibiting a cascade of events that lead to the development of certain diseases and disorders.

According to some aspects, the present invention provides a method for the treatment or prevention of diseases and disorders related to cell adhesion and cell migration mediated by GAG-ECAM interactions, comprising the step of administering to a subject in need thereof a therapeutically effective amount of a pharmaceutical composition comprising a compound having the general formula I:

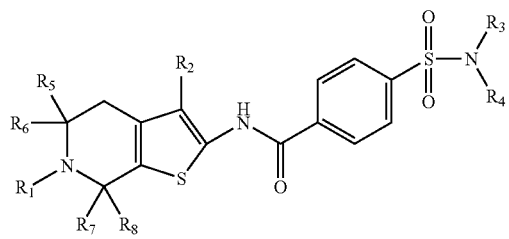

wherein:

$R_1$ is selected from the group consisting of H; straight or branched alkyl of 1-6 carbon atoms; arylalkyl; substituted arylalkyl; cycloalkyl, optionally substituted with alkyl groups; alkanoyl; arylcarbonyl optionally substituted at the aryl group; cycloalkylcarbonyl; alkoxycarbonyl;

$R_2$ is selected from the group consisting of carboxy; cyano; aminocarbonyl; alkylaminocarbonyl; arylaminocarbonyl optionally substituted at the aryl group; dialkylaminocarbonyl wherein each alkyl is straight or branched chain $C_1$-$C_6$ alkyl or both alkyl groups together may form a 3-7 membered saturated, unsaturated or aromatic monocyclic or bicyclic nitrogen containing heterocyclyl, optionally containing one or two additional heteroatoms; alkoxycarbonyl; alkanoyl; cycloalkylcarbonyl; arylcarbonyl optionally substituted on the aryl group, benzothiazol-2-yl;

$R_3$ and $R_4$ are selected from the group consisting of $C_1$-$C_6$ alkyl, optionally substituted by hydroxy, alkoxy, amino or alkylamino, $C_2$-$C_4$ monounsaturated alkenyl, cycloalkyl, aryl, arylmethyl, or $R_3$ and $R_4$ together may form an optionally substituted 5-7 membered saturated, unsaturated or aromatic monocyclic or bicyclic nitrogen containing heterocyclyl, optionally containing one or two additional heteroatoms;

$R_5$, $R_6$, $R_7$ and $R_8$ are selected from the group consisting of H or $C_1$-$C_6$ alkyl, with the proviso that when $R_5$, $R_6$, $R_7$ and $R_8$ are $C_1$-$C_6$ alkyl, $R_1$ is hydrogen;

and pharmaceutically acceptable salts thereof; further comprising a pharmaceutically acceptable diluent or carrier.

The preferred pharmaceutical compositions for the treatment and prevention of diseases and disorders related to cell adhesion and cell migration mediated by GAG-ECAM interactions are listed herein above.

According to one embodiment, the pharmaceutical compositions according to the present invention are used for the treatment of diseases or disorders related to GAG-ECAM interactions wherein the GAGs are selected from the group consisting of heparan sulfate (HS-GAG), heparin, chondroitin sulfate, dermatan sulfate, keratan sulfate, and derivatives and fragments thereof.

According to one currently preferred embodiment, the pharmaceutical compositions according to the present invention are used for the treatment of diseases or disorders related to GAG-ECAM interactions wherein the GAG is HS-GAG.

According to yet another embodiment, the pharmaceutical compositions according to the present invention are used for the treatment of diseases or disorders related to GAG-ECAM interactions wherein the GAG specific ECAMs are selected from the group consisting of selectins, integrins, fibronectin, and cytokines.

According to one currently preferred embodiment, the pharmaceutical compositions according to the present invention are used for the treatment of diseases or disorders related to GAG-ECAM interactions wherein the GAG specific ECAMs are selected from the group consisting of L-selectin and P-selectin.

Anti cell adhesion and anti-cell migration therapy has proven to be highly effective in the treatment of number of diseases and disorders including inflammatory processes, autoimmune processes, cancer and tumor metastasis, and platelet-mediated pathologies.

A number of inflammatory disorders associated with L- and P-selectin or involve selectin-mediated leukocyte flow along the blood stream may be treated with the pharmaceutical compositions of the invention. Treatable disorders include, but are not limited to, organ or tissue transplantation rejection (e.g., allograft rejection or autologous bone marrow transplantation), atherosclerosis, retinitis, cancer metastases, rheumatoid arthritis, acute leukocyte-mediated lung injury (e.g., adult respiratory distress syndrome), asthma, allergic rhinitis, allergic conjunctivitis, inflammatory lung diseases, restenosis, nephritis, acute and chronic inflammation, atopic dermatitis, psoriasis, contact dermal hypersensitivity, myocardial ischemia, and inflammatory bowel disease. In preferred embodiments the pharmaceutical compositions are used to treat inflammatory disorders associated with neutrophil infiltration, such as ischemia-reperfusion injury, acute pancreatitis, septic shock, uveitis, rheumatoid arthritis, and inflammatory bowel disease.

Reperfusion injury is a major problem in clinical cardiology. Therapeutic agents that reduce leukocyte adherence in ischemic myocardium can significantly enhance the therapeutic efficacy of thrombolytic agents. Thrombolytic therapy with agents such as tissue plasminogen activator or streptokinase can relieve coronary artery obstruction in many patients with severe myocardial ischemia prior to irreversible myocardial cell death. However, many such patients still suffer myocardial necrosis despite restoration of blood flow. This "reperfusion injury" is known to be associated with adherence of leukocytes to vascular endothelium in the ischemic zone, presumably in part because of activation of platelets and endothelium by thrombin and cytokines that makes them adhesive for leukocytes (Romson et al., Circulation 67:1016-1023, 1983). These adherent leukocytes can migrate through the endothelium and ischemic myocardium just as it is being rescued by restoration of blood flow.

Inflammatory bowel disease is a collective term for two similar diseases referred to as Crohn's disease and ulcerative colitis. Crohn's disease is an idiopathic, chronic ulceroconstrictive inflammatory disease characterized by sharply delimited and typically transmural involvement of all layers of the bowel wall by a granulomatous inflammatory reaction. Any segment of the gastrointestinal tract, from the mouth to the anus, may be involved, although the disease most commonly affects the terminal ileum and/or colon. Ulcerative colitis is an inflammatory response limited largely to the colonic mucosa and submucosa. Lymphocytes and macrophages are numerous in lesions of inflammatory bowel disease and may contribute to inflammatory injury.

Figure 9:
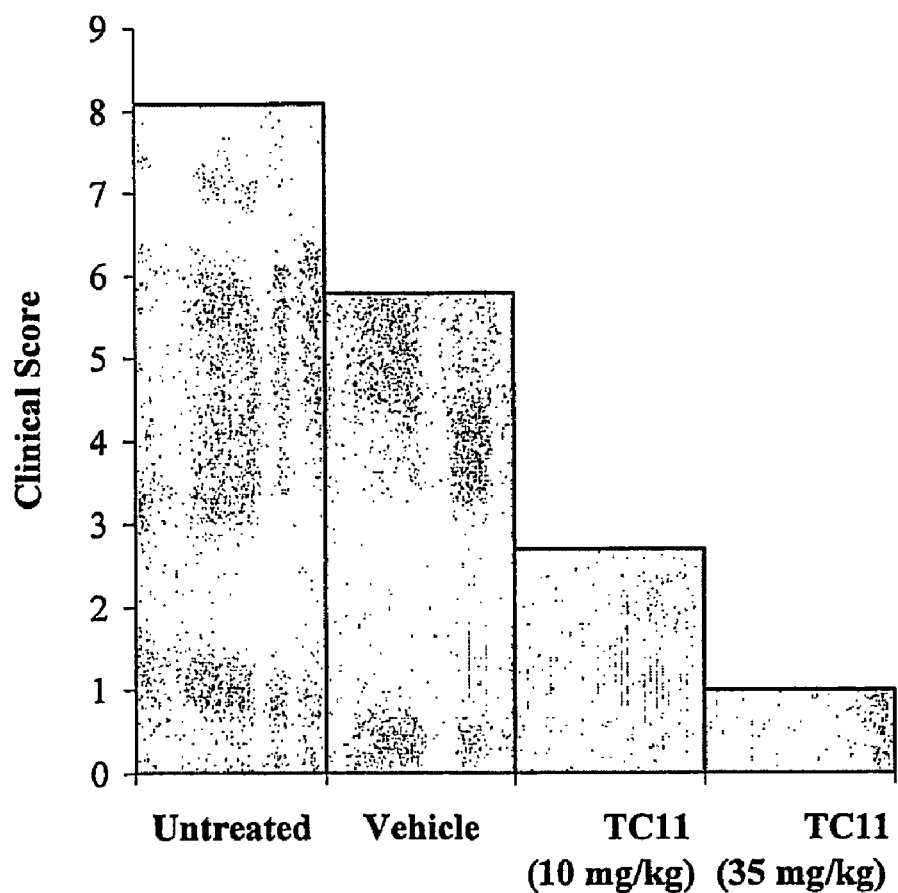
FIG. 9 demonstrates the therapeutic effect of test Compound no. 11 (TC11) administered intra-peritoneally in a mouse model of Inflammatory Bowel Disease (IBD).
Figure 10:
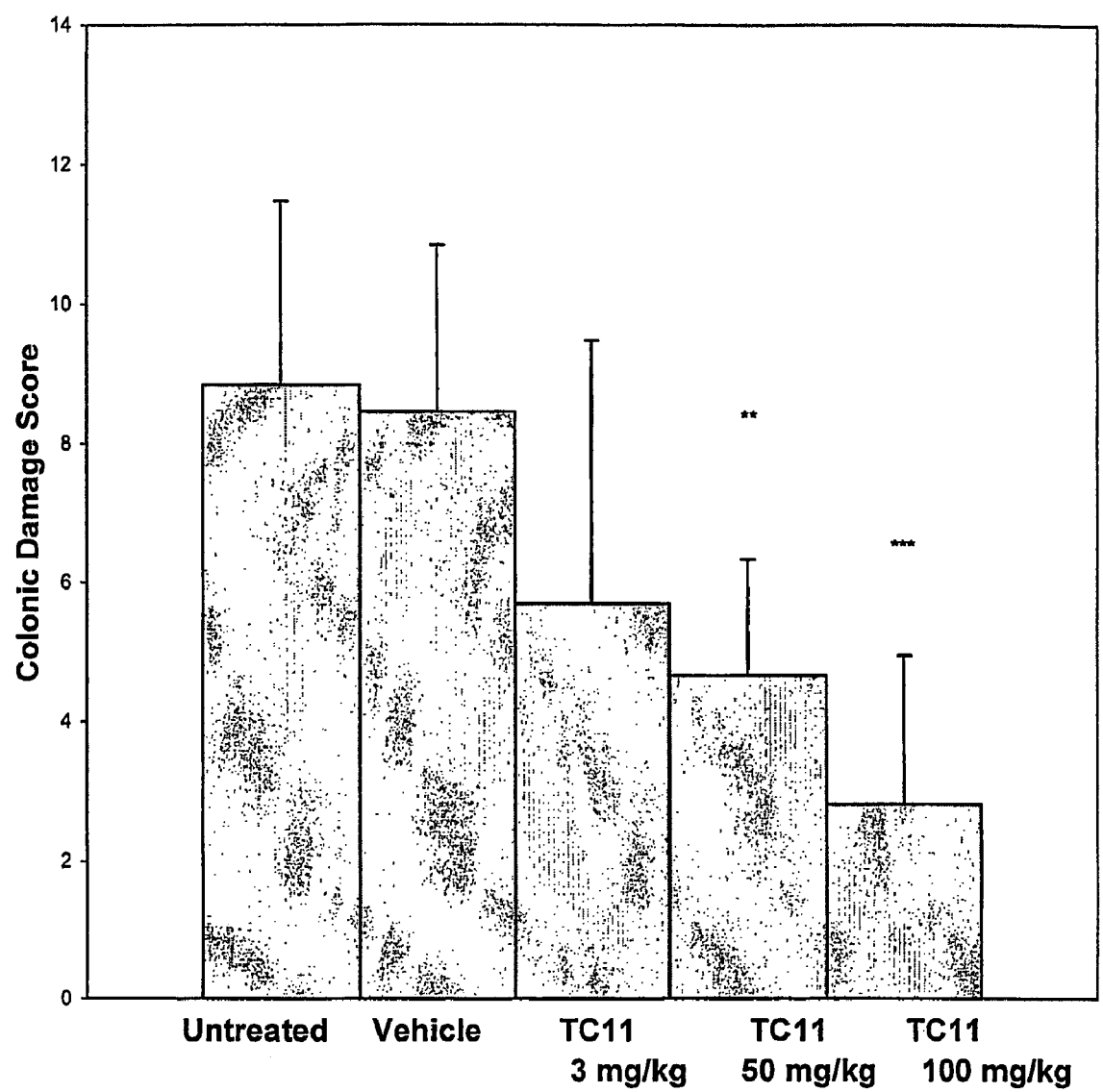
FIG. 10 demonstrates the therapeutic effect of test Compound no. 11 (TC11) administered orally in a mouse model of Inflammatory Bowel Disease (IBD)

According to yet another embodiment, the invention provides a method for the prevention or treatment of inflammatory bowel disease comprising the step of administering to a subject in need thereof a therapeutically effective amount of a pharmaceutical composition comprising as an active ingredient a thieno[2,3-c]pyridine compound of the formula 2-[[4-[(diethylamino)sulfonyl]benzoyl]amino]-3-(benzothiazol-2-yl)-6-ethyl-4,5,6,7-tetrahydrothieno[2,3-c] pyridine (Compound no. 11) and a pharmaceutically acceptable salt; further comprising a pharmaceutically acceptable carrier. As described in Example 8 herein below, Compound no. 5 and Compound no. 11 inhibited leukocyte and neutrophil infiltration into mouse peritoneum. Leukocyte and neutrophil infiltration is considered a hallmark of inflammatory bowel disease. In addition, Example 11 herein below demonstrated that Compound no. 11 significantly inhibited colonic damage in a mouse model of inflammatory bowel disease. As shown in FIGS. 9 and 10, the therapeutic effect of Compound no. 11 was dose-dependent and statistically significant both after intra-peritoneal as well as oral administration.

Asthma is a disease characterized by increased responsiveness of the tracheobronchial tree to various stimuli potentiating paroxysmal constriction of the bronchial airways. The stimuli cause release of various mediators of inflammation that recruit basophils, eosinophils and neutrophils, which cause inflammatory injury.

Rheumatoid arthritis is a chronic, relapsing inflammatory disease that primarily causes impairment and destruction of joints. Rheumatoid arthritis usually first affects the small joints of the hands and feet but then may involve the wrists, elbows, ankles and knees. The arthritis results from interaction of synovial cells with leukocytes that infiltrate from the circulation into the synovial lining of the joints.

Atherosclerosis is a disease of arteries. The basic lesion, the atheroma, consists of a raised focal plaque within the intima, having a core of lipid and a covering fibrous cap. Atheromas compromise arterial blood flow and weaken affected arteries. Myocardial and cerebral infarcts are a major consequence of this disease. Macrophages and leukocytes are recruited to atheromas and contribute to inflammatory injury.

The pharmaceutical compositions of the present invention can be further used in the treatment of organ or graft rejection. Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immnunotolerance in the recipient to the transplanted allograft or organ. When allogeneic cells or organs are transplanted into a host, the host immune system is likely to mount an immune response to foreign antigens in the transplant (host-versus-graft disease) leading to destruction of the transplanted tissue. $CD8^+$ cells, CD4 cells and monocytes are all involved in the rejection of transplant tissues. Compounds of this invention, which inhibit selectins are useful, inter alia, to block alloantigen-induced immune responses thereby preventing such cells from participating in the destruction of the transplanted tissue or organ (see, e.g., Georczynski et al., Immunology 87:573-580, 1996).

A related use of the pharmaceutical compositions according to the present invention is in modulating the immune response involved in "graft versus host" disease (GVHD). GVHD is a potentially fatal disease that occurs when immunologically competent cells are transferred to an allogeneic recipient. In this situation, the donor's immunocompetent cells may attack tissues in the recipient. Tissues of the skin, gut epithelia and liver are frequent targets and may be destroyed during the course of GVHD. The disease presents an especially severe problem when immune tissue is being transplanted, such as in bone marrow transplantation; but less severe GVHD has also been reported in other cases as well, including heart and liver transplants. The compounds of the present invention that modulate donor cell homing pattern mediated by L-selectin are useful for treatment of GVHD (Li, B., Eur J Immunol 31:617-24, 2001).

Further use of the pharmaceutical compositions according to the present invention is for the treatment of cancer and metastasis. As described in Example 13 herein below, Compound no. 1 inhibited the growth of several tumor cell lines. For certain cancers to spread throughout a patient's body, a process of cell-cell adhesion, or metastasis, must take place. Specifically, cancer cells must migrate from their site of origin and gain access to a blood vessel to facilitate colonization at distant sites. A critical aspect of this process is adhesion of cancer cells (to platelets and to endothelial cells that line the blood vessel wall) a step prior to migrating into surrounding tissue. This process can be interrupted by the administration of compounds of the invention, which generally aid in blocking cell-cell adhesion. In particular, P-selectin mediated processes have been implicated in metastasis (Varki, A. and Varki, N. M., Braz J Med Biol Res. 34:711-7, 2001)

Also embodied is the use of the pharmaceutical compositions according to the present invention in the treatment of leukemia, such as Acute Myeloid Leukemia, which involves extravasation of leukemic cells and tumor formation. As described in Example 14, Compound no. 1 inhibited leukemia cell growth. Also embodied in the present invention are methods useful for the treatment (including prevention) of angiogenic disorders. The term "angiogenic disorders" as used herein includes conditions involving abnormal neovascularization, such as tumor metastasis and ocular neovascularization, including, for example, diabetic retinopathy, and neovascular glaucoma.

A further use of the pharmaceutical compositions according to the present invention is in treating multiple sclerosis. Multiple sclerosis is a progressive neurological autoimmune disease that is thought to be the result of a specific autoimmune reaction in which certain leukocytes initiate the destruction of myelin, the insulating sheath covering nerve fibers. Murine monoclonal antibodies directed against L-selectin have been shown to suppress experimental autoimmune encephalomyelitis (EAE), an animal model of multiple sclerosis (Archelos, J. J., J. Neurol. Sci., 159:127-34, 1998).

Figure 11:
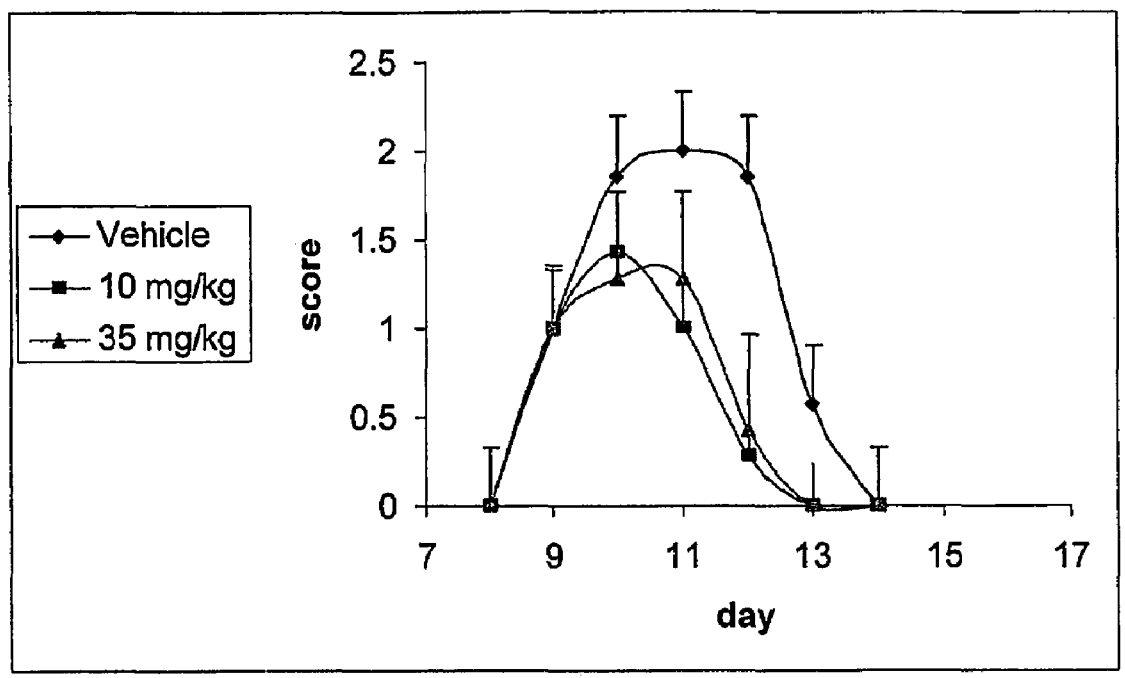
FIG. 11 demonstrates the therapeutic effect of test Compound no. 11 in a rat model of Multiple Sclerosis (Experimental Autoimmune Encephalomyelitis).

The present invention also provides a method for the prevention or treatment of multiple sclerosis comprising the step of administering to a subject in need thereof a therapeutically effective amount of a pharmaceutical composition comprising as an active ingredient the thieno[2,3-c]pyridine compound 2-[[4-[(diethylamino)sulfonyl]benzoyl]amino]-3-(benzothiazol-2-yl)-6-ethyl-4,5,6,7-tetrahydrothieno[2,3-c]pyridine (Compound no. 11) and a pharmaceutically acceptable carrier. As shown in FIG. 11, Compound no. 11 inhibited symptoms of EAE at two concentrations tested.

It has also been found that compounds according to formula I of the present invention directly bind to HS-GAGs and may therefore be useful for treatment of disease conditions mediated by HS-GAGs. HS-GAG mediated conditions include those mediated by cell-cell, cell-virus, cell-matrix and cell-protein interactions. Examples of HS-GAG mediated conditions include virus attachment to cell, cell adhesion, platelet aggregation, lymphocyte adhesion and migration, and amyloid fibril formation.

According to another embodiment, the pharmaceutical compositions according to the present invention are therefore also useful for treatment (or prevention) of viral disorders such as hepatitis C and B, cytomegalovirus infection, respiratory syncytial virus infection, and AIDS.

According to yet another embodiment, the pharmaceutical compositions of the present invention are useful for the treatment or prevention of atherosclerosis, amyloid disorders including Alzheimer's disease and type II diabetes (Non-insulin Dependent Diabetes Mellitus), inflammatory and immune disorders, cancer, bone degradation, osteoporosis, osteoarthritis, tumor metastasis, and kidney disease including glomerulonephritis.

According to yet another embodiment, the pharmaceutical compositions of the present invention are used for the treatment or prevention of coagulation disorders. The compounds of the present invention may be useful for counteracting the actions of heparin and other anticoagulant glycosaminoglycans on thrombin and Factor Xa activity, and nay affect other coagulation proteins as well. Heparin is used routinely for anticoagulation. The interactions of exogenously administered heparin with the proteins of the coagulation and fibrinolytic pathways have been summarized in detail (see for example Van Kuppevelt, T. H., et al., J Biol Chem, 273: 12960-12966, 1998). It is often necessary to reverse the effects of heparin when anticoagulation has reached a stage at which hemorrhage becomes a threat, notably after the routine use of heparin for anticoagulation during cardiopulmonary bypass, and in patients who develop an endogenous heparin-like coagulation inhibitor. Currently, the only FDA-approved heparin antidote available is Protamine. Protamine is a mixture of basic proteins from fish sperm nuclei that contains a high concentration of the amino acid arginine. When injected into a person who has been treated with heparin, Protamine complexes rapidly to the heparin, thereby neutralizing its activity. Although Protamine is effective in humans against unfractionated heparin, it is not effective against low molecular weight heparins or against the non-heparin glycosaminoglycan anti-coagulant Orgaran®, i.e., a mixture of chondroitin sulfate/heparan sulfate/dermatan sulfate. Protamine also has numerous side effects including pulmonary hypotension that are difficult to control and provide significant health risks to the patient. Also, since Protamine is obtained from a natural source, it is a poorly-defined and potentially variable product, dosage determination can be problematic. Well-defined heparin- or other GAG-binding compounds could be of considerable utility for reversing overdose of these specific anticoagulant preparations. Carson and co-workers (Munro, M. S., et al., Trans Am Soc Artif Intern Organs, 27: 499-503,1983) have identified a heparin-binding peptide from an epithelial/endothelial cell surface protein that has some ability to neutralize heparin effects on thrombin generation, but optimal effects were found only at high peptide concentrations and low heparin and low thrombin concentrations. The small organic compounds of the invention would be substantially preferable over these peptides as they are more stable and cost effective. The compounds of the invention can thus be useful in neutralization of unfractionated heparin, low molecular weight heparin, or Orgaran.

Multiple interactions between the proteins of the coagulation and fibrinolysis pathways and endothelial cell surface PGs are normally balanced on the surface of the endothelial cells in order to create a non-thrombotic state. Heparin-binding compounds of the invention could behave similarly to platelet factor 4 (PF4) in that they could bind to heparin, reduce the anticoagulant activity, which occurs on the surface of endothelial cells, and thereby enable a clot to form.

Additional possible use for the compounds of the present invention is to block the uptake and clearance of heparin by blocking heparin receptors in tissues without binding to circulating heparin, and thus to prolong the half-life of heparin in the circulation. Use of the compounds of the invention would reduce the frequency of administration of heparin, as well as the amount needed. This could be especially useful for home-based therapy with low molecular weight heparin, which is administered by subcutaneous injection and is becoming the standard post-hospitalization anticoagulation treatment.

It is to be understood that while the compounds according to formula I of the present invention were selected for their capacity to inhibit binding of certain selectins to HS-GAGs, and that this property contributes to their medical activity, it cannot, however, be excluded that the compounds are also exerting their favorable medical effects, either in parallel or in tandem, through additional mechanisms of action. Thus, the skilled practitioner of this art will appreciate that one aspect of the present invention is the description of novel pharmaceutical compositions, and that Applicants intend not to be bound by a particular mechanism of action that may account for their prophylactic or therapeutic effects.

The principles of the invention, providing novel compounds capable of inhibiting GAGs-ECAMs interactions, their pharmaceutical compositions and use thereof according to the present invention, may be better understood with reference to the following non-limiting examples.

EXAMPLES

Example 1

General Synthesis of Compounds of Formula I

Compounds of Formula I are synthesized according to scheme of the reaction described by Noravyan et al. (A. S. Noravyan et al., Khim.-Farm. Zh., 14, 37-40, 1980). A compound according to formula A herein below ($R_1$ and $R_2$ are defined as in formula I) is reacted with an acid chloride of the compound according to formula B herein below (where $R_3$ and $R_4$ are defined as in formula I) in dry benzene under reflux, in the presence of triethylamine. The precipitated crystals of triethylamine hydrochloride are filtered off and the filtrate is evaporated under slight vacuum. Work up of the residue affords the target compounds of formula I in 60-80% yield.

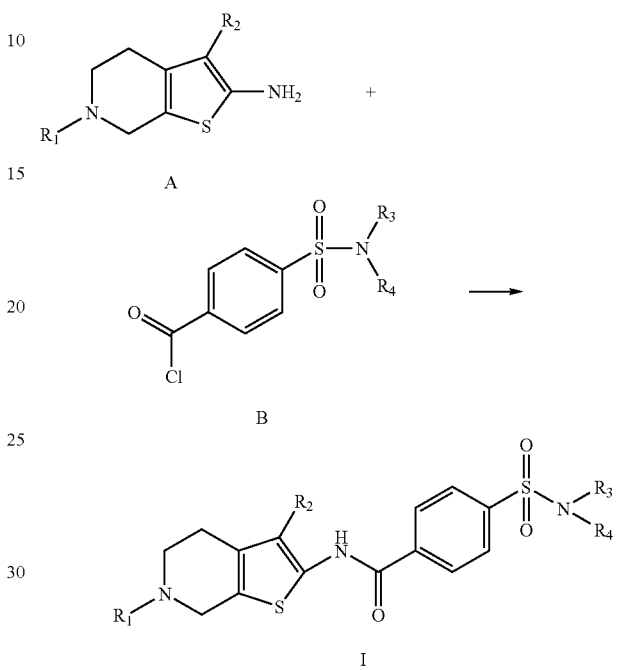

Example 2

Synthesis of Compound No. 29

The synthesis of the following compound:
2-[[4-[(4-methyl-1-piperazinyl)sulfonyl]benzoyl]amino]-6-ethyl-4,5,6,7-tetrahydrothieno[2,3-c]pyridine-3-carboxamide (Compound no. 29) was performed as follows:

To a solution of 2.25 g (10 mmol) 2-amino-6-ethyl-4,5,6,7-tetrahydrothieno[2,3-c]pyridine-3-carboxamide in dry toluene 2.0 g (20 mmol) triethylamine and 3.6 g (12 mmol) p-[(4-methyl-1-piperazinyl)sulfonyl]benzoyl chloride in 30 ml of dry toluene were added. The reaction mixture was refluxed for 3 h and cooled. The precipitated crystals of triethylamine hydrochlorid were filtered off. The filtrate was evaporated in vacuum and the residue crystallized on addition of ethyl acetate. The yellow crystals were washed with ethyl acetate and dried. The target compound was obtained in 72% yield, melting point 232° C.

$^1$H NMR (DMSO-$d_6$) δ (ppm): 7.80-8.12 (4H,m, benzene), 3.8 (2H, m, $CH_2$), 2.82 (8H, t, $CH_2$-piperazine), 2.28-2.41 (6H, m, $3CH_2$), 1.14 (3H, t, $CH_3$), 0.90 (3H, t, $NCH_3$).

Example 3

Synthesis of Compound No. 28

The synthesis of the following compound:
2-[[4-[[ethyl(phenylmethyl)amino]sulfonyl]benzoyl]amino]-6-ethyl-4,5,6,7-tetrahydrothieno[2,3-c]pyridine-3-carboxamide (Compound no. 28) was performed as follows:

To a solution of 2.25 g (10 mmol) 2-amino-6-ethyl-4,5,6,7-tetrahydrothieno[2,3-c]pyridine-3-carboxamide in dry toluene 2.0 g (20 mmol) triethylamine and 4.0 g (12 mmol) p-[[ethyl(phenylmethyl)amino]sulfonyl]benzoyl chloride in 30 ml of dry toluene were added. The reaction mixture was refluxed for 3 h and cooled. The precipitated triethylamine hydrochloride was filtered off. The filtrate was evaporated in vacuum and the residue crystallized on addition of ethyl acetate. The yellow crystals were washed with ethyl acetate and dried. The target compound was obtained in 65% yield, melting point 246° C.

$^1$H NMR (DMSO-d$_6$) δ (ppm): 8.03-8.10 (4H, m, benzene), 7.28-7.33 (5H, m, benzene), 4.36 (2H, s, NCH$_2$Ph), 3.58 (2H, m, CH$_2$), 3.18 (2H, m, CH$_2$), 2.50-2.90 (6H, m, CH$_2$), 1.34 (3H, t, CH$_3$), 0.88 (3H, t, CH$_3$).

Example 4

Pharmaceutical Compositions

The pharmaceutical compositions of the present invention are illustrated by the following formulation examples:

Formulation Example 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
|---|---|
| Active Ingredient | 5.0 |
| Lactose | 95.0 |

The active ingredient is mixed with the lactose and the mixture is added to a dry powder inhaling-appliance.

Formulation Example 4

Tablets, each containing 30 mg of active ingredient, are prepared as follows:

| Ingredient | Quantity (mg/tablet) |
|---|---|
| Active Ingredient | 30.0 |
| Starch | 45.0 |
| Microcrystalline cellulose | 35.0 |
| Polyvinylpyrrolidone (as 10% solution in water) | 4.0 |
| Sodium carboxymethyl starch | 4.50 |
| Magnesium stearate | 0.5 |
| Talc | 1.0 |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of the active ingredient are made as follows:

| Ingredient | Quantity (mg/capsule) |
|---|---|
| Active Ingredient | 40.0 |
| Starch | 109.0 |
| Magnesium stearate | 1.0 |

The active ingredient, starch, and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Quantity (mg) |
|---|---|
| Active Ingredient | 25.0 |
| Saturated fatty acid glycerides | 2000.0 |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of an active ingredient per 5.0 ml dose are made as follows:

| Ingredient | Quantity (mg) |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. mg |
| Purified water | to 5.0 ml |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

Capsules, each containing 15 mg of an active ingredient, are made as follows:

| Ingredient | Quantity (mg/capsule) |
| --- | --- |
| Active Ingredient | 15.0 |
| Starch | 407.0 |
| Magnesium stearate | 3.0 |

The active ingredient, cellulose, starch, and magnesium stearate are blended, passed through a No. 20 mesh U.S. sieve, and filled into hard gelatin capsules in 425 mg quantities.

Formulation Example 9

An intravenous formulation may be prepared as follows:

| Ingredient | Quantity |
| --- | --- |
| Active Ingredient | 250.0 mg |
| Isotonic saline | 1000 ml |

A topical formulation may be prepared as follows:

| Ingredient | Quantity |
| --- | --- |
| Active Ingredient | 1-10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solidified.

Example 5

In vitro Assay for Determining Inhibition of L-selectin (P-Selectin) Binding to HS-GAGs by Inhibitor Compounds According to Formula I An in vitro assay was used to assess the ability of test compounds according to formula I to inhibit the interactions of L-selectin with HS-GAGs. The assay was suitable for determining the concentration required for 50% inhibition (IC-50) for each specific compound. In the assay, the GAG used was heparin. Thus, porcine intestinal mucosa heparin conjugated to Bovine Serum Albumin (Heparin-BSA; Sigma Cat. No. H0403) at 5 mg/ml in Phosphate Buffered Saline (PBS; pH 6.5) was added to a 96 well polystyrene ELISA plate (NUNC Cat. No. 442404; 0.1 ml per well) and incubated Over Night (ON) at 4° C. Following the incubation, the plate was washed thoroughly, by immersion, with de-ionized water and PBS (pH 6.5). The ELISA plate was then blocked with BSA (ICN Cat. No.160069, 3%, 200 µl per well) for 1 hour at Room Temperature (RT). Following blocking, the plate was washed with de-ionized water, and then with PBS (pH 6.5) containing Tween 20 (Sigma Cat. No. P-1379, 0.05%). Compounds were synthesized or purchased from ChemDiv Labs (San Diego, Calif.), dissolved in DMSO, diluted in PBS and added to the wells at various concentrations in the range of 0.01 to 300 µM. Recombinant Human L-Selectin/IgG (Research and Development Systems Cat. No.728-LS) dissolved in PBS supplemented with BSA (0.1%) and calcium chloride (1 mM) was added to the ELISA plate (100 µl per well) and incubated for 60 minutes at RT with shaking. Following incubation, the plate was washed with de-ionized water and three times with PBS (pH 6.5) containing Tween 20. Anti-Human IgG Peroxidase Conjugate (1:5000; Sigma Product No. A8667) diluted in PBS supplemented with BSA (0.1%) and calcium chloride (1 mM) was added to the ELISA plate (100 µl per well) and incubated for 30 minutes at RT with shaking. The plate was then washed with de-ionized water and three times with PBS (pH 6.5) containing Tween 20. The peroxidase substrate cromogen, TMB (Dako Cat. No. S1599) was added (100 µl per well) to the ELISA plate and incubated at room temperature. After 15 minutes ELISA Stop Solution (hydrochloric acid 1N, sulfuric acid 3N) was added (200 µl per well) to stop the peroxidase catalyzed colorimetric reaction. The Optical Density (OD) of the samples was measured at 450 nm using an ELISA plate reader (Dynatech MR5000). Data were analyzed with Graphpad Prism software and IC-50 values were established. The P-selectin assay was carried out in a similar fashion, except that Recombinant Human P-Selectin/IgG (Research and Development Systems Cat.No.137-PS) was used.

It was established that compounds of Formula I had inhibitory activity in the above assays. Examples of inhibitor Compounds are given in Table 1.

TABLE 1
Inhibition of L-Selectin Binding to Heparin by Selected Compounds
| Compound No. | Structure | % Inhibition at 50 μM | IC-50 [μM] |
|---|---|---|---|
| 1 | 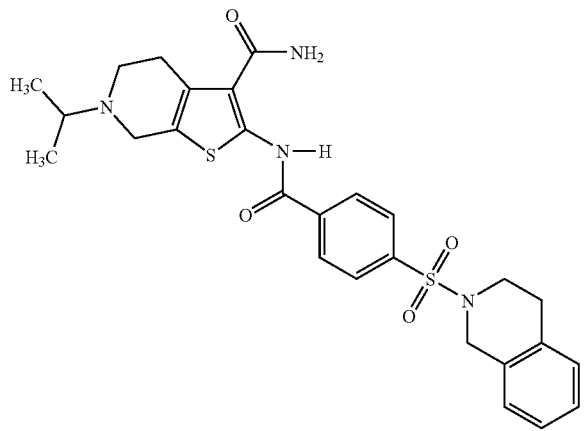 | | 13 |
| 2 | 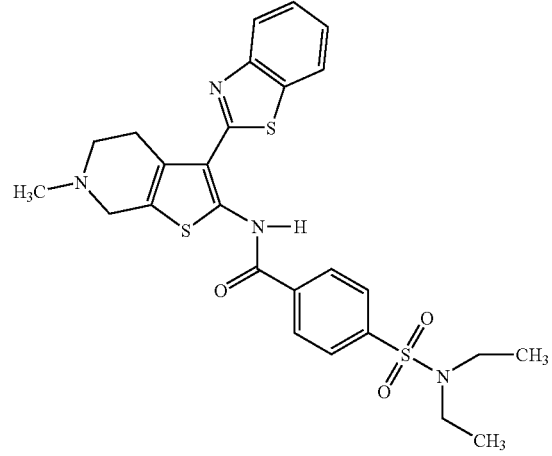 | 60 | |
| 3 | 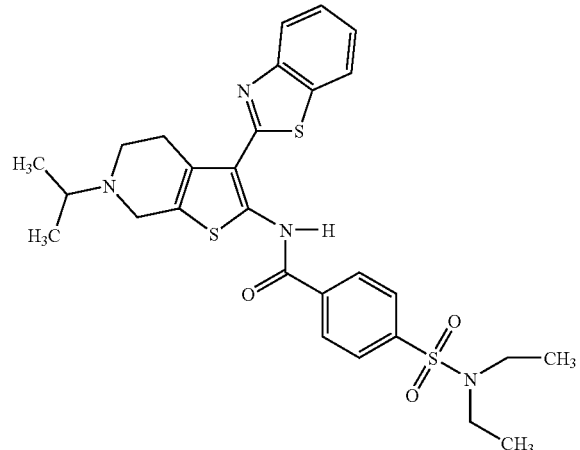 | | 10 |

TABLE 1-continued

Inhibition of L-Selectin Binding to Heparin by Selected Compounds

| Compound No. | Structure | % Inhibition at 50 µM | IC-50 [µM] |
|---|---|---|---|
| 4 | 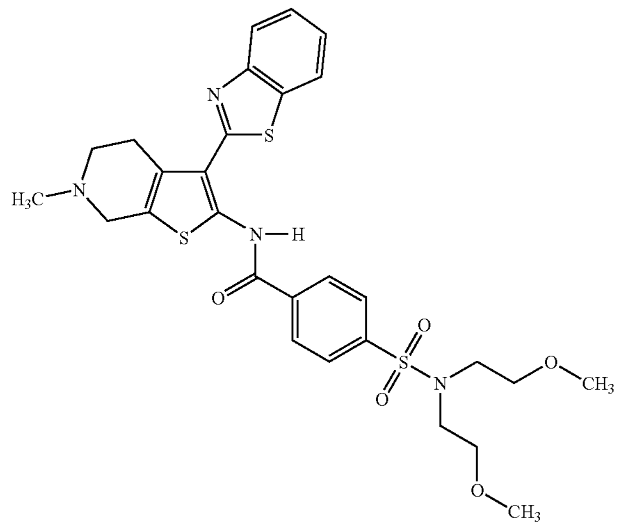 | 43 | |
| 5 | 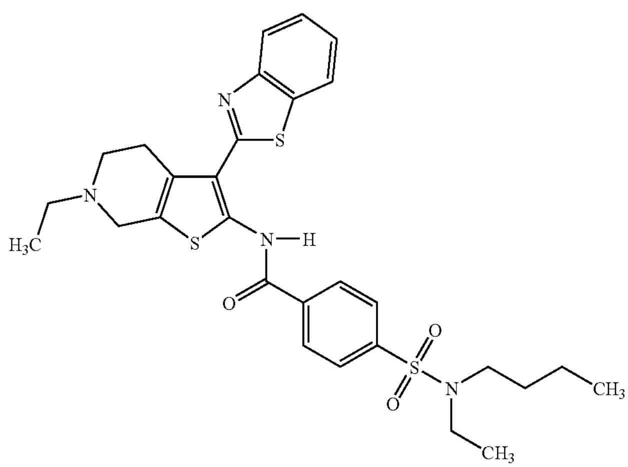 | 62 | |
| 6 | 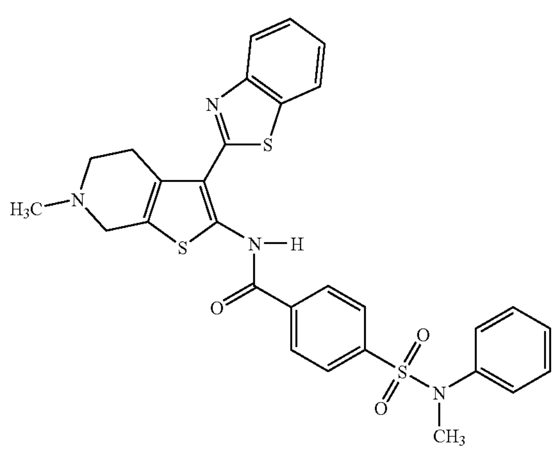 | 44 | |

TABLE 1-continued

Inhibition of L-Selectin Binding to Heparin by Selected Compounds

| Compound No. | Structure | % Inhibition at 50 μM | IC-50 [μM] |
|---|---|---|---|
| 7 | 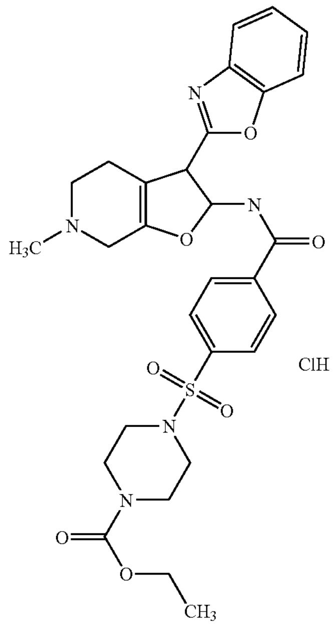 | | 19 |
| 8 | 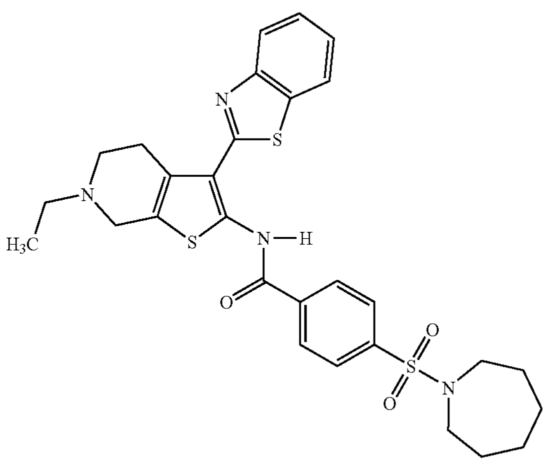 | | 46 |
| 9 | 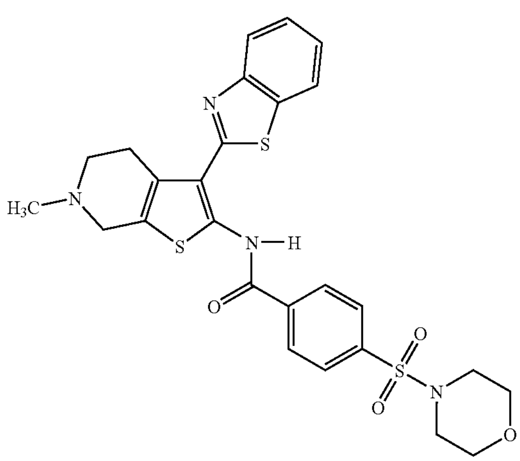 | | 52 |

TABLE 1-continued
Inhibition of L-Selectin Binding to Heparin by Selected Compounds
| Compound No. | Structure | % Inhibition at 50 μM | IC-50 [μM] |
|---|---|---|---|
| 10 | 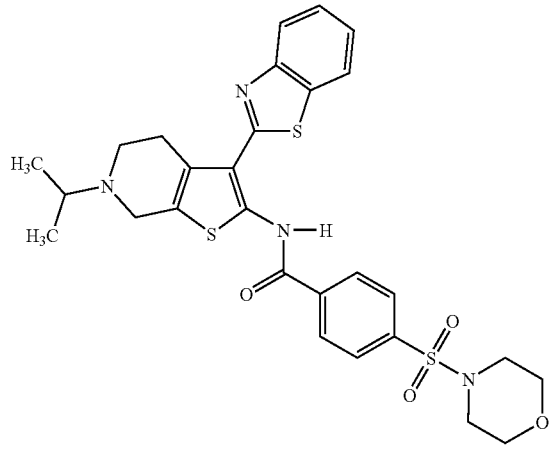 | | 25 |
| 11 | 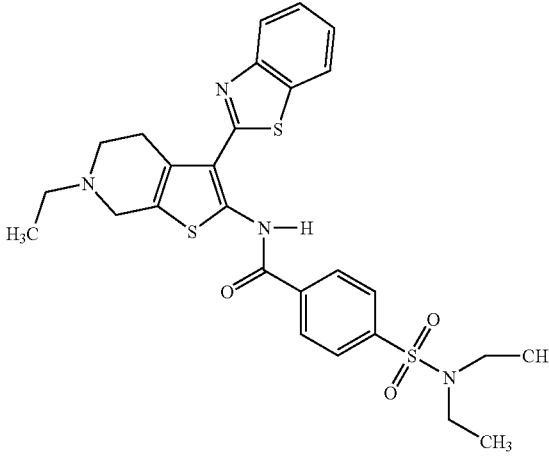 | | 0.35 |
| 12 | 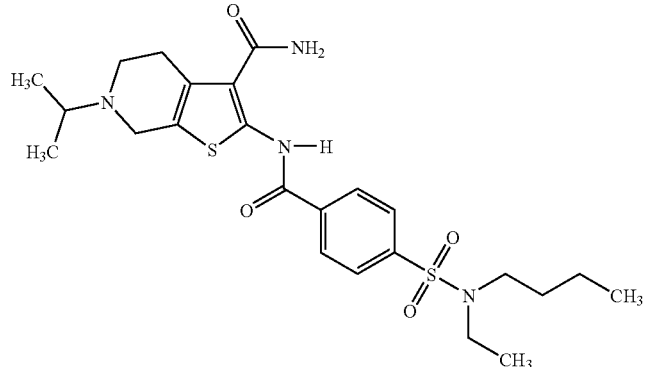 | | 55 |

TABLE 1-continued

Inhibition of L-Selectin Binding to Heparin by Selected Compounds

| Compound No. | Structure | % Inhibition at 50 μM | IC-50 [μM] |
|---|---|---|---|
| 13 | 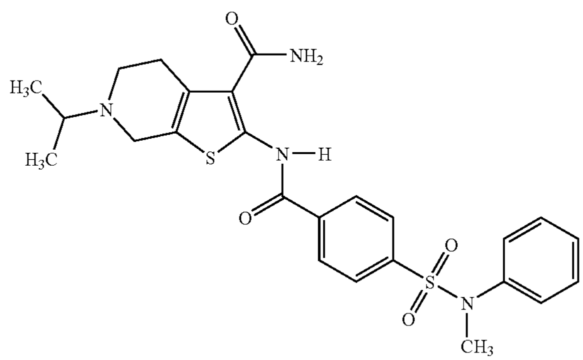 | | 68 |
| 14 | 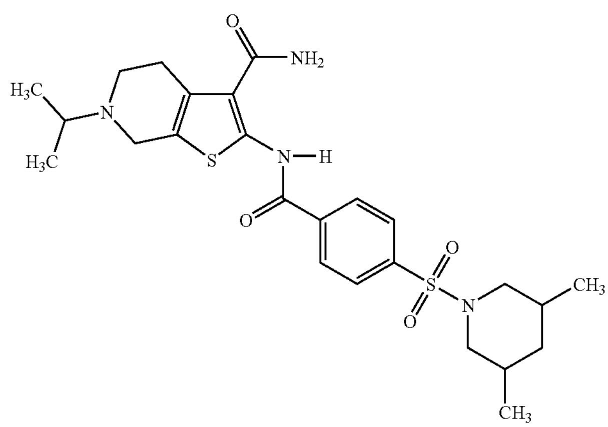 | | 35 |
| 15 | 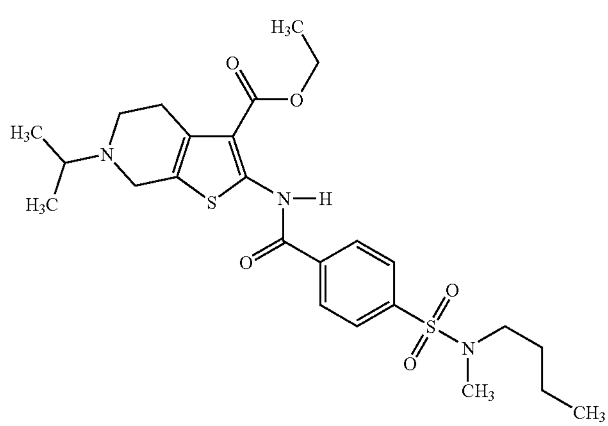 | | 40 |

TABLE 1-continued

Inhibition of L-Selectin Binding to Heparin by Selected Compounds

| Compound No. | Structure | % Inhibition at 50 μM | IC-50 [μM] |
|---|---|---|---|
| 16 | 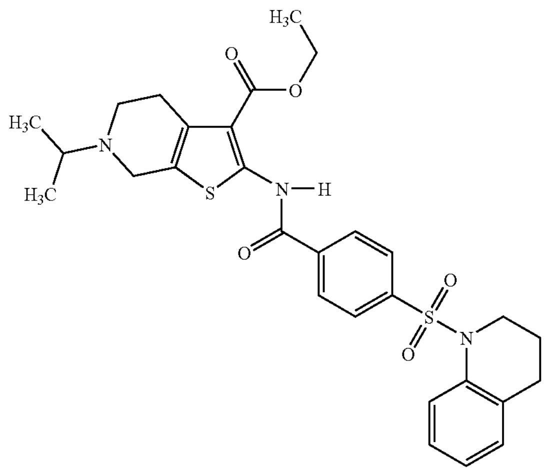 | | 11 |
| 17 | 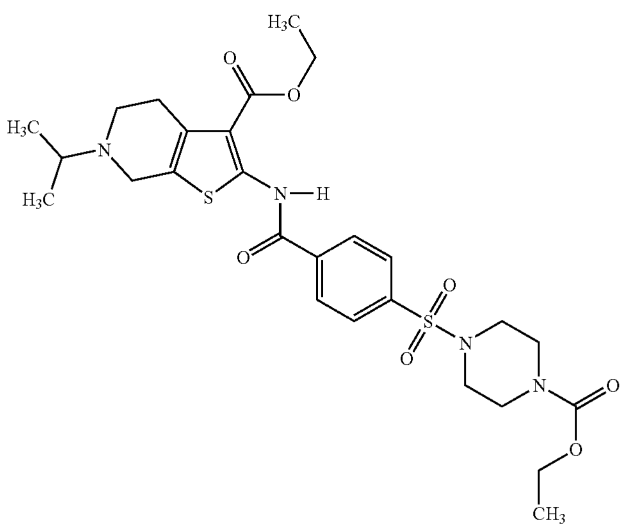 | | 21 |
| 18 | 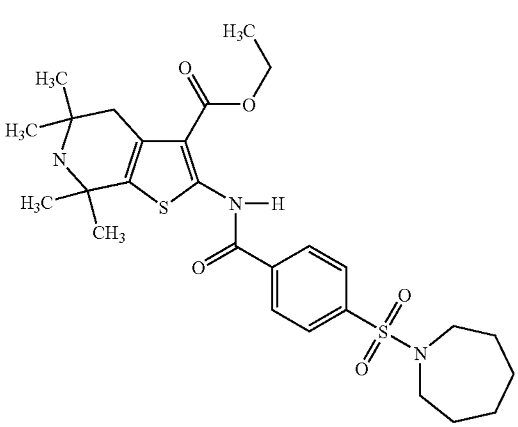 | | 11 |

TABLE 1-continued

Inhibition of L-Selectin Binding to Heparin by Selected Compounds

| Compound No. | Structure | % Inhibition at 50 μM | IC-50 [μM] |
|---|---|---|---|
| 19 | 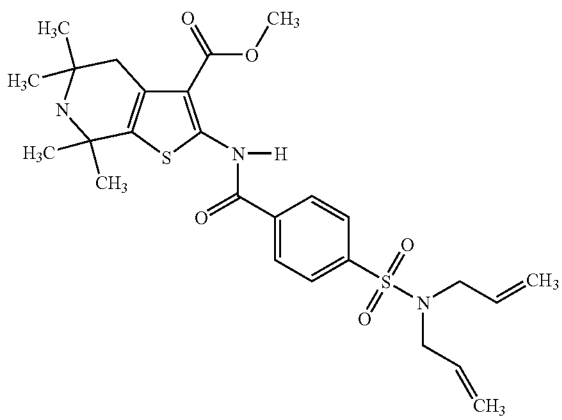 | | 43 |
| 20 | 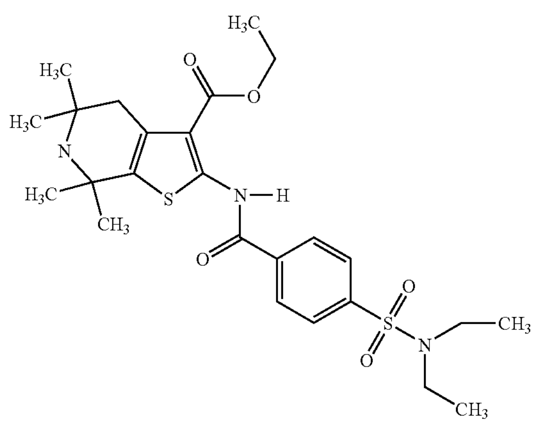 | | 26 |
| 21 | 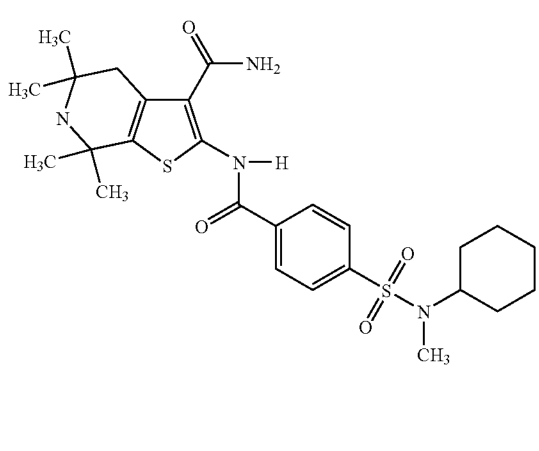 | | 36 |

TABLE 1-continued

Inhibition of L-Selectin Binding to Heparin by Selected Compounds

| Compound No. | Structure | % Inhibition at 50 μM | IC-50 [μM] |
|---|---|---|---|
| 22 | 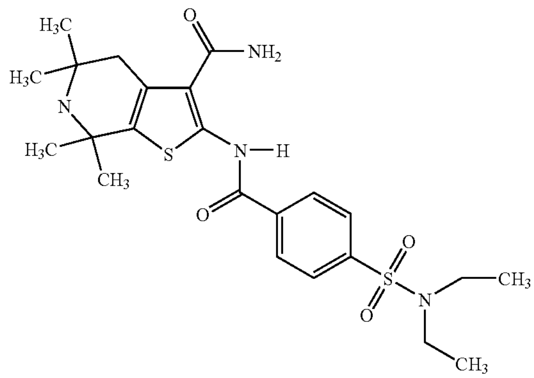 | 35 | |
| 23 | 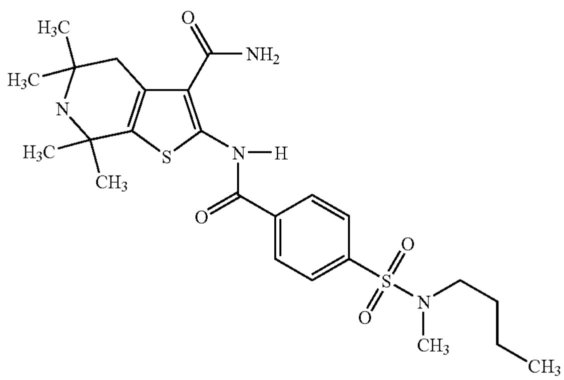 | 39 | |
| 24 | 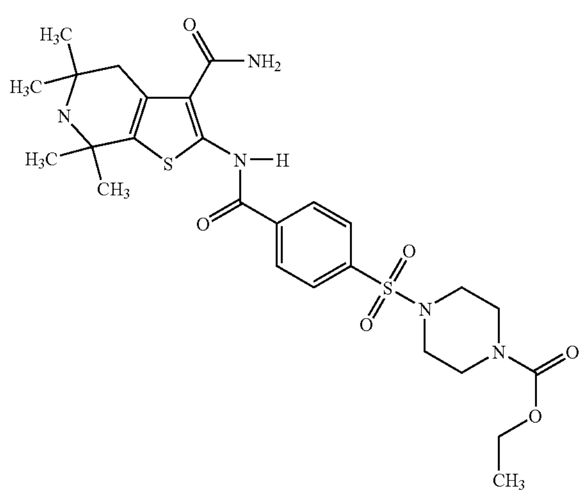 | 29 | |

TABLE 1-continued

Inhibition of L-Selectin Binding to Heparin by Selected Compounds

| Compound No. | Structure | % Inhibition at 50 μM | IC-50 [μM] |
|---|---|---|---|
| 25 | 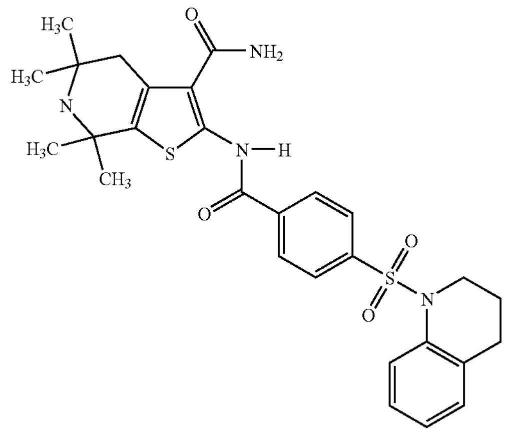 | | 12 |
| 26 | 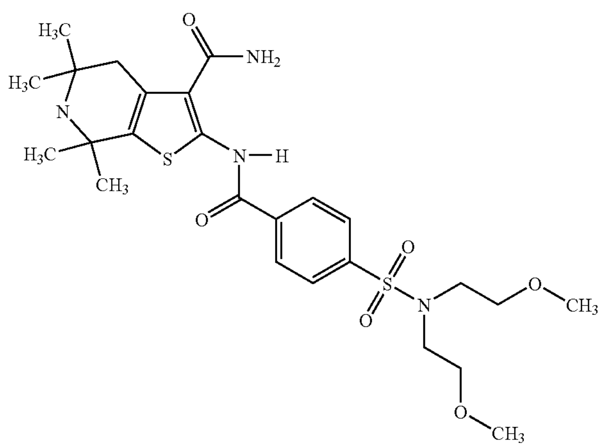 | | 23 |
| 27 | 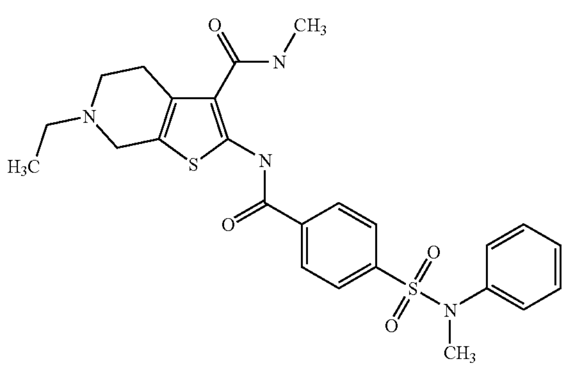 | | 9 |

TABLE 1-continued

Inhibition of L-Selectin Binding to Heparin by Selected Compounds

| Compound No. | Structure | % Inhibition at 50 µM | IC-50 [µM] |
|---|---|---|---|
| 28 | 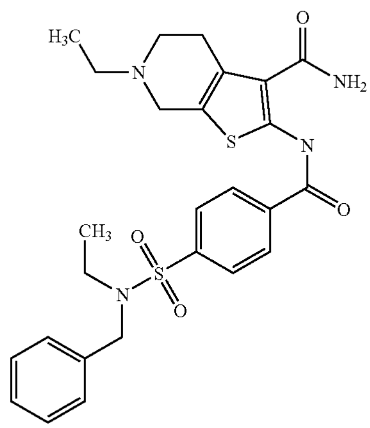 | 63 | |
| 29 | 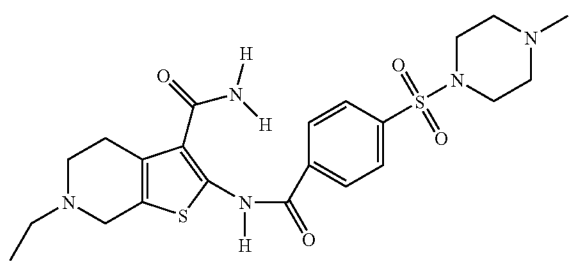 | 30 | |
| 30 | 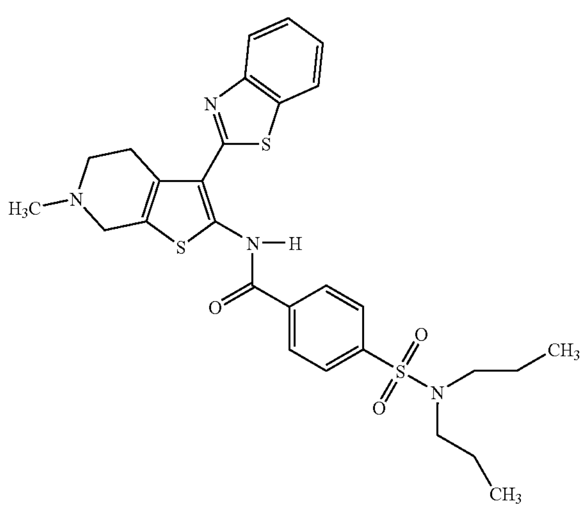 | 21 | |

TABLE 1-continued

Inhibition of L-Selectin Binding to Heparin by Selected Compounds

| Compound No. | Structure | % Inhibition at 50 μM | IC-50 [μM] |
|---|---|---|---|
| 31 | 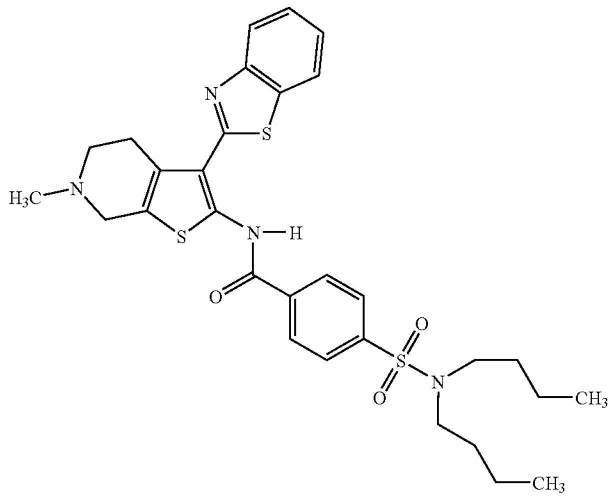 | | 27 |
| 32 | 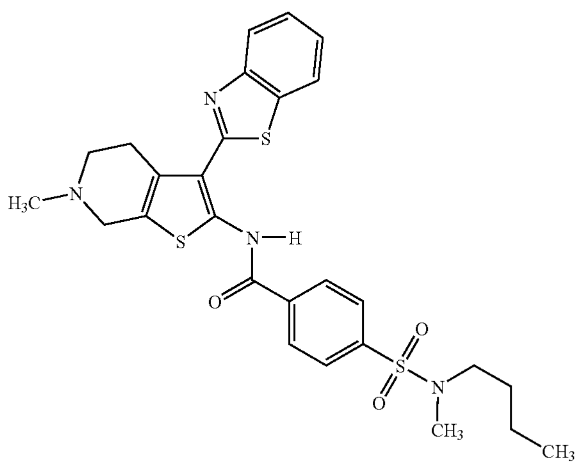 | | 26 |
| 33 | 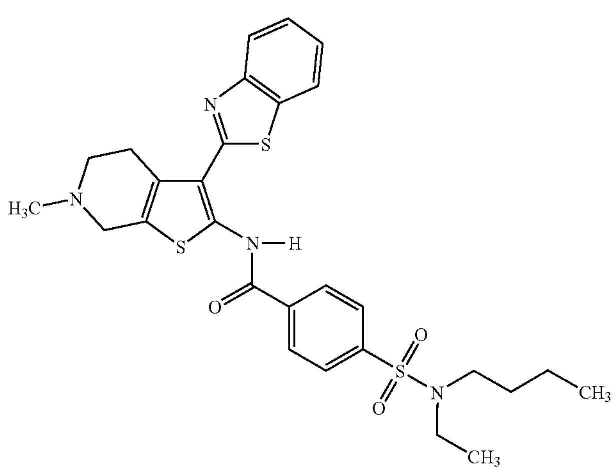 | | 21 |

TABLE 1-continued
Inhibition of L-Selectin Binding to Heparin by Selected Compounds
| Compound No. | Structure | % Inhibition at 50 μM | IC-50 [μM] |
|---|---|---|---|
| 34 | 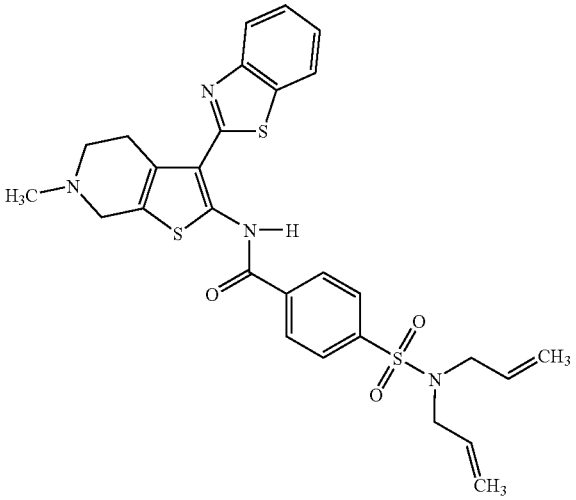 | | 25 |
| 35 | 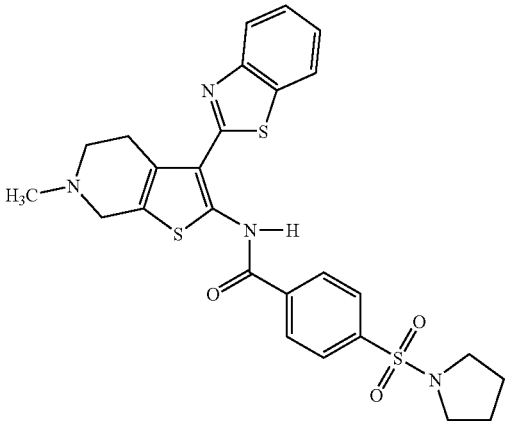 | | 24 |
| 36 | 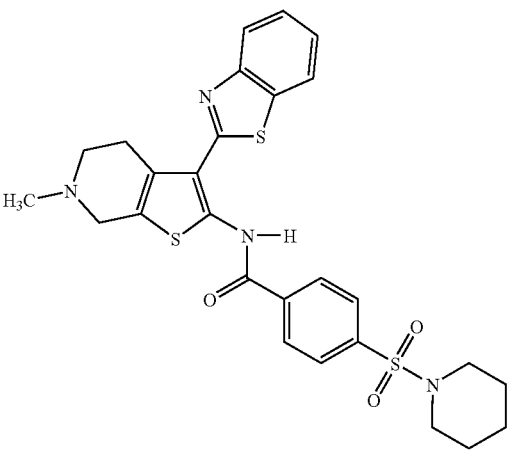 | | 26 |

TABLE 1-continued
Inhibition of L-Selectin Binding to Heparin by Selected Compounds
| Compound No. | Structure | % Inhibition at 50 μM | IC-50 [μM] |
|---|---|---|---|
| 37 | 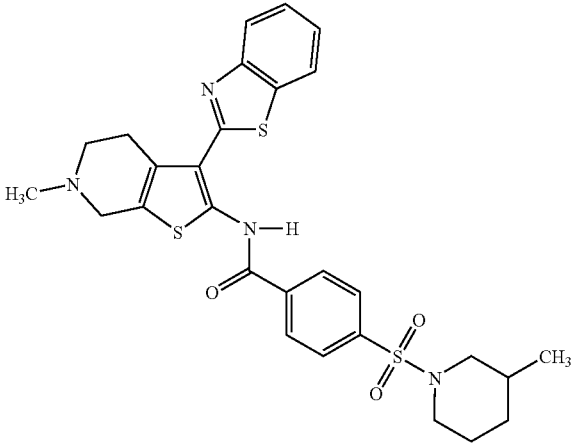 | | 23 |
| 38 | 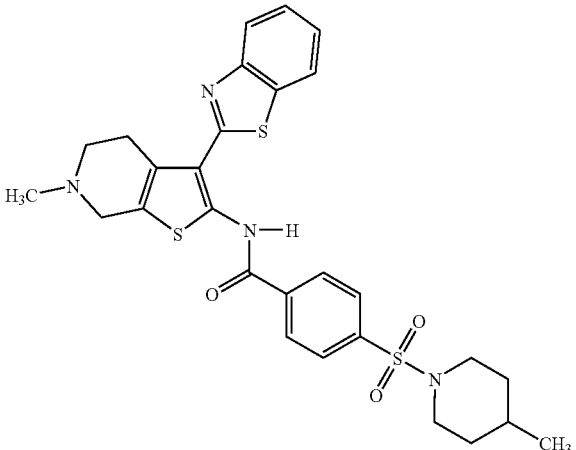 | | 33 |
| 39 | 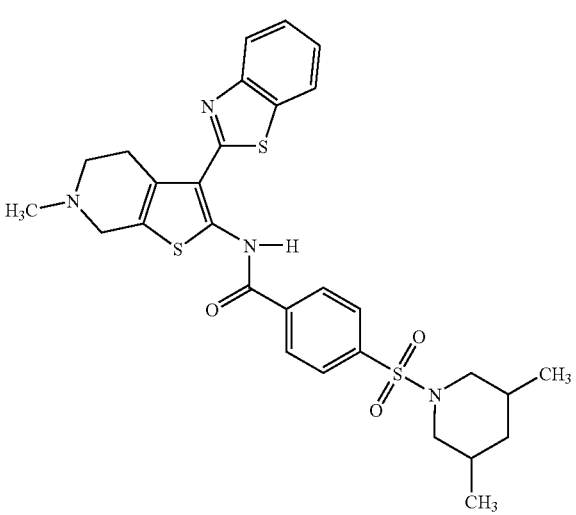 | | 24 |

TABLE 1-continued
Inhibition of L-Selectin Binding to Heparin by Selected Compounds
| Compound No. | Structure | % Inhibition at 50 μM | IC-50 [μM] |
|---|---|---|---|
| 40 | 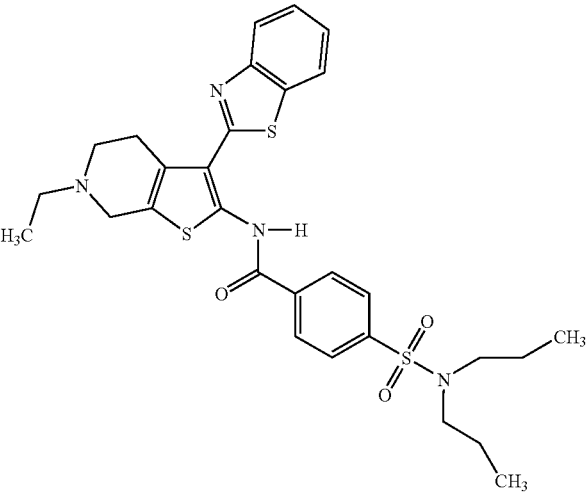 | 25 | |
| 41 | 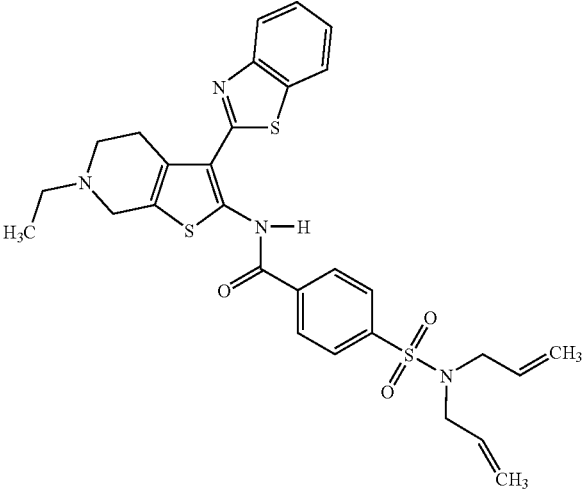 | 25 | |
| 42 | 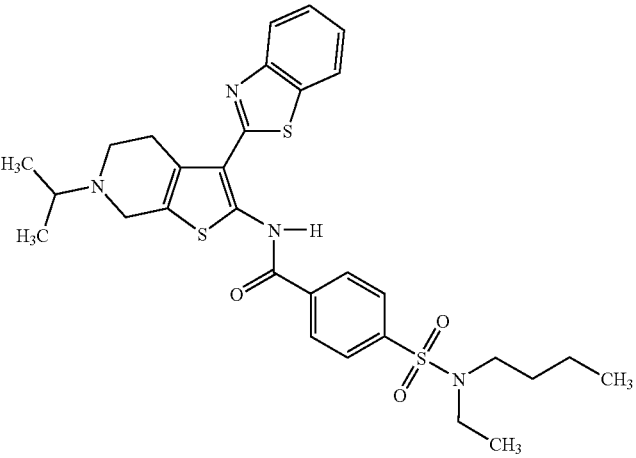 | 27 | |

TABLE 1-continued

Inhibition of L-Selectin Binding to Heparin by Selected Compounds

| Compound No. | Structure | % Inhibition at 50 μM | IC-50 [μM] |
|---|---|---|---|
| 43 | 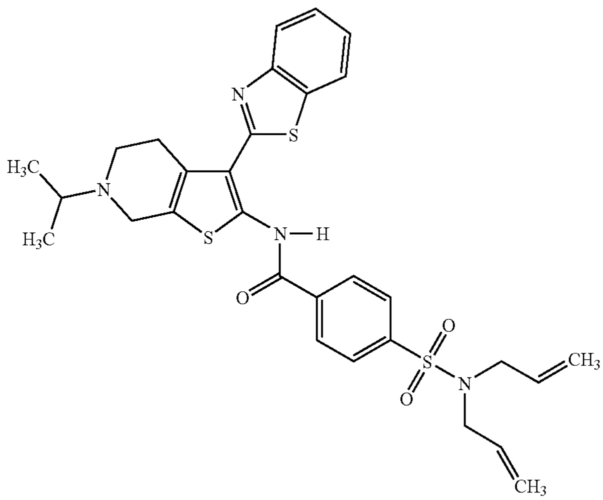 | | 17 |
| 44 | 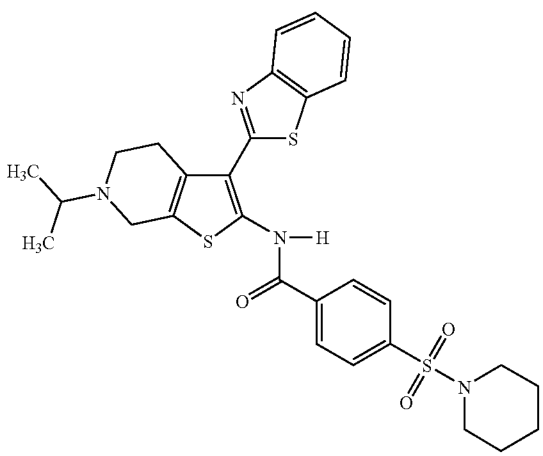 | | 29 |
| 45 | 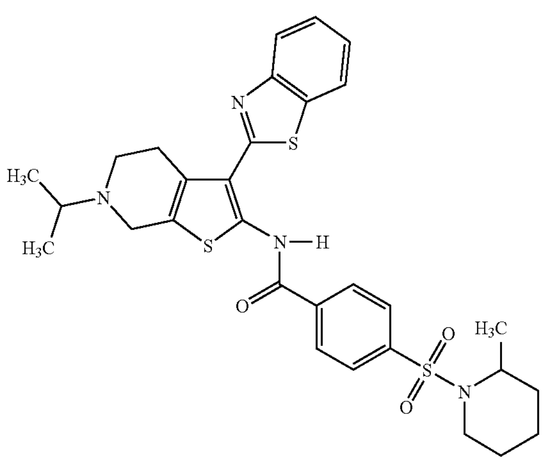 | | 24 |

All assays were repeated at least twice and representative results are shown.

Figure 8:
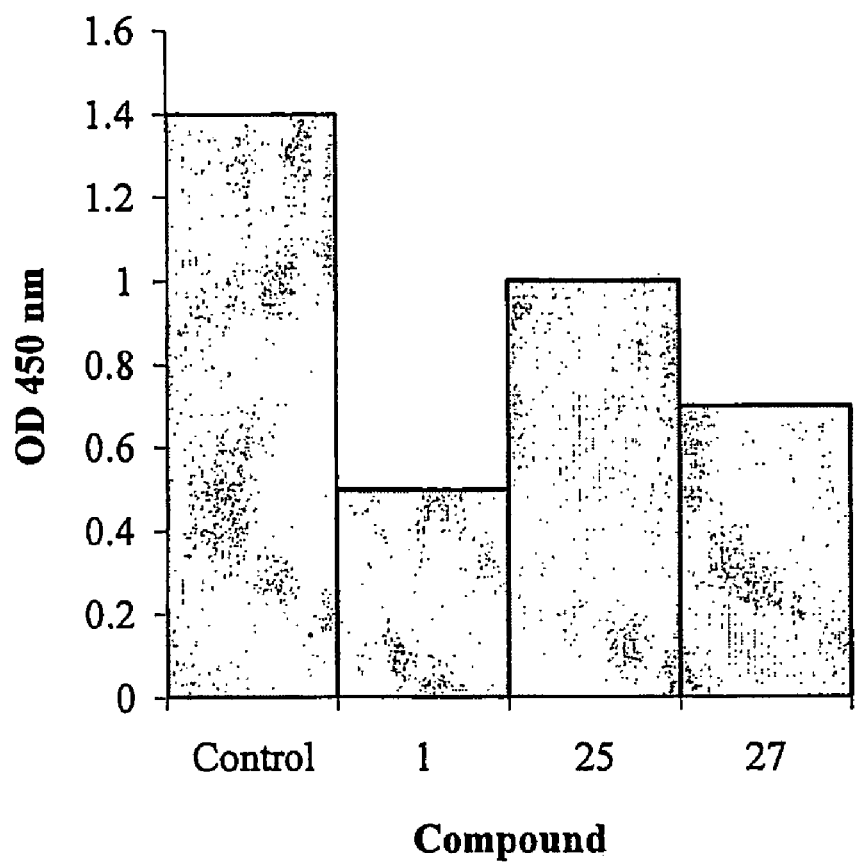
FIG. 8 shows inhibition of L-selectin binding to immobilized bovine kidney heparan sulfate by different inhibitor Compounds.

In addition, bovine kidney heparan sulfate (Sigma Cat. No. H7640) conjugated to Bovine Serum Albumin (Sigma Cat. No. A7638) was used in the in vitro assay as described herein above, to demonstrate L-selectin binding to HS-GAGs different from heparin, and to demonstrate inhibition of the binding by inhibitor compounds. FIG. 8 shows the inhibition of L-selectin binding to bovine kidney heparan sulfate by several different inhibitor compounds of formula I.

Example 6

Assays to Demonstrate Direct Interaction of Inhibitor Compounds with Heparin and Other HS-GAGs Assay 1.

In order to demonstrate that the L-selectin inhibitor Compounds indeed bind directly to heparin and other HS-GAGs, individual compounds were incubated with immobilized heparin in the absence of L-selectin as follows: 96 well ELISA plates were coated with Heparin-BSA, then blocked with BSA as described in Example 5. Inhibitor Compounds at final concentration 0.1-200 µM were incubated in the ELISA plate for 90 min, and then washed with incubation buffer. After washing, L-selectin/IgG was added to the wells pre-incubated with compounds. At the same time, in separate control wells, L-selectin was co-incubated with inhibitor Compounds for 90 min. Following the incubation, L-selectin bound to the plate was quantified by antibody conjugated to Horse Radish Peroxidase and OD measurement as performed as described in Example 5. Inhibitor Compounds No. 5 and No. 11 exerted the same level of inhibition on L-selectin binding to heparin in the pre-incubation or the co-incubation experiments.

Assay 2.

Figure 7:
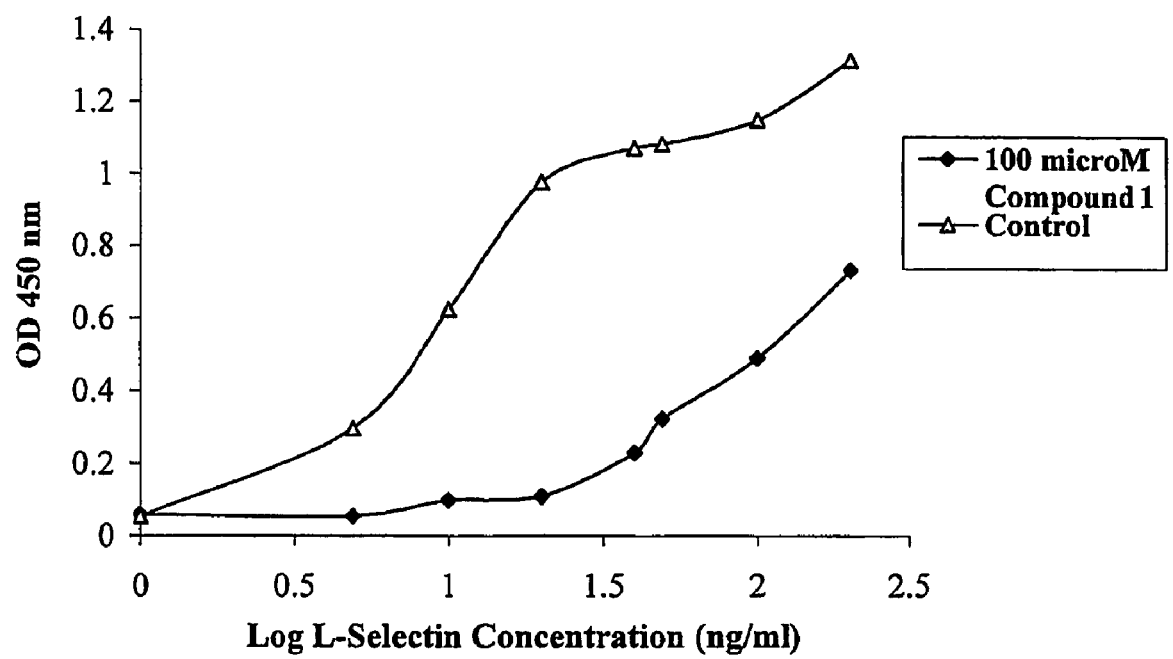
FIG. 7 shows the binding of L-selectin to immobilized heparin in the absence or presence of Compound no. 1 (100 μM).

Additional evidence for the direct binding of Inhibitor Compounds to heparin and other HS-GAGs was demonstrated by an extension of Assay 1. Ninety-six well ELISA plates were coated with Heparin-BSA, then blocked with BSA as described above. Inhibitor Compounds, at concentrations predetermined to inhibit L-selectin binding, were incubated in the ELISA plate for 60 min, and then washed with incubation buffer. After washing, L-selectin/IgG was added to the plate at increasing concentrations (5-250 µg/ml) and incubated for 90 minutes. Following the incubation, L-selectin bound to the plate was quantified by antibody conjugated to Horse Radish Peroxidase followed by optical density measurement as described in Example 5. Quantitative L-selectin binding was demonstrated at the higher L-selectin concentrations (50-250 µg/ml), demonstrating that the inhibitor Compounds prevented L-selectin binding to heparin, and therefore these results confirm that the inhibitor Compounds directly interact with heparin, the latter is thus an L-selectin receptor. An example is shown in FIG. 7. The dose response curve delineated with open triangles (Control) represents the results obtained after incubation of the plate with L-selectin in the absence of the inhibitor Compound no. 1.

Example 7

Inhibition of Leukocyte Adhesion to Endothelial Cells Under Shear Flow by Inhibitor Compounds Human T-lymphocytes were passed over a layer of human endothelial cells according to the method of Lawrence and Springer (Cell 65: 859-873, 1991). At high shear flow, migrating T-lymphocytes adhered transiently and intermittently to the endothelial cells as a consequence of HS-GAG-ECAM interaction. The resulting T-cell rolling was recorded by video camera and the number of rolling cells per defined area during a constant period of time was determined. Soluble heparin (competitor of cell surface GAGs) abolished T-cell rolling under high shear flow conditions. Compounds no. 1, 11 and 25, each at 25 µM, inhibited cell rolling by 90, 90 and 70%, respectively.

| Test Compound (TC) | % rolling |
|---|---|
| Assay Buffer | >60 |
| Heparin (5 µg/ml) | 0 |
| Compound no. 11 | <10 |
| Compound no. 25 | <10 |
| Compound no. 1 | 30 |

Example 8

A Model of Leukocyte and Neutrophil Infiltration into Mouse Peritoneum

BALB/c mice (6 weeks old, ~20 g in weight, 15 mice/group) received intraperitoneal injection of an inhibitor compound in 0.2 ml DMSO/Tween/sterile saline 1 hour before administration of thioglycollate (Sigma). Control groups received vehicle and sham controls received no thioglycollate. Mice were injected intraperitoneally with 1 ml of 3% thioglycollate broth (Xie, X. et al., J. Biol. Chem., 275, 34818-34825, 2000). Mice were sacrificed after 3 hours, and the peritoneal cavities were ravaged with 5 µl of ice-cold saline containing 2 mM EDTA to prevent clotting. After red blood cell lysis, leukocytes were counted in a hemocytometer. Neutrophils were counted after staining with Türck. Data was expressed as mean±SEM, and statistical analysis was performed by Student t test. A value of $P<0.05$ was taken to denote statistical significance.

Thioglycollate administration induced approximately 3-fold increase in leukocyte accumulation in the peritoneal cavity. Leukocyte migration into the peritoneal cavity was inhibited efficiently by administration of inhibitor compounds including Compound No. 5 and Compound no. 11. Similar results were obtained when the neutrophil counts were determined. Compound no. 5 was tested in more detail at three doses: 2 mg/kg, 10 mg/kg, and 50 mg/kg (FIG. 4). The compound was found to be a potent inhibitor of leukocyte migration; the infiltration was reduced by 75% at a dose of 50 mg/kg, by 50% at 10 mg/kg, and by 25% at 2 mg/kg. It is well known that leukocyte migration and infiltration in vivo is a hallmark of inflammatory, autoimmune and other disorders. The ability of the inhibitor compounds of the invention to inhibit leukocyte infiltration in vivo has therefore therapeutic applications for these disorders.

Example 9

Carrageenan-induced Paw Edema

Figure 5:
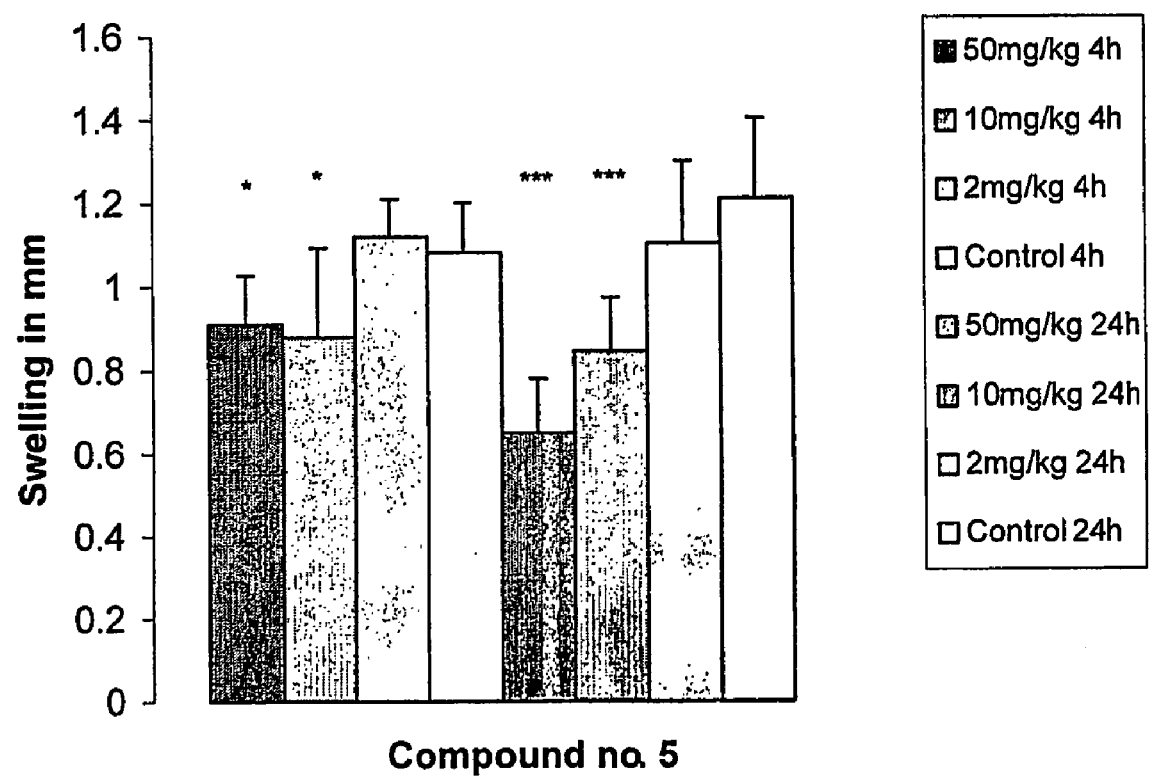
FIG. 5 demonstrates the anti-inflammatory properties of Compound no. 5 in Paw Edema.

Acute edema was induced in the left hind paw of Balb/c mice by injecting 0.02 ml of freshly prepared solution of 2% carrageenan after 60 min of test compound administration (Torres, S. R. et al., European Journal of Pharmacology 408: 199-211, 2000). The right paw received 0.02 ml of saline, which served as a control. Carrageenan was injected under the plantar region of right hind paw and the paw thickness was measured at 2, 4 and 24 hours after carrageenan challenge using a Mitutoyo engineer's micrometer expressed as the difference between right and left pad as mean±SEM. Inhibitor compounds significantly reduced carrageenan induced paw edema after i.p. administration. A dose response curve for Compound no. 5 is shown in FIG. 5. These results demonstrate that compounds inhibiting GAG binding to GAG-ECAMs display anti-inflammatory activity.

Example 10

Delayed-type Hypersensitivity (DTH)

Mice (15 animals per group) were sensitized by topical application of a 2% oxazolone (4-ethoxymethylene-2-phenyl-2-oxazoline-5-one; Sigma, St Louis, Mo.) solution in acetone/olive oil (4:1 vol/vol) to shaved abdomen (50 µl) and to each paw (5 µl) (Lange-Asschenfeldt B. et al., Blood 99:538-545, 2002). Five days after sensitization, right ears were challenged by topical application of 10 µl of a 1% oxazolone solution, whereas left ears were treated with vehicle alone. Compounds were administered 1 hr prior to challenge. The extent of inflammation was measured 24 hours after challenge, using the mouse ear-swelling test. The unpaired Student t test was used for statistical analyses.

Figure 6:
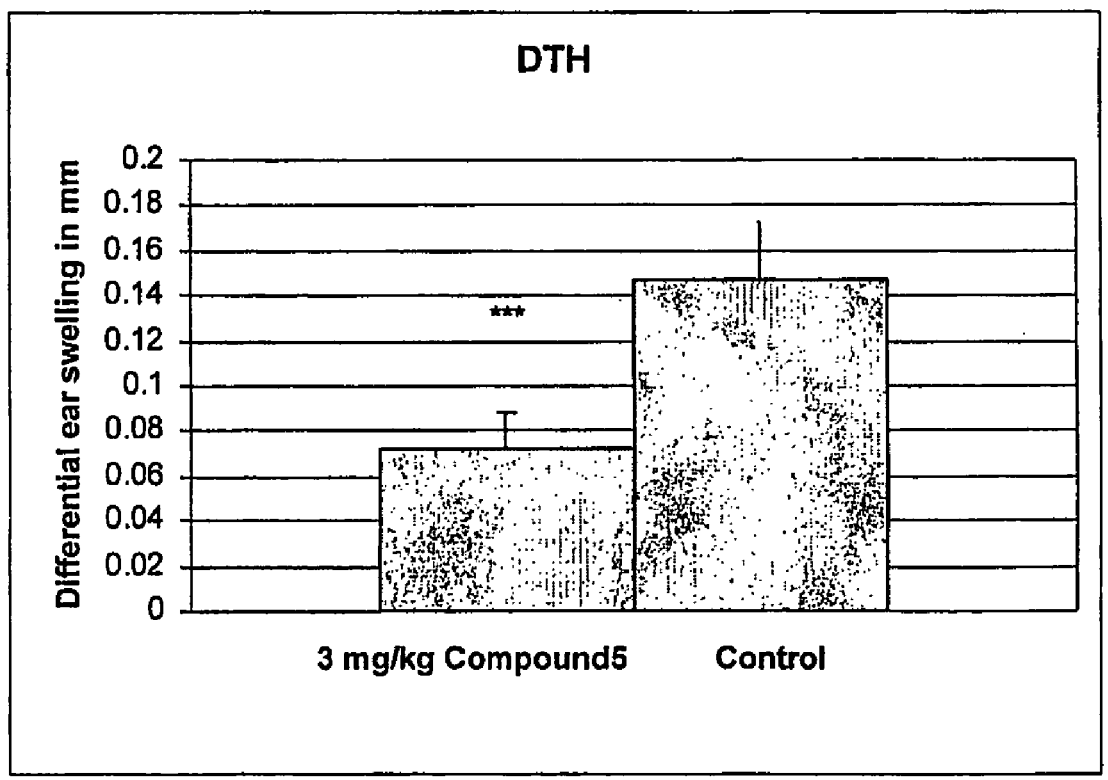
FIG. 6 demonstrates the anti-inflammatory properties of Compound no. 5 administered intravenously in a model of Delayed Type Hypersensitivity (DTH).

As illustrated in FIG. 6, Compound no. 5 (at a dose of 3 mg/kg, administered iv) inhibited DTH to 56% of control value 24 hours after challenge. Data were statistically significant at $p>0.001$.

Example 11

Trinitrobenzine Sulfonic Acid (TNBS) Induced Colitis

Control mice (12 per group) were injected intraperitoneally (IP) with Test Compound (TC) Vehicle (Tween 80, 5%, 200 µl). Experimental mice (12 per group) were injected IP with TC (10 mg/kg, or 35 mg/kg in 200 µl). The control and experimental mice were injected once per day for 7 successive days. 24 hours after the first IP injection, Inflammatory Bowel Disease (IBD) was induced in the control, experimental, and in an untreated group by intra-rectal administration of TNBS (150 mg/kg dissolved in NaCl (0.9%): EtOH (50%) (1:1; 80 µl mouse). All of the mice were killed by cervical dislocation 7 days after TNBS administration. The colons of the mice were examined under a dissecting microscope (X5) to evaluate the macroscopic lesions on a scale of 0 to 10 (Colonic damage score). As shown in FIG. 9, inhibitor Compound no. 11 significantly inhibited the colonic damage at doses of 10 and 35 mg/kg. FIG. 10 shows the effect of oral administration of Compound no. 11 in the same experimental model. The compound was administered once a day for 7 days in a suspension with 0.5% methylcellulose per os. There were 12 mice per group and the control mice received 0.5% methylcellulose only. Compound no. 11 significantly inhibited the colonic damage at doses of 3, 50 and 100 mg/kg per os (FIG. 10).

Example 12

Experimental Autoimmune Encephalomyelitis (EAE)

In autoimmune conditions, T cells reactive to self-antigens escape elimination in the thymus and are activated in the periphery, where they can provoke damage in specific organs. EAE, a model of autoimmune disease that is induced in Lewis rats, bears many similarities to the human disease Multiple Sclerosis (MS). T cells found in brain lesions of MS patients have TCR junctional rearrangements that are identical to T cells found in the spinal cords of Lewis rats immunized with a peptide of myelin basic protein MBP p87-99. In addition, a major T and B cell response in MS patients is directed to MBP p87-99.

EAE is induced in rats by immunization with MBP p87-99. The inhibitor Compounds are administered once daily by intra-peritoneal injection for 3 consecutive days starting 1 day before the appearance of EAE symptoms (day 12 after EAE induction). The degree of clinical disease is scored as follows: 0=no signs; 1=loss of tail tonicity; 2=paralysis of hind limbs; 3=paralysis of all four limbs 4=quadriplegic animal in a moribund state. As shown in FIG. 11, Compound no. 11 significantly inhibited clinical signs of EAE at a dose of 10 and 35 mg/kg.

Example 13

Inhibition of Growth of Cancer Cell Lines

Each cell line (MCF7 (Breast carcinoma), NCI-H460 (Non-small cell lung carcinoma), and SF-268 (glioma) was pre-incubated on a microtiter plate. Inhibitor compounds were then added at a concentration of 0.1 µM and the culture incubated for 48 hours. End-point determinations were made with alamar blue (Gray G D, Wickstrom E, Biotechniques 21(5) 780-782, 1996). Results for each compound are presented as the percent of growth of the treated cells as compared to the untreated cells. Compounds, which reduce the growth of any one of the cell lines to approximately 32% or less were considered suitable for further and more extensive study (Monks A et al, J. Natl. Cancer Inst., 83:757-766, 1991. Compound no. 1 inhibited the growth of the cell lines MCF7, NCI-H460, and SF-268 by 99%, 100% and 99%, respectively.

Example 14

Inhibition of Leukemia Cell Growth

Each cell line (RPMI-8226 (Multiple Myeloma), MOLT-4 (Acute lymphoblastic leukemia), CCR-CEM (Human T Cell leukemia), K562 (Chronic myeloid leukemia), SR (Chronic myeloid leukemia) was pre-incubated on a microtiter plate (Monks A et al, J. Natl. Cancer Inst., 83:757-766, 1991). Inhibitor compounds were then added at different concentrations ($10^{-8}$-$10^{-4}$ Molar) and the culture incubated for 48 hours. A sulforhodamine B (SRB) protein assay was used to estimate cell viability or growth (Skehan P et al, J. Natl. Cancer Inst., 82:1107-1112, 1990). Compound no. 1 inhibited the growth of the cell lines RPMI-8226, MOLT4, CCR-CEM, K562 and SR to 100%, 100%, 100%, 100% and 93%, respectively. There was negligible cell death (less than 15%).

Example 15

Methods to Measure the Counteracting Actions of Beparin and Other Anticoagulant GAGs on Coagulation Assay 1. Methods for in vitro Determinations of the Effects of Inhibitor Compound on Reversal of Factor Xa Activity.

Solutions of Lovenox (Rhone Poulenc Rohrer), Orgaran (Organan), or unfractionated heparin (Sigma) are prepared in 0.32% sodium citrate or in normal human plasma to contain 0.5 U/ml anti Factor Xa activity. Calibrations are made against the standards provided by the Stachrom Heparin (Diagnostica Stago) assay kit (Dignac M et al, Nouv. Res. Fr Hematol. 35:545-549, 1994). The heparin/ATIII complex is allowed to form at 37° C. for 2 minutes, inhibitor Compound is added, the mixture is incubated for an additional 1-5 minutes, then Factor Xa is added, and finally the chromogenic substrate is added for 1 minute, and the absorbance is read at 405 nm. The increase in absorbance of the heparinized control vs. that of the test sample is divided by the difference in the absorbance at 405 between the heparinized control and the control without heparin to obtain the % reversal.

Assay 2. In vitro Effect of the Inhibitor Compound on Reversal of Inhibition of Thrombin Activity by Unfractionated Heparin.

Plasma is obtained from normal donors. Thrombin concentration (human alpha thrombin, Enzyme Research Laboratories, South Bend, Ind.) is standardized to produce a clotting time of 20-22 seconds. Heparin is added at 0.5 IU anti-thrombin activity/ml. The clotting time for heparin alone is approximately 3 minutes. To test the effects of the compounds in this system, one minute after addition of heparin to the plasma, the compounds are added in concentrations ranging from 0.1-100 µM. After one minute, thrombin is added and the clotting time is determined.

Assay 3. In vivo Effects of Inhibitor Compounds in Reversing Effects of Lovenox on Factor Xa Activity.

Rats (300-400 gm) are anesthetized with ketamine/acepromazine and are cannulated in the left jugular vein and right femoral vein. Blood is drawn immediately before injection of Lovenox to establish baseline Factor Xa activity. Lovenox (43 IU anti-FXa activity/kg in 0.1 ml saline, based on suggested dosage for humans) is injected through the jugular catheter, followed immediately by 0.2 ml of saline. Blood (0.1 ml) is collected into sodium citrate from the femoral vein every 30 seconds for 3 min. The compound is injected at 3 min through the jugular catheter in 0.1 ml of phosphate-buffered saline, followed by a 0.2 ml saline flush. Compounds are administered and blood collection is immediately resumed every 30 seconds until 10 minutes after the initial Lovenox injection, then at 15, 20, 25 and 30 min. The samples are centrifuged to obtain plasma and are assayed for residual Lovenox by assay of anti-Factor Xa activity by the Stachrom Heparin test kit. Absorbance at 405 nm is measured after a 1-minute incubation with the chromogenic Factor Xa substrate.

It will be appreciated by persons skilled in the art that the present invention is not limited by what has been particularly shown and described herein above. Rather the scope of the invention is defined by the claims that follow.

The invention claimed is:

1. A thieno[2,3-c]pyridine compound of the formula 2-[[4-[[ethyl(phenylmethyl)amino]sulfonyl]benzoyl]amino]-6-ethyl-4,5,6,7-tetrahydrothieno[2,3-c]pyridine-3-carboxamide.

2. A thieno[2,3-c]pyridine compound of the formula 2-[[4-[(4-methyl-1-piperazinyl)sulfonyl]benzoyl]amino]-6-ethyl-4,5,6,7-tetrahydrothieno[2,3-c]pyridine-3-carboxamide.

3. A pharmaceutical composition comprising as an active ingredient a compound of the general formula I:

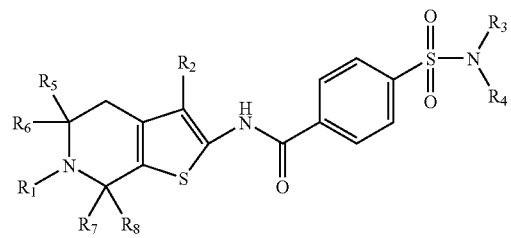

wherein:
$R_1$ is selected from the group consisting of H; straight or branched alkyl of 1-6 carbon atoms; arylalkyl; substituted arylalkyl; cycloalkyl, optionally substituted with alkyl groups; alkanoyl; arylcarbonyl optionally substituted at the aryl group; cycloalkylcarbonyl; alkoxycarbonyl;

$R_2$ is selected from the group consisting of aminocarbonyl; alkylaminocarbonyl; arylaminocarbonyl optionally substituted at the aryl group; dialkylaminocarbonyl wherein each alkyl is straight or branched chain $C_1$-$C_6$ alkyl or both alkyl groups together may form a 3-7 membered saturated, unsaturated or aromatic monocyclic or bicyclic nitrogen containing heterocyclyl, optionally containing one or two additional heteroatoms; benzothiazol-2-yl;

$R_3$ and $R_4$ are selected from the group consisting of $C_1$-$C_6$ alkyl, optionally substituted by hydroxy, alkoxy, amino or alkylamino, $C_2$-$C_4$ monounsaturated alkenyl, cycloalkyl, aryl, arylmethyl, or $R_3$ and $R_4$ together may form an optionally substituted 5-7 membered saturated, monocyclic nitrogen containing heterocyclyl, optionally containing one or two additional heteroatoms, or $R_3$ and $R_4$ together may form an optionally substituted 5-7 membered unsaturated or aromatic monocyclic or bicyclic nitrogen containing heterocyclyl, optionally containing one or two additional heteroatoms;

$R_5$, $R_6$, $R_7$ and $R_8$ are selected from the group consisting of H or $C_1$-$C_6$ alkyl, with the proviso that when $R_5$, $R_6$, $R_7$ and $R_8$ are $C_1$-$C_6$ alkyl, $R_1$ is hydrogen;

and pharmaceutically acceptable salts thereof; further comprising a pharmaceutically acceptable diluent or carrier.

4. The pharmaceutical composition according to claim 3, wherein $R_1$ is selected from the group consisting of methyl, ethyl, 1-methylethyl, phenylmethyl, acetyl, ethoxycarbonyl and $R_5$=$R_6$=$R_7$=$R_8$ are hydrogens.

5. The pharmaceutical composition according to claim 3, wherein $R_6$ is hydrogen and $R_5$=$R_6$=$R_7$=$R_8$ are hydrogens or methyl groups.

6. The pharmaceutical composition according to claim 3, wherein $R_1$=$R_5$=$R_6$ is methyl and $R_7$=$R_8$ are hydrogens.

7. The pharmaceutical composition according to claim 3, wherein $R_2$ is selected from the group consisting of aminocarbonyl, methylaminocarbonyl, dimethylaminocarbonyl, pyrrolidinylcarbonyl, piperidinylcarbonyl, morpholinylcarbonyl, benzothiazol-2-yl.

8. The pharmaceutical composition according to claim 3, wherein $R_3$ and $R_4$ are selected from the group consisting of methyl, ethyl, propyl, butyl, methoxyethyl, chlorobutyl, cyanoethyl, phenyl, cyclopentyl, cyclohexyl, phenylmethyl, allyl or crotyl, $R_3$ and $R_4$ may be equal or different.

9. The pharmaceutical composition according to claim 3, wherein $R_3$ and $R_4$ form pyrrolidine, piperidine, 2-methyl, 3-methyl, 4-methyl or 3,5-dimethyl piperidine, perhydroazepine, morpholine, piperazine, 4-methylpiperazine, 3,4-dihydro-2(1H)-isoquinolinyl, 3,4-dihydro-1(2H)quinoline, and substituted derivatives thereof.

10. The pharmaceutical composition according to claim 3 wherein the compound of Formula I is selected from:
- 2-[[4-[(ethylbutylamino sulfonyl]benzoyl]amino]-3-(benzothiazol-2-yl)-6-ethyl-4,5,6,7-tetrahydrothieno[2,3-c]pyridine;
- 2-[[(4-(3,4-dihydro-2(1H)-isoquinolinyl)sulfonyl]benzoyl]amino]-6-(1-methylethyl)-4,5,6,7-tetrahydrothieno[2,3-c]pyridine-3-carboxamide;
- 2-[[4-(methyiphenylamino)sulfonyl]benzoyl]amino]-6-(1-methylethyl)-4,5,5,7-tetrahydrothieno[2,3-c]pyridine-3-carboxamide;
- 2-[[4-(3,4-dihydro-2(1H)-isoquinolinyl)sulfonyl]benzoyl]amino]-4,5,5,7-tetrahydro-5,5,7,7-tetramethylthieno[2,3-c]pyridine-3-carboxamide; 2-[[4-[(diethylamino)sulfonyl]benzoyl]amino]-3-(benzothiazol-2-yl)-6-ethyl-4,5,5,7-tetrahydrothieno[2,3-c]pyridine;
- 2-[[4-(morpholinylsulfonyl)benzoyl]amino]-3-(benzothiazol-2-yl)-6-(1-methylethyl)-4,5,6,7-tetrahydrothieno[2,3-c]pyridine;
- 2-[[4-(3,4-dihydro-1(2H)-quinolinyl)sulfonyl]benzoyl]amino]-3-(benzothiazol-2-yl)-4,5,6,7-tetrahydro-5,5,7,7-tetramethylthieno[2,3-c]pyridine;
- 2-[[4-[[4-(methyl)-1-piperazinyl]sulfonyl]benzoyl]amino]-3-(benzothiazol-2-yl)-6-methyl-4,5,5,7-tetrahydrothieno[2,3-c]pyridine;
- 2-[[4-[(methylphenylamino)sulfonyl]benzoyl]amino]-3-(benzothiazol-2-yl)-6-methyl-4,5,6,7-tetrahydrothieno[2,3-c]pyridine;
- 2-[[4-(morpholinylsulfonyl)benzoyl]amino]-3-(benzothiazol-2-yl)-6-methyl-4,5,6,7-tetrahydrothieno[2,3-c]pyridine;
- 2-[[4-[[4-(3-methyl-1-piperidinyl)]sulfonyl]benzoyl]amino]-3-(benzothiazol-2-yl)-6-methyl4,5,6,7-tetrahydrothieno[2,3-c]pyridine;
- 2-[[4-[(diethylamino)sulfonyl]benzoyl]amino]-3-(benzothiazol-2-yl)-6-(phenylmethyl)-4,5,6,7-tetrahydrothieno[2,3-c]pyridine;
- 2-[[4-[(diethylamino)sulfonyl]benzoyl]amino]-3-(benzothiazol-2-yl)-6-methyl4,5,6,7-tetrahydrothieno[2,3-c]pyridine;
- 2-[[4-[[4-(ethoxycarbonyl)-1-piperazinyl]sulfonyl]benzoyl]amino]-4,5,6,7-tetrahydro-5,5,7,7-tetramethylthieno[2,3-c]pyridine-3-carboxamide;
- 2-[[4-[(cyclohxylmethylamino)sulfonyl]benzoyl]amino]-4,5,6,7-tetrahydro-5,5,7,7-tetramethylthieno[2,3-c]pyridine-3-carboxamide;
- 2-[[4-[(di-2-methoxyethylamino)sulfonyl]benzoyl]-4,5,6,7-tetrahydro-5,5,7,7-tetramethylthieno[2,3-c]pyridine-3-carboxamide;
- 2-[[4-[(diethylamino)sulfonyl]benzoyl]amino]-3-(benzothiazol-2-yl)-6-methyl-4,5,6,7-tetrahydrothieno[2,3-c]pyridine;
- 2-[[4-[(diethylamino)sulfonyl]benzoyl]amino]-3-(benzothiazol-2-yl)-6-(1-methylethyl)-4,5,6,7-tetrahydrothieno[2,3-c]pyridine;
- 2-[[4-[(di-2-methoxyethylamino)sulfonyl]benzoyl]amino]-3-(benzothiazol-2-yl)-6-methyl-4,5,6,7-tetrahydrothieno[2,3-c]pyridine;
- 2-[[4-[(methylphenylamino)sulfonyl]benzoyl]amino]-3-(benzothiazol-2-yl)-6-methyl-4,5,6,7-tetrahydrothieno[2,3-c]pyridine;
- 2-[[4-[[4-(ethoxycarbonyl)-1-piperazinyl]sulfonyl]benzoyl]amino]-3-(benzothiazol-2-yl)-6-methyl-4,5,6,7-tetrahydrothieno[2,3-c]pyridine;
- 2-[[4-(diethylamino)sulfonyl]benzoyl]amino]-4,5,6,7-tetrahydro-5,5,7,7-tetramethylthieno[2,3-c]pyridine-3-carboxamide;
- 2-[[4-[(methylphenylamino)sulfonyl]benzoyl]amino]-6-ethyl-4,5,6,7-tetrahydrothieno[2,3-c]pyridine-3-carboxylic acid methylamide;
- 2-[[4-[[ethyl(phenylmethyl)amino]sulfonyl]benzoyl]amino]-6-ethyl-4,5,6,7-tetrahydrothieno[2,3-c]pyridine-3-carboxamide;
- 2-[[4-[(4-methyl-1-piperazinyl)sulfonyl]benzoyl]amino]-6-ethyl-4,5,6,7-tetrahydrothieno[2,3-c]pyridine-3-carboxamide;
- 2-[[(4-(3,4-dihydro-1(2H)-quinolinyl)sulfonyl]benzoyl]amino]-6-ethyl-4,5,6,7-tetrahydrothieno[2,3-c]pyridine-3-carboxylic acid methylamide;
- 2-[[4-[(4-methyl-1-piperazinyl)sulfonyl]benzoyl]amino]-6-ethyl-4,5,6,7-tetrahydrothieno[2,3-c]pyridine-3-carboxylic acid methylamide;
- 2-[[4-[(4-methyl-1-piperazinyl)sulfonyl]benzoyl]amino]-3-(benzothiazol-2-yl)-6-ethyl-4,5,6,7-tetrahydrothieno[2,3-c]pyridine;
- 2-[[4-(diethylamino)sulfonyl]benzoyl]amino]-6-ethyl-4,5,6,7-tetrahydrothieno[2,3-c]pyridine-3-carboxylic acid N-methylamide;
- 2-[[4-(diethylamino)sulfonyl]benzoyl]amino]-6-ethyl-4,5,6,7-tetrahydrothieno[2,3-c]pyridine-3-carboxylic acid morpholinylamide.

11. The pharmaceutical composition according to claim 10 wherein the compound of formula I is:
- 2-[[4-[(ethylbutylamino)sulfonyl]benzoyl]amino]-3-(benzothiazol-2-yl)-6-ethyl-4,5,6,7-tetrahydrothieno[2,3-c]pyridine.

12. The pharmaceutical composition according to claim 10 wherein the compound of formula I is:
- 2-[[4-[(diethylamino)sulfonyl]benzoyl]amino]-3-(benzothiazol-2-yl)-6-ethyl-4,5,6,7-tetrahydrothieno[2,3-c]pyridine.

13. The pharmaceutical composition according to claim 10 wherein the compound of formula I is:
- 2-[[4-[[ethyl(phenylmethyl)amino]sulfonyl]benzoyl]amino]-6-ethyl-4,5,6,7-tetrahydrothieno[2,3-c]pyridine-3-carboxamide.

14. The pharmaceutical composition according to claim 10 wherein the compound of formula I is:
- 2-[[4-[(4-ethyl-1-piperazinyl)sulfonyl]benzoyl]amino]-6-ethyl-4,5,6,7-tetrahydrothieno[2,3-c]pyridine-3-carboxamide.

15. A method of inhibiting GAG-L-selectin interactions, comprising the step of administering to a subject in need thereof a therapeutically effective amount of a pharmaceutical composition comprising a compound of the general formula I:

wherein:
R₁ is selected from the group consisting of H; straight or branched alkyl of 1-6 carbon atoms; arylalkyl; substituted arylalkyl; cycloalkyl, optionally substituted with alkyl groups; alkanoyl; arylcarbonyl optionally substituted at the aryl group; cycloalkylcarbonyl; alkoxycarbonyl;

R₂ is selected from the group consisting of; aminocarbonyl; alkylaminocarbonyl; arylaminocarbonyl optionally substituted at the aryl group; dialkylaminocarbonyl wherein each alkyl is straight or branched chain $C_1$-$C_6$ alkyl or both alkyl groups together may form a 3-7 membered saturated, unsaturated or aromatic monocyclic or bicyclic nitrogen containing heterocyclyl, optionally containing one or two additional heteroatoms; benzothiazol-2-yl;

R₃ and R₄ are selected from the group consisting of $C_1$-$C_6$ alkyl, optionally substituted by hydroxy, alkoxy, amino or alkylamino, $C_2$-$C_4$ monounsaturated alkenyl, cycloalkyl, aryl, arylmethyl, or R₃ and R₄ together may form an optionally substituted 5-7 membered saturated, monocyclic nitrogen containing heterocyclyl, optionally containing one or two additional heteroatoms, or R₃ and R₄ together may form an optionally substituted 5-7 membered unsaturated or aromatic monocyclic or bicyclic nitrogen containing heterocyclyl, optionally containing one or two additional heteroatoms;

R₅, R₆, R₇ and R₈ are selected from the group consisting of H or $C_1$-$C_6$ alkyl, with the proviso that when R₅, R₆, R₇ and R₈ are $C_1$-$C_6$ alkyl, R₁ is hydrogen;

and pharmaceutically acceptable salts thereof; further comprising a pharmaceutically acceptable diluent or carrier.

16. The method according to claim 15 wherein R₁ is selected from the group consisting of methyl, ethyl, 1-methylethyl, phenylmethyl, acetyl, ethoxycarbonyl and R₅=R₆=R₇=R₈ are hydrogens.

17. The method according to claim 15 wherein R₁ is hydrogen and R₅=R₆=R₇=R₈ are hydrogens or methyl groups.

18. The method according to claim 15 wherein R₁=R₅=R₆ is methyl and R₇=R₈ are hydrogens.

19. The method according to claim 15 wherein R₂ is selected from the group consisting of aminocarbonyl, methylaminocarbonyl, dimethylaminocarbonyl, pyrrolidinylcarbonyl, piperidinylcarbonyl, morpholinylcarbonyl, (3,5-dimethyl-1H-pyrazolyl) carbonyl, benzothiazol-2-yl.

20. The method according to claim 15 wherein R₃ and R₄ are selected from the group consisting of methyl, ethyl, propyl, butyl, methoxyethyl, chlorobutyl, cyanoethyl, phenyl, cyclopentyl, cyclohexyl, phenylmethyl, allyl or crotyl, R₃ and R₄ may be equal or different.

21. The method according to claim 15 wherein R₃ and R₄ form pyrrolidine, piperidine, 2-methyl, 3-methyl, 4-methyl or 3,5-dimethyl piperidine, perhydroazepine, morpholine, piperazine, 4-methylpiperazine, 3,4-dihydro-2(1H)-isoquinolinyl, 3,4-dihydro-1(2H)quinoline, and substituted derivatives thereof.

22. The method according to claim 15 wherein the compound of formula I is selected from:
2-[[4-[(ethylbutylamino)sulfonyl]benzoyl]amino]-3-(benzothiazol-2-yl)-6-ethyl-4,5,6,7-tetrahydrothieno[2,3-c]pyridine;
2-[[(4-(3,4-dihydro-2(1H)-isoquinolinyl)sulfonyl]benzoyl]amino]-6-(1-methylethyl)-4,5,6,7-tetrahydrothieno[2,3-c]pyridine-3-carboxamide;
2-[[4-(methylphenylamino)sulfonyl]benzoyl]amino]-6-(1-methylethyl)-4,5,6,7-tetrahydrothieno[2,3-c]pyridine-3-carboxamide;
2-[[4(3,4-dihydro-2(1H)-isoquinolinyl)sulfonyl]benzoyl]amino]-4,5,6,7-tetrahydro-5,5,7,7-tetramethylthieno[2,3-c]pyridine-3-carboxamide;
2-[[4-[(diethylamino)sulfonyl]benzoyl]amino]-3-(benzothiazol-2-yl)-6-ethyl-4,5,6,7-tetrahydrothieno[2,3-c]pyridine;
2-[[4-(morpholinylsulfonyl)benzoyl]amino]-3-(benzothiazol-2-yl)-6-(1-methylethyl)-4,5,6,7-etrahydrothieno[2,3-c]pyridine;
2-[[4-(3,4-dihydro-1(2H)-quinolinyl)sulfonyl]benzoyl]amino]-3-(benzothiazol-2-yl)-4,5,6,7-tetrahydro-5,5,7,7-tetramethylthieno[2,3-c]pyridine;
2-[[4-[[4-(methyl)-1-piperazinyl]sulfonyl]benzoyl]amino]-3-(benzothiazol-2-yl)-6-methyl-4,5,6,7-tetrahydrothieno[2,3-c]pyridine;
2-[[4-[(methylphenylamino)sulfonyl]benzoyl]amino]-3-(benzothiazol-2-yl)-6-methyl-4,5,6,7-tetrahydrothieno[2,3-c]pyridine;
2-[[4-(morpholinylsulfonyl)benzoyl]amino]-3-(benzothiazol-2-yl)-6-methyl-4,5,6,7-tetrahydrothieno[2,3-c]pyridine;
2-[[4-[[4-(3-methyl-1-piperidinyl)]sulfonyl]benzoyl]amino]-3-(benzothiazol-2-yl)-6-methyl4,5,6,7-tetrahydrothieno[2,3-c]pyridine;
2-[[4-[(diethylamino)sulfonyl]benzoyl]amino]-3-(benzothiazol-2-yl)-6-(phenylmethyl)-4,5,6,7-tetrahydrothieno[2,3-c]pyridine;
2-[[4-[(diethylamino)sulfonyl]benzoyl]amino]-3-(benzothiazol-2-yl)-6-methyl4,5,6,7-tetrahydrothieno[2,3-c]pyridine;
2-[[4-[[4-(ethoxycarbonyl)-1-piperazinyl]sulfonyl]benzoyl]amino]-4,5,6,7-tetrahydro-5,5,7,7-tetramethylthieno[2,3-c]pyridine-3-carboxamide;
2-[[4-[(cyclohxylmethylamino)sulfonyl]benzoyl]amino]-4,5,6,7-tetrahydro-5,5,7,7-tetramethylthieno[2,3-c]pyridine-3-carboxamide;
2-[[4-[(di-2-methoxyethylamino)]sulfonyl]benzoyl]-4,5,6,7-tetrahydro-5,5,7,7-tetramethylthieno[2,3-c]pyridine-3-carboxamide;
2-[[4-[(diethylamino)sulfonyl]benzoyl]amino]-3-(benzothiazol-2-yl)-6-methyl-4,5,6,7-tetrahydrothieno[2,3-c]pyridine;
2-[[4-[(diethylamino)sulfonyl]benzoyl]amino]-3-(benzothiazol-2-yl)-6-(1-methylethyl)-4,5,6,7-tetrahydrothieno[2,3-c]pyridine;
2-[[4-[(di-2-methoxyethylamino)sulfonyl]benzoyl]-amino]-3-(benzothiazol-2-yl)-6-methyl-4,5,6,7-tetrahydrothieno[2,3-c]pyridine;
2-[[4-[(methylphenylamino)sulfonyl]benzoyl]amino]-3-(benzothiazol-2-yl)-6-methyl-4,5,6,7-tetrahydrothieno[2,3-c]pyridine;
2-[[4-[[4-(ethoxycarbonyl)-1-piperazinyl]sulfonyl]benzoyl]amino]-3-(benzothiazol-2-yl)-6-methyl-4,5,6,7-tetrahydrothieno[2,3-c]pyridine;
2-[[4-(diethylamino)sulfonyl]benzoyl]amino]-4,5,6,7-tetrahydro-5,5,7,7-tetramethylthieno[2,3-c]pyridine-3-carboxamide;
2-[[4-[(methylphenylamino)sulfonyl]benzoyl]amino]-6-ethyl-4,5,6,7-tetrahydrothieno[2,3-c]pyridine-3-carboxylic acid methylamide;
2-[[4-[[ethyl(phenylmethyl)amino]sulfonyl]benzoyl]amino]-6-ethyl-4,5,6,7-tetrahydrothieno[2,3-c]pyridine-3-carboxamide;
2-[[4-[(4-methyl-1-piperazinyl)sulfonyl]benzoyl]amino]-6-ethyl-4,5,6,7-tetrahydrothieno[2,3-c]pyridine-3-carboxamide;
2-[[(4-(3,4-dihydro-1(2H)-quinolinyl)sulfonyl]benzoyl]amino]-6-ethyl-4,5,6,7-tetrahydrothieno[2,3-c]pyridine-3-carboxylic acid methylamide;

2-[[4-[(4-methyl-1-piperazinyl)sulfonyl]benzoyl]amino]-6-ethyl-4,5,6,7-tetrahydrothieno[2,3-c]pyridine-3-carboxylic acid methylamide;

2-[[4-[(4-methyl-1-piperazinyl)sulfonyl]benzoyl]amino]-3-(benzothiazol-2-yl)-6-ethyl-4,5,6.7-tetrahydrothieno[2,3-c]pyridine;

2-[[4-(diethylamino)sulfonyl]benzoyl]amino]-6-ethyl-4,5,6,7-tetrahydrothieno[2,3-c]pyridine-3-carboxylic acid N-methylamide;

2-[[4-(diethylamino)sulfonyl]benzoyl]amino]-6-ethyl-4,5,6,7-tetrahydrothieno[2,3-c]pyridine-3-carboxylic acid morpholinylamide.

23. The method according to claim 22 wherein the compound of formula I is:

2-[[4-[(ethylbutylamino)sulfonyl]benzoyl]amino]-3-(benzothiazol-2-yl)-6-ethyl-4,5,6,7-tetrahydrothieno[2,3-c]pyridine.

24. The method according to claim 22 wherein the compound of formula I is:

2-[[4-[(diethylamino)sulfonyl]benzoyl]amino]-3-(benzothiazol-2-yl)-6-ethyl-4,5,6,7-tetrahydrothieno[2,3-c]pyridine.

25. The method according to claim 22 wherein the compound of formula I is:

2-[[4-[[ethyl(phenylmethyl)amino]sulfonyl]benzoyl]amino]-6-ethyl-4,5,6,7-tetrahydrothieno[2,3-c]pyridine-3-carboxamide.

26. The method according to claim 22 wherein the compound of formula I is:

2-[[4-[(4-ethyl-1-piperazinyl)sulfonyl]benzoyl]amino]-6-ethyl-4,5,6,7-tetrahydrothieno[2,3-c]pyridine-3-carboxamide.

27. The method according to claim 15 wherein the disease or disorder related to cell adhesion or cell migration is an inflammatory process.

28. A method for treatment of inflammatory bowel disease comprising the step of administering to a subject in need thereof a therapeutically effective amount of a pharmaceutical composition comprising as an active ingredient a thieno[2,3-c]pyridine compound of formula 2-[[4-[(diethylamino)sulfonyl]benzoyl]amino]-3-(benzothiazol-2-yl)-6-ethyl-4,5,6,7-tetrahydrothieno[2,3-c]pyridine and a pharmaceutically acceptable salt thereof; further comprising a pharmaceutically acceptable carrier or diluent.

* * * * *